United States Patent
Hongo

(10) Patent No.: US 10,482,201 B2
(45) Date of Patent: Nov. 19, 2019

(54) INFORMATION PROCESSING APPARATUS, INFORMATION PROCESSING METHOD, AND PROGRAM

(71) Applicant: Sony Corporation, Tokyo (JP)

(72) Inventor: Kazuhiro Hongo, Kanagawa (JP)

(73) Assignee: Sony Corporation, Tokyo (JP)

(*) Notice: Subject to any disclaimer, the term of this patent is extended or adjusted under 35 U.S.C. 154(b) by 977 days.

(21) Appl. No.: 14/508,625

(22) Filed: Oct. 7, 2014

(65) Prior Publication Data

US 2015/0127273 A1    May 7, 2015

(30) Foreign Application Priority Data

Nov. 1, 2013  (JP) .................................. 2013-227937
Jul. 24, 2014  (JP) .................................. 2014-150694

(51) Int. Cl.
  *G06F 17/50*    (2006.01)
  *G01N 33/00*    (2006.01)

(52) U.S. Cl.
  CPC . *G06F 17/5018* (2013.01); *G01N 2033/0095* (2013.01)

(58) Field of Classification Search
  CPC ............ G01N 33/00; G01N 2033/0095; G06F 17/5018
  USPC .......................................................... 703/2
  See application file for complete search history.

(56) References Cited

U.S. PATENT DOCUMENTS

| | | | | |
|---|---|---|---|---|
| 7,505,885 B2* | 3/2009 | Deobald | ............. | G06F 17/5018 428/304.4 |
| 2008/0015827 A1* | 1/2008 | Tryon, III | ............. | G06F 11/008 703/2 |
| 2014/0107948 A1* | 4/2014 | Amann | ............... | G06F 17/5018 702/35 |

FOREIGN PATENT DOCUMENTS

| | | |
|---|---|---|
| JP | 2010-160028 | 7/2010 |
| JP | 2011-204081 | 10/2011 |

OTHER PUBLICATIONS

Aslantaş, K., and S. Taşgetiren. "A study of spur gear pitting formation and life prediction." Wear 257.11 (2004). pp. 1167-1175.*

Maligno, A. R., D. C. Whalley, and V. V. Silberschmidt. "Thermal fatigue life estimation and fracture mechanics studies of multilayered mems structures using a sub-domain approach." World Journal of Mechanics 2.02 (2012). pp. 61-76.*

(Continued)

*Primary Examiner* — Kamini S Shah
*Assistant Examiner* — John E Johansen
(74) *Attorney, Agent, or Firm* — Michael Best & Friedrich LLP

(57) ABSTRACT

Provided is an information processing apparatus including a crack leading edge candidate extraction unit configured to extract a crack leading edge candidate after progress of a crack in a structure, an elastic energy release rate calculation unit configured to calculate an elastic energy release rate that indicates an elastic energy released when the crack progresses to the extracted crack leading edge candidate, and a crack leading edge decision unit configured to decide a crack leading edge after the progress of the crack at least based on the elastic energy release rate. The crack leading edge candidate extraction unit extracts the crack leading edge candidate that satisfies a predetermined condition from crack (Continued)

leading edge candidates obtained in terms of a construction of the structure.

18 Claims, 41 Drawing Sheets

(56) References Cited

OTHER PUBLICATIONS

Ståhle, Per, Christina Bjerkén, and Andrey P. Jivkov. "On dissolution driven crack growth." International journal of solids and structures 44.6 (2007). pp. 1880-1890.*

Tvergaard, Viggo. "Resistance curves for mixed mode interface crack growth between dissimilar elastic-plastic solids." Journal of the Mechanics and Physics of Solids 49.11 (2001). pp. 2689-2703.*

Guo, Yajun, and John A. Nairn. "Calculation of J-integral and stress intensity factors using the material point method." Computer Modeling in Engineering and Sciences 6 (2004). pp. 295-308.*

Kimura, Masato, and Takeshi Takaishi. "Phase field models for crack propagation." Theoretical and Applied Mechanics Japan 59 (2011). pp. 85-90. (Year: 2011).*

Ming-Yuan, He, and John W. Hutchinson. "Crack deflection at an interface between dissimilar elastic materials." International Journal of Solids and Structures 25.9 (1989). pp. 1053-1067. (Year: 1989).*

Newman, J. C., and I. S. Raju. "Stress-intensity factors for internal surface cracks in cylindrical pressure vessels." Journal of Pressure Vessel Technology 102.4 (1980). pp. 342-346. (Year: 1980).*

Wang, Dong, et al. "Extended finite element modeling of crack propagation in ceramic tool materials by considering the microstructural features." Computational Materials Science 77 (May 2013). pp. 236-244. (Year: 2013).*

Kimura, Masato, and Takeshi Takaishi. "Phase field models for crack propagation." Theoretical and Applied Mechanics Japan 59 (2011). pp. 85-90. (Year: 2011).*

Remmers, J. J. C., Rene de Borst, and A. Needleman. "A cohesive segments method for the simulation of crack growth." Computational mechanics;31.1-2 (2003). pp. 69-77. (Year: 2003).*

* cited by examiner

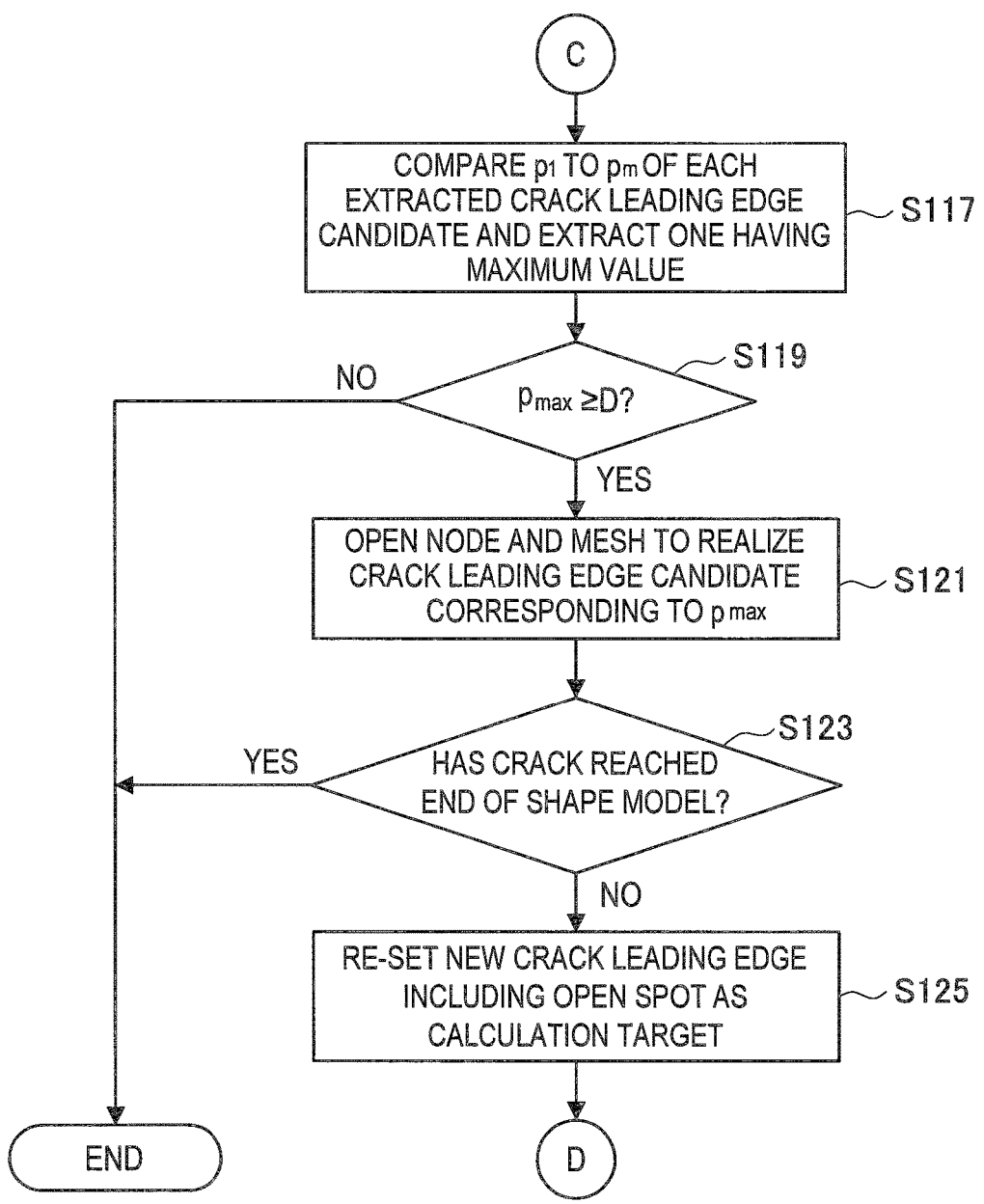

INFORMATION PROCESSING APPARATUS, INFORMATION PROCESSING METHOD, AND PROGRAM

CROSS REFERENCE TO RELATED APPLICATIONS

This application claims the benefit of Japanese Priority Patent Application JP 2013-227937 filed Nov. 1, 2013, and Japanese Priority Patent Application JP 2014-150694 filed Jul. 24, 2014, the entire contents of each of which are incorporated herein by reference.

BACKGROUND

The present disclosure relates to an information processing apparatus, an information processing method, and a program.

Cracks sometimes occur inside semiconductor devices due to thermal or mechanical stress exerted during various processes. In order to prevent such occurrence of cracks, various methods for analyzing the progress of cracks in a structure have been proposed.

For example, JP 2010-160028A discloses a technology in which a crack-containing cross section in a structure formed by welding different kinds of materials is focused on and the progress of the crack in the cross section is analyzed based on an algorithm using the J integrated value and the stress intensity factor. In addition, as another technique, JP 2011-204081A discloses a technology with regard to a leading edge of a crack arising in a structure to be analyzed, in which an elastic energy release rate of each node adjacent to the leading edge of the crack in the direction in which the crack is progressing is computed using a finite element method (FEM) to analyze the progress of the crack.

SUMMARY

In recent years, as semiconductor devices have been miniaturized and used in various applications as customized products, the structures and manufacturing processes of the devices have become sophisticated. In this situation, in order to establish a more stable manufacturing process or to secure high reliability even under diversified use environments, a crack progress analysis technology with high adaptability which can analyze, for example, progress of a crack that occurs between different kinds of materials and three-dimensional progress of a crack has been demanded.

Herein, the algorithm that uses the J integrated value and the stress intensity factor as described in JP 2010-160028A originally targets a two-dimensional displacement field composed of a single material for analysis and thus is not suitable for analysis of progress of a crack occurring in, for example, a structure that includes a plurality of materials. In the technology described in JP 2010-160028A, in order to apply the algorithm to the structure composed of the different kinds of materials, a process in which various physical property values of the cross section that includes a crack are averaged according to area ratios of the different kinds of materials to homogenize the cross section and thereby the cross section is regarded as being formed of a single material is performed. In this method, however, it can only be determined whether or not a crack is progressing on a cross section of interest, and it is difficult to perform more thorough analysis, for example, analysis of a direction in which such a crack is progressing.

On the other hand, the algorithm that uses the elastic energy release rate as described in JP 2011-204081A can be said to have high adaptability in that it can also be applied to progress analysis of a crack that occurs in a structure composed of different kinds of materials. In the technology described in JP 2011-204081A, however, an expected mode of breaking is limited to exfoliation of a wiring layer in a semiconductor device, an analysis target face is uniformly decided in advance, and it is determined only whether exfoliation occurs on the target face. Generally, FEM calculation performed in order to obtain an elastic energy release rate is known to bear a heavy calculation load, and if the technology described in JP 2011-204081A is applied to analysis of the three-dimensional progress of a crack, it is difficult to realize the technology because of calculation time.

Considering the above circumstances, as a technology for analyzing progress of a crack, one in which higher adaptability and a lighter calculation load are compatible with each other has been demanded. Therefore, the present disclosure proposes a novel and improved information processing apparatus, information processing method, and program that have higher adaptability and can analyze progress of a crack under a lighter calculation load.

According to an embodiment of the present disclosure, there is provided an information processing apparatus including a crack leading edge candidate extraction unit configured to extract a crack leading edge candidate after progress of a crack in a structure, an elastic energy release rate calculation unit configured to calculate an elastic energy release rate that indicates an elastic energy released when the crack progresses to the extracted crack leading edge candidate, and a crack leading edge decision unit configured to decide a crack leading edge after the progress of the crack at least based on the elastic energy release rate. The crack leading edge candidate extraction unit extracts the crack leading edge candidate that satisfies a predetermined condition from crack leading edge candidates obtained in terms of a construction of the structure.

According to another embodiment of the present disclosure, there is provided an information processing method performed by a processor, the information processing method including extracting a crack leading edge candidate after progress of a crack in a structure, calculating an elastic energy release rate that indicates an elastic energy released when the crack progresses to the extracted crack leading edge candidate, and deciding a crack leading edge after the progress of the crack at least based on the elastic energy release rate. The crack leading edge candidate that satisfies a predetermined condition is extracted from crack leading edge candidates obtained in terms of a construction of the structure According to another embodiment of the present disclosure, there is provided a program causing a processor of a computer to realize functions of extracting a crack leading edge candidate after progress of a crack in a structure, calculating an elastic energy release rate that indicates an elastic energy released when the crack progresses to the extracted crack leading edge candidate, and deciding a crack leading edge after the progress of the crack at least based on the elastic energy release rate. The crack leading edge candidate that satisfies a predetermined condition is extracted from crack leading edge candidates obtained in terms of a construction of the structure.

According to the present disclosure, a total toughness energy that is an energy necessary when a crack progresses is set, and a crack leading edge candidate appropriate for the total toughness energy is extracted. Then, an elastic energy release rate is calculated for the extracted crack leading edge candidate, and thereby a crack leading edge after the progress of the crack is decided. Therefore, the number of calculations of the elastic energy release rate having a relatively heavy calculation load can be reduced.

According to the present disclosure described above, it is possible to analyze progress of a crack under a lighter calculation load while higher adaptability is provided. Note that the effect described above is not necessarily limitative, and along with or instead of the effect, any effect introduced in the present specification or other effect that can be understood from the present specification may be exhibited.

BRIEF DESCRIPTION OF THE DRAWINGS

FIG. 3B is a flowchart showing the process procedure of a crack progress analysis method according to the first embodiment;

DETAILED DESCRIPTION OF THE EMBODIMENTS

Figure 1A:
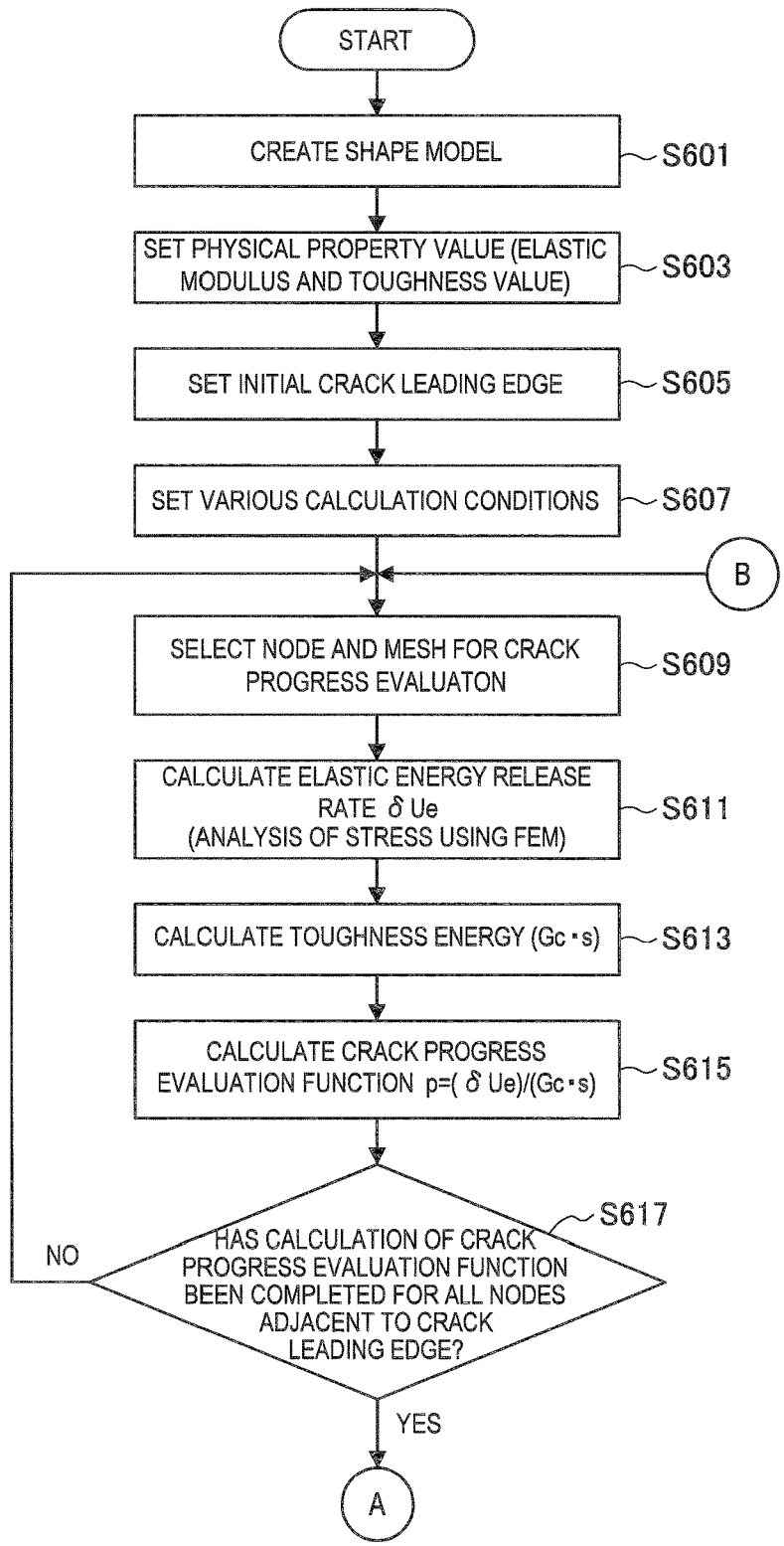
FIG. 1A is a flowchart showing a process procedure of a general crack progress analysis method.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. Review on a general crack progress analysis technology
1-1. Process procedure of a general crack progress analysis method
2. First Embodiment
2-1. Process procedure of a crack progress analysis method according to the first embodiment
2-2. Process of extracting a crack leading edge candidate
2-2-1. Condition for continuity of a crack leading edge
2-2-2. Condition for continuity before and after progress of a crack
2-3. Comparison of calculation loads
2-3-1. Calculation load in the general crack progress analysis method
2-3-2. Calculation load in the crack progress analysis method according to the first embodiment
3. Second Embodiment
3-1. Process procedure of a crack progress analysis method according to the second embodiment
3-2. Process of extracting crack leading edge candidates
3-2-1. Method of analyzing progress of a crack on a surface
3-2-2. Method of analyzing progress of a crack in a surface layer
3-3. Comparison of calculation loads
3-3-1. Calculation load of the general crack progress analysis method
3-3-2. Calculation load of the crack progress analysis method according to the second embodiment
4. Device configuration
5. Modified examples
5-1. Crack progress analysis in consideration of anisotropy
5-2. Crack progress analysis in consideration of an interface between different kinds of materials
5-3. Modified example in which the shape of meshes is different 5-4. Crack progress analysis in consideration of internal stress of a material
5-5. Two-dimensional crack progress analysis in consideration of three-dimensional anisotropy of toughness
5-6. Crack progress analysis when an external force factor condition changes
6. Hardware configuration
7. Supplement

1. Review on a General Crack Progress Analysis Technology

First, prior to providing description with respect to a preferred embodiment of the present disclosure, an existing crack progress analysis technology that has been generally performed will be described in order to further clarify the present disclosure. As a general crack progress analysis technology, a technique of computing an elastic energy release rate of each node adjacent to a leading edge of a crack in a direction in which the crack is progressing using the finite element method (FEM) is known.

(1-1. Process Procedure of a General Crack Progress Analysis Method)

Figure 1B:
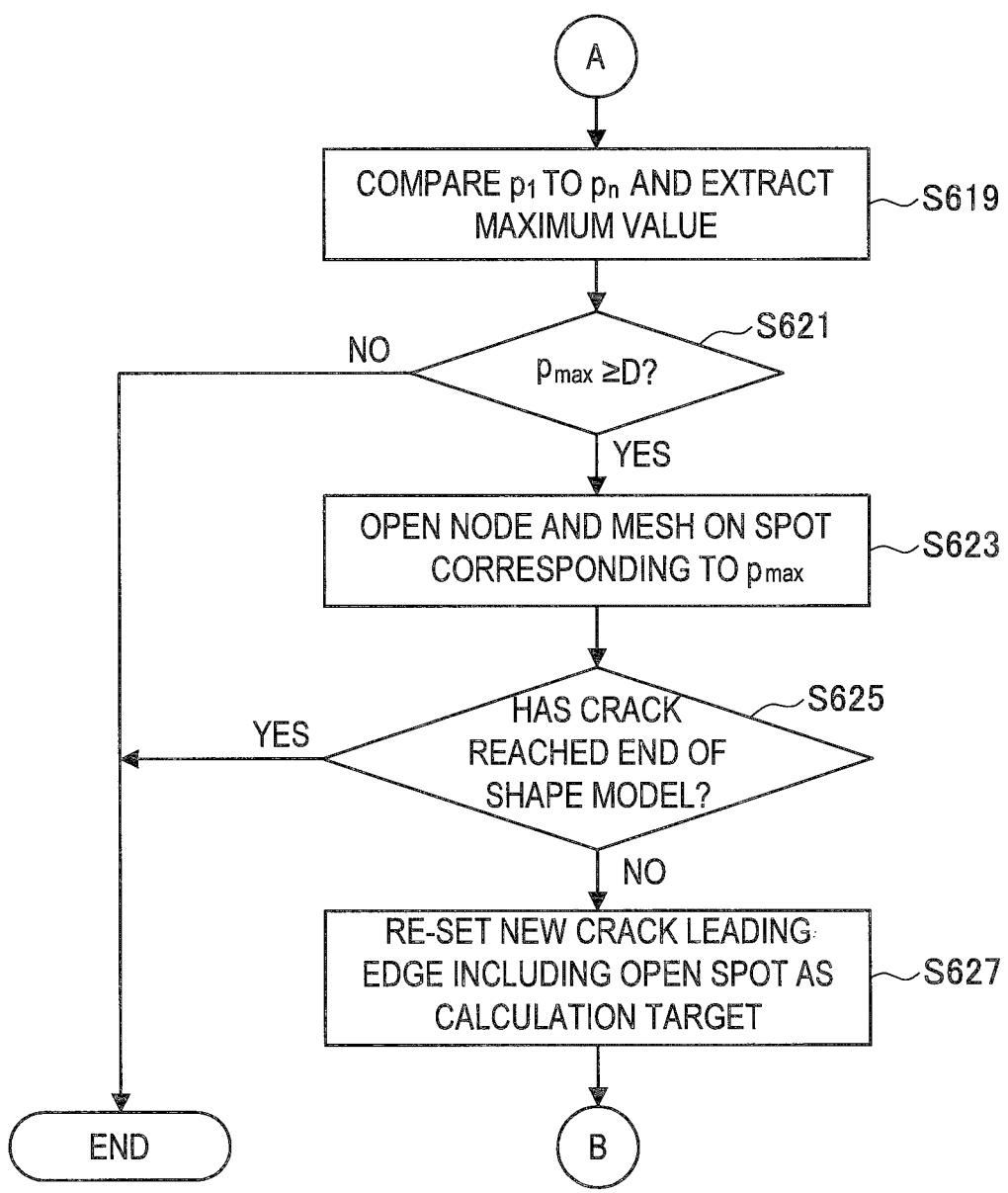
FIG. 1B is a flowchart showing a process procedure of a general crack progress analysis method.
Figure 2A:
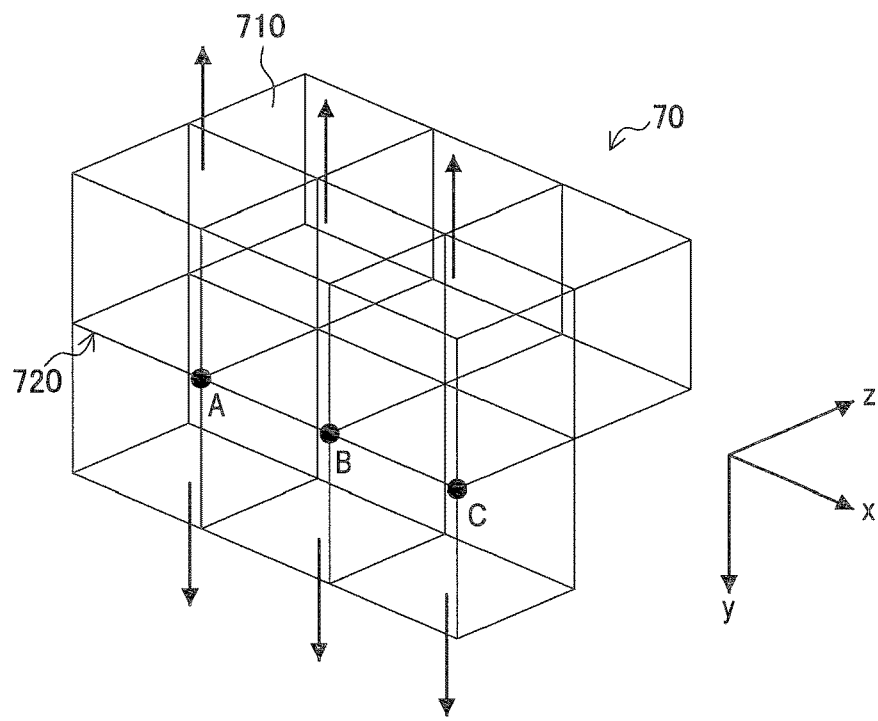
FIG. 2A is an illustrative diagram for describing calculation of an elastic energy release rate using the FEM in the general crack progress analysis method.
Figure 2B:
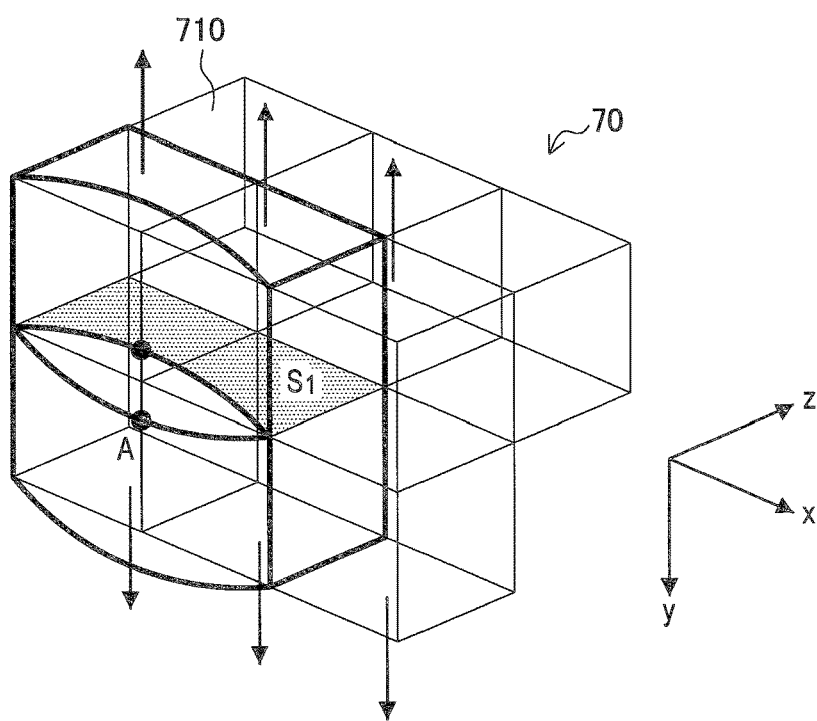
FIG. 2B is an illustrative diagram for describing calculation of an elastic energy release rate using the FEM in the general crack progress analysis method.
Figure 2C:
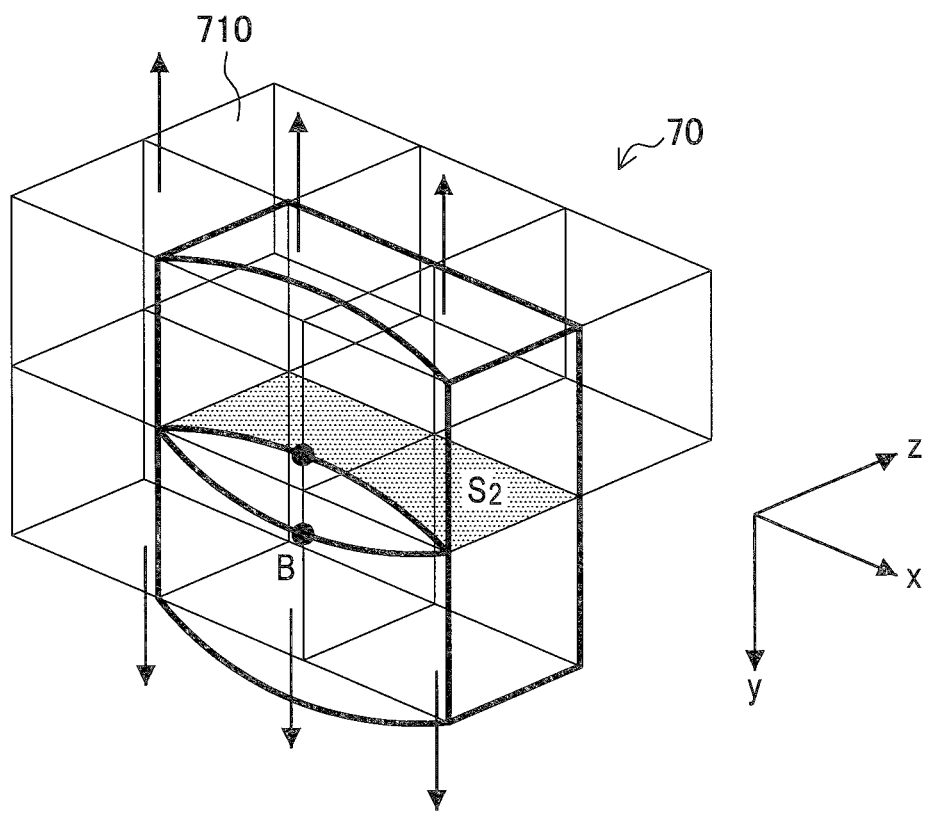
FIG. 2C is an illustrative diagram for describing calculation of an elastic energy release rate using the FEM in the general crack progress analysis method.

With reference to FIGS. 1A, 1B, and 2A to 2C, the process procedure of a general crack progress analysis method (information processing method) will be described. FIGS. 1A and 1B are flowcharts showing the process procedure of the general crack progress analysis method. In addition, FIGS. 2A to 2C are illustrative diagrams for describing calculation of an elastic energy release rate using the FEM in the general crack progress analysis method. Note that the processes in each of the steps shown in FIGS. 1A and 1B can be executed when a processor of each of various kinds of information processing apparatuses, for example, personal computers (PCs), workstations (WSs), and the like operates according to a predetermined program.

Referring to FIGS. 1A and 1B, in the general crack progress analysis method, a shape model expressing a structure to be analyzed is first created (Step S601). The shape model may have, for example, a three-dimensional shape and may be configured as a combination of a plurality of different materials. In the process indicated by Step S601, a general technique may be used for creating a shape model in the FEM, and thus detailed description thereof is omitted.

Next, various physical property values according to the materials of the structure are set for the shape model created in Step S601 (Step S603). The set physical property values may be various physical property values used in general FEM calculation including, for example, values of an elastic modulus and a toughness value of the materials (including a toughness value per unit area to be described later), and the like. In addition, when a structure is composed of different kinds of materials, adherence forces of the interfaces of the different kinds of materials may be set.

Next, an initial crack leading edge is set for the shape model created in Step S601 (Step S605). A crack leading edge is an edge portion of a crack in the direction in which the crack is progressing. The progress of a crack is analyzed by calculating the position of the crack leading edge appearing one session later based on the position of the set initial crack leading edge. In this manner, in the analysis of the progress of a crack, the progress of a crack is analyzed from the initial crack leading edge.

Next, various calculation conditions are set for the analysis of the progress of the crack (Step S607). For example, in the process shown in Step S607, meshes are formed in a shape model while the initial crack leading edge set in Step S605 is considered. Specifically, the shape model is divided into a plurality of meshes so that at least the initial crack leading edge is positioned on the boundary of meshes. The meshes are a computational grid serving as a unit of a calculation target in numerical calculation, and corresponds to elements (or factors) in the FEM. The formation of the meshes may be performed through various techniques generally used in the FEM. In addition, at the same time as the formation of the meshes, virtual nodes (joints) which are used for the calculation are set on points which come into contact with the initial crack leading edge on the boundary of the meshes.

In addition, in the process of Step S607, an external force factor condition which is a condition indicating external force exerted on the structure (shape mode) may be set. With respect to the shape model on which the predetermined external force is exerted based on the external force factor condition, stress is analyzed using the FEM in the process shown in Step S611 to be described later.

In addition, in the process of Step S607, arithmetic operation formulas of an elastic energy release rate and a toughness energy to be calculated in the processes shown in Steps S611 and S613 to be described later, a definition formula of a crack progress evaluation function to be calculated in the process shown in Step S615, a threshold value D to be compared to the crack progress evaluation function, and the like may be set.

FIG. 2A schematically shows a shape model 70 in the stage in which a mesh formation process has ended. In the example shown in FIG. 2A, the shape model 70 is divided into a plurality of cubic meshes 710. In addition, the shape model 70 is divided such that an initial crack leading edge 720 (indicated by a dashed line in the drawing) is positioned on the boundary between the meshes 710. Furthermore, in the shape model 70, nodes A, B, and C are set at the points which come into contact with the initial crack leading edge 720 on the boundary of the meshes 710.

Note that, in description below, a direction in which a crack progresses in the shape model is referred to as a z-axis direction as shown in FIG. 2A. The positive direction of the z axis is the direction in which the crack progresses. In addition, two directions which are orthogonal to each other in the plane perpendicular to the z axis are referred to as an x-axis direction and a y-axis direction. When the meshes formed by dividing the shape model are cubes or cuboids, the directions parallel to two orthogonal sides which form each mesh are set to the x-axis direction and the y-axis direction.

As described above, a crack progresses from the initial crack leading edge 720. Thus, in the shape model 70 shown in FIG. 2A, the meshes 710 are separated from at least one of the nodes A, B, and C in the y-axis direction, and accordingly, the progress of a crack from the initial crack leading edge 720 can appear. Therefore, by evaluating a degree of ease of separation of the meshes 710 for each of the nodes A, B, and C, a crack leading edge appearing one session later can be estimated. Note that FIGS. 2A to 2C use arrows to schematically illustrate force that is exerted in the direction in which the meshes 710 are separated when a crack progresses.

Returning to FIGS. 1A and 1B, the evaluation of a degree of ease of separation of the meshes 710 in the general crack progress analysis method will be described in detail. In the evaluation, first, a node and meshes for evaluating the progress of a crack are selected (Step S609). The node and the meshes for evaluating the progress of a crack refer to any node adjacent to the initial crack leading edge and a mesh which has the node on its boundary. Here, in order to evaluate separation of the meshes 710 at the node A shown in FIG. 2A, i.e., the progress of a crack at the node A, for example, the node A and the meshes 710 that are present on both sides of the y-axis direction of the node A are assumed to be selected.

Next, an elastic energy release rate when the crack progresses from the node A is calculated (Step S611). The elastic energy release rate is that of an elastic energy released when the meshes are separated in the shape model, and is defined in the general crack progress analysis method by the difference between the elastic energy of a whole system before the meshes are separated (before opening of the node) and the elastic energy of the whole system after the meshes are separated (after opening of the node).

Specifically, in the calculation of the elastic energy release rate, analysis of stress using the FEM is performed. First, distribution of stress acting in the shape model is calculated with respect to the state before the opening of the node as shown in FIG. 2A using the FEM under the predetermined external force factor condition, and thereby the elastic energy that the whole system has in the state before the opening of the node is computed. Next, the shape mode expressing the state in which the node A is open is created as shown in FIG. 2B, then distribution of stress acting in the shape model in which the node A is open is calculated using the FEM under the predetermined external force factor condition likewise, and thereby the elastic energy that the whole system has in the state after the opening of the node is computed. When the difference between the computed elastic energies is taken, the elastic energy release rate $\delta U_{e1}$ is calculated (the final "1" indicates that the rate is a calculation result of the node A). In the state in which the node A is open as shown in FIG. 2B, there is a gap between the meshes 710 positioned on both sides of the y-axis direction of the node A, and elastic force acts in the meshes 710 in the direction in which the gap is closed. Components of the elastic force are expressed as the difference of the elastic energies before and after the opening of the node in the system. Note that, for a specific calculation method of an elastic energy using the FEM, an existing known method may be applied, and thus detailed description thereof will be omitted.

When the elastic energy release rate is computed, next, a toughness energy when the crack progresses from the node A is calculated (Step S613). The toughness energy refers to an energy necessary for separating the meshes in the shape model. To be specific, the toughness energy at the time of the progress of a crack is obtained by multiplying a toughness value $G_c$ per unit area by an area s of a separation face that can be generated between the meshes 710 due to the crack. The toughness value $G_c$ per unit area is a physical property parameter inherent to a material constituting the structure, and can be set together when, for example, a physical property value of the shape model is set in the process shown in Step S603. In addition, the area s of the separation face can be set based on, for example, the size (the area of one face) of the meshes 710 formed in the process shown in Step S607.

In the example shown in FIG. 2B, in the state in which the node A is open, in other words, when the crack progresses at the node A, a separation face that has an area $s_1$ is generated between the meshes 710. Thus, the toughness energy generated when the crack progresses from the node A can be calculated as $G_c \cdot s_1$.

When the elastic energy release rate and the toughness energy are computed, next, a crack progress evaluation function for evaluating ease of the progress of the crack at the node A is computed based on the values (Step S615). The progress of the crack can be evaluated by comparing the elastic energy release rate to the toughness energy. To be specific, when the elastic energy release rate is greater than the toughness energy, in other words, when the energy that can be released from the progress of the crack is greater than the energy necessary for causing the crack to progress, the crack is expected to progress. Thus, the crack progress evaluation function is defined as a function with which the magnitude relation between an elastic energy release rate and a toughness energy can be compared. In the example shown in FIGS. 1A and 1B, a crack progress evaluation function p is defined as a ratio of an elastic energy release rate to a toughness energy, i.e., $p=(\delta U_e)/(G_c \cdot s)$. In this case, a crack can be considered to easily progress as the value of the crack progress evaluation function p becomes greater. The crack progress evaluation function $p_1$ of the node A is computed as $p_1=(\delta U_{e1})/(G_c \cdot s_1)$ using the elastic energy release rate $\delta U_{e1}$ calculated in Step S611 and the toughness energy $G_c \cdot s_1$ calculated in Step S613.

When the crack progress evaluation function $p_1$ of the node A is calculated, next, it is determined whether or not calculation of crack progress evaluation functions p of all nodes adjacent to the crack leading edge has been completed (Step S617). When the calculation of the crack progress evaluation functions p of all nodes is determined to have been completed in Step S617, the process proceeds to Step S619. On the other hand, when the calculation of the crack progress evaluation functions p of all nodes is determined not to have been completed, the process returns to Step S609 and then the processes shown in Steps S609 to S615 are repeated for other nodes. In the example of the shape model 70 shown in FIG. 2A, there are other nodes (nodes B and C) that can be targets of analysis in addition to the node A as nodes adjacent to the crack leading edge 720, and thus, returning to Step S609, the processes shown in Steps S609 to S615 are performed for the nodes B and C.

For example, when progress of the crack at the node B is evaluated, the node B and meshes 710 positioned at both sides of the y-axis direction of the node B are selected as a node and meshes for evaluating the progress of the crack in Step S609 (Step S609). Then, as shown in FIG. 2C, the shape model 70 in which the node B is open is created, and then using the shape model 70, an elastic energy release rate $\delta U_{e2}$ and a toughness energy $G_c \cdot s_2$ when the crack progresses at the node B are calculated (Steps S611 and S613). Further, using the calculated elastic energy release rate $\delta U_{e2}$ and the toughness energy $G_c \cdot s_2$, a crack progress evaluation function $p_2$ of the node B is calculated as $p_2=(\delta U_{e2})/(G_c \cdot s_2)$ (Step S615).

In the same manner, a crack progress evaluation function $p_3$ of the node C is also calculated as $p_3=(\delta U_{e3})/(G_c \cdot s_3)$. Although there are only three nodes A, B, and C adjacent to the crack leading edge 720 in the example shown in FIG. 2A for the sake of simplification, more generally, when there are n (n is an arbitrary natural number) nodes adjacent to the crack leading edge 720, n crack progress evaluation functions $p_1$ to $p_n$ corresponding to each of the nodes are calculated. When the crack progress evaluation functions $p_1$ to $p_n$ are calculated for all of the nodes, the values $p_1$ to $p_1$, are compared, and then the maximum value ($p_{max}$) is extracted (Step S619). In the example shown in FIGS. 1A and 1B, the definition of the elastic energy release rates, the toughness energy, and the crack progress evaluation functions is considered to indicate that a crack easily occurs when the value of a crack progress evaluation function p is greater, and thus, in the process shown in Step S619, the crack progress evaluation functions p corresponding to the node at which the crack progresses most easily is extracted.

Next, it is determined whether or not the crack progress evaluation function $p_{max}$ that is the maximum value is equal to or greater than a predetermined value D (Step S621). Here, the predetermined value D is a threshold value for evaluating whether or not a crack will progress, and in the example shown in FIGS. 1A and 1B, for example, D=1 can be set. As described above, since the crack is expected to progress when the elastic energy release rate is greater than the toughness energy, when $p_{max}$<D=1, the crack is considered to no longer progress unless more external force or the like is applied based on the definition of the crack progress evaluation function. Thus, when $p_{max}$<D=1 is determined in Step S621, the series of the crack progress analysis process ends.

On the other hand, when $p_{max}$≥D=1, it indicates that there is a possibility of a crack progressing at least on a spot that corresponds to the crack progress evaluation function $p_{max}$. Thus, when it is determined that $p_{max}$≥D=1 in Step S621, the crack is regarded as progressing on the spot that corresponds to the crack progress evaluation function $p_{max}$, and a process of opening the node and the meshes 710 on the spot that corresponds to the crack progress evaluation function $p_{max}$ in the shape model 70 to allow the crack to progress (S623). Note that, although D=1 is set as the threshold value D in the example shown in FIGS. 1A and 1B because the crack progress evaluation function p is defined as a ratio of an elastic energy release rate to a toughness energy, the threshold value D may be arbitrarily set according to the definition of the crack progress evaluation function p as a value with which progress of a crack can be determined.

Next, based on the opening of the corresponding nodes and the meshes 710 in Step S623, it is determined whether or not the crack has reached an end of the shape model 70 (Step S625). When the crack has reached the end of the shape model 70, analysis of the progress of the crack is no longer possible in that direction, and thus the series of the crack progress analysis processes ends. On the other hand, when the crack has not reached the end of the shape model 70, there is a possibility of the crack still progressing in that direction. Thus, when it is determined that the crack has not reached the end of the shape model 70 in Step S623, a new crack leading edge including the open portion is re-set as a calculation target (Step S627), and the process of Step S609 and the following processes are repeated for all of the nodes adjacent to the new crack leading edge.

In the general crack progress analysis method, the processes shown in Steps S601 to S627 described above are repeated until nodes which are calculation targets are no longer open. The state in which the nodes are no longer open is a case in which the progress of the crack stops (in which it is determined that $p_{max}$<1 in Step S621 described above), or a case in which the crack has reached the end of the shape model 70 (when it is determined that the crack has reached the end of the shape model 70 in Step S625 as described above). When the crack has reached the end of the shape model 70, there is a case in which the shape model 70 is completely separated due to the progress of the crack. When the external force factor condition is changed even if $p_{max}$<D=1 is determined in Step S621 and the progress of the crack stops, the distribution of the stress in the shape model 70 can be changed, and the values of the elastic energy release rates can also be changed, and thus the series of processes may be repeated.

Hereinabove, the process procedure of the general crack progress analysis method has been described with reference to FIGS. 1A, 1B, and 2A to 2C. Note that, although the progress of a crack that occurs in a structure has been described in the above description, progress of exfoliation that occurs in a structure can also be analyzed in the same manner by, for example, setting a crack leading edge on the interface of different kinds of materials and then analyzing the progress of a crack along the interface.

As described above, in the general crack progress analysis method, the progress of a crack in only one mesh is analyzed in one session. In addition, in order to analyze the progress of a crack of one mesh, the elastic energy release rates, the toughness energies, and the crack progress evaluation functions of all nodes adjacent to a crack leading edge, i.e., all nodes which can be obtained in terms of the construction of a structure, are computed. Here, the calculation of the toughness energies and the crack progress evaluation functions is simple multiplication or division of scalars, and a calculation load thereof is not particularly heavy. For calculation of an elastic energy release rate, however, it is necessary to perform analysis of stress using the FEM. FEM calculation is generally known to have a heavy calculation load, and a calculation load of an elastic energy release rate, for example, can even be equal to or greater than 100 times the calculation load on the calculation of a toughness energy and a crack progress evaluation function. Thus, when there are a large number of nodes adjacent to a crack leading edge, a lengthy calculation time is needed only to analyze the progress of a crack of one mesh. When an evaluation target face, i.e., a crack progressing face, is limited only to a specific face, for example, a calculation load can be set to be relatively low, however, when a three-dimensional progressing direction of the crack is sought, the number of nodes adjacent to the crack leading edge increases, and thus the amount of calculation time becomes enormous. Thus, when analysis of the three-dimensional progress of a crack for which a direction of progress is not limited is attempted using the general crack progress method, there is a possibility of difficulty in completing analysis within a realistic time.

In light of the result of the review of the existing general crack progress analysis method described above, a crack progress analysis technology that enables analysis with a lighter calculation load while securing high adaptability that can respond to analysis of various kinds of cracks, for example, a crack that progresses penetrating different kinds of materials of a structure that is formed by combining the different kinds of materials, exfoliation on an interface, and a three-dimensionally progressing crack has been demanded. As a result of researching a technology that enables analysis of progress of a crack with a lighter calculation load while having higher adaptability based on the result of the review described above, the present inventors have attained first and second embodiments of the present disclosure to be described below. Hereinbelow, the first and second embodiments which are preferred embodiments of the present disclosure will be described.

2. First Embodiment

In the exemplary embodiments of the present disclosure, when a crack leading edge candidate found after progress of a crack in a structure is to be extracted, a crack leading edge candidate that satisfies a predetermined condition is extracted from crack leading edge candidates that can be taken in terms of the constitution of the structure. In this manner crack leading edge candidates are narrowed down based on the predetermined condition, rather than extracting crack leading edge candidates in a round-robin manner. By performing crack progress analysis based on a crack progress evaluation function as described above, for example, for the crack leading edge candidates which are narrowed down, it is possible to reduce the number of calculation processes of an elastic energy release rate accompanied by FEM calculation which takes a long period of calculation time, and thus to perform the crack progress analysis with a smaller calculation load.

Hereinafter, the two embodiments which are the first and second embodiments will be described as exemplary embodiments of the present disclosure, however, the embodiments have different conditions for extracting (or narrowing down) crack leading edge candidates. Hereinafter, the first and second embodiments will be described in order.

(2-1. Process Procedure of a Crack Progress Analysis Method According to the First Embodiment)

Figure 3A:
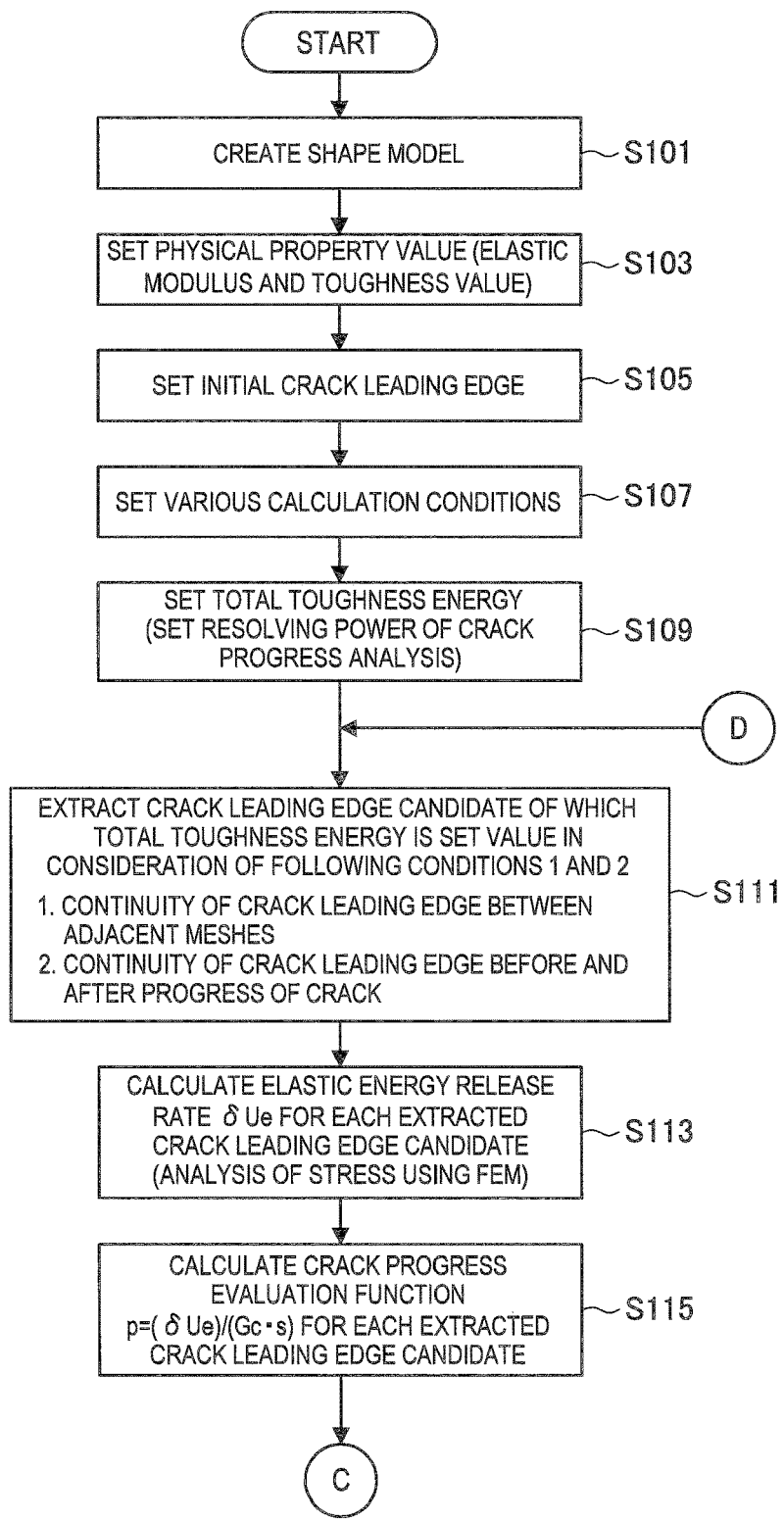
FIG. 3A is a flowchart showing the process procedure of a crack progress analysis method according to a first embodiment.

The process procedure of a crack process analysis method (information processing method) according to the first embodiment of the present disclosure will be described with reference to FIGS. 3A and 3B. FIGS. 3A and 3B are flowcharts showing the process procedure of the crack process analysis method according to the first embodiment. Note that the process in each step shown in FIGS. 3A and 3B can be executed when a processor of each of various kinds of information processing apparatuses, for example, PCs, workstations, and the like, operates in accordance with a predetermined program.

Referring to FIGS. 3A and 3B, first, a shape model expressing a structure to be analyzed is created in the crack process analysis method according to the first embodiment (Step S101). In the first embodiment, for example, the structure is composed of a plurality of different materials, and accordingly, the shape model can also be formed by combining a plurality of materials. The first embodiment, however, is not limited thereto, and the structure may be composed of a single material. The shape model has, for example, a three-dimensional shape. In the process shown in Step S101, a general technique of the FEM for creating a shape model may be used, and thus detailed description thereof will be omitted.

Next, various physical property values according to the materials of the structure are set for the shape model created in Step S101 (Step S103). The set physical property values may be various physical property values used in general FEM calculation including, for example, values of an elastic modulus and a toughness value of the materials (including a toughness value per unit area to be described later), and the like. In addition, when a structure is composed of different kinds of materials, adherence forces of the interfaces of the different kinds of materials may be set.

Next, an initial crack leading edge is set for the shape model created in Step S101 (Step S105). A crack leading edge is an edge portion of a crack in the direction in which the crack is progressing. The progress of a crack is analyzed by calculating the position of the crack leading edge appearing one session later based on the position of the set initial crack leading edge. In this manner, in the analysis of the progress of a crack, the progress of a crack is analyzed from the initial crack leading edge.

Next, various calculation conditions are set for crack progress analysis (Step S107). For example, in the process shown in Step S107, meshes are formed in the shape model while the initial crack leading edge set in Step S105 is considered. Specifically, the shape model is divided into a plurality of meshes so that at least the initial crack leading edge is on the boundary of the meshes. The meshes are computational grids serving as units of calculation targets in calculation of numerical values, and correspond to elements (factors) in the FEM. The meshes may be formed using various techniques which are generally used in the FEM, and may also have various shapes of, for example, a tetrahedron, a hexahedron, and the like. In addition, at the same time as the formation of the meshes, imaginary nodes (joints) used during calculation are set at points adjacent to the initial crack leading edge on the boundaries of the meshes.

In addition, in the process of Step S107, an external force factor condition which is a condition indicating external force exerted on the structure (shape mode) may also be set. With respect to the shape model on which the predetermined external force is exerted based on the external force factor condition, stress is analyzed using the FEM in the process shown in Step S611 to be described later.

In addition, in the process of Step S107, arithmetic operation formulas of an elastic energy release rate to be calculated in the processes shown in Steps S113 to be described later, a definition formula of a crack progress evaluation function to be calculated in the process shown in Step S115, a threshold value D to be compared to the crack progress evaluation function, and the like may be set.

In this manner, in the crack process analysis method according to the first embodiment, substantially the same processes as those shown in Steps S601 to S607 in the general crack progress analysis method described with reference to FIGS. 1A to 1B may be performed in the processes shown in Steps S101 to S107. The shape model in the stage in which the mesh formation process ends may be similar to, for example, the shape model 70 shown in FIG. 2A.

In the first embodiment, the processes after Step S107 are different from those of the general crack progress analysis method. In the first embodiment, after the process shown in Step S107, a process of setting the total toughness energy is performed (Step S109). The total toughness energy is defined as the sum of toughness energies necessary for separating a plurality of meshes during the progress of a crack. Specifically, the total toughness energy set in Step S109 is set as an energy necessary for separating the meshes when the crack progresses for one session. In other words, the total toughness energy set in Step S109 can be said to be a value for deciding an amount of progress of a crack in one session. Note that it is preferable to set a predetermined range for the total toughness energy in Step S109, rather than setting one value.

Next, crack leading edge candidates which are candidates for a crack leading edge after one session are extracted (Step S111). Specifically, in the process shown in Step S111, crack leading edge candidates of which the total toughness energy during the progress of the crack is likely to fall within the range of the total toughness energy set in Step S109 are extracted. For example, in Step S111, the crack leading edge candidates are extracted by extracting, in a round-robin manner, combinations of the meshes that are likely to be included in the predetermined range in which the total toughness energy at the time of separation is set among meshes which come into contact with the initial crack leading edge and are positioned in the progressing direction of the crack. Here, in the general crack progress analysis method described above, one node is focused and progress of a crack at the node is analyzed, and thus an amount of the progress of a crack in one session is limited for one mesh. Thus, a calculated toughness energy is calculated only as an energy necessary for separating a pair of meshes. On the other hand, in the first embodiment, the range of the total toughness energy for causing a crack to progress for one session is set and candidates for the crack leading edge that is likely to fall within the range in which the total toughness energy at the time of progress of the crack is set are extracted as described above. The so-called total toughness energy can be said to express a toughness energy necessary when a crack progresses to a crack leading edge candidate. Thus, by appropriately setting the total toughness energy in Step S109, it is possible to analyze progress of a crack spanning a plurality of nodes (in other words, a plurality of meshes) in one session.

In addition, in the process of extracting the crack leading edge candidate in Step S111, the following conditions 1 and 2 are considered along with the total toughness energy. In other words, they are a condition 1 for continuity of a crack leading edge and a condition 2 for continuity of a crack formed before and after its progress. The condition 1 is provided in order to prevent, for example, only a portion of a crack leading edge from progressing to be protrusive in comparison to other portions when a crack progresses. In addition, the condition 2 is provided in order to prevent a region of non-separation in a shape of an isolated field (shape of a floating island) from being present between meshes in a region in which the meshes are separated due to a crack when the crack progresses. By extracting the crack leading edge candidate that satisfies the conditions 1 and 2, shapes of crack leading edges that are not expected to be generated during actual progress of a crack are excluded from the candidate, and thus, it is possible to perform analysis of progress of a crack based on realities. Note that the process of extracting a crack leading edge candidate based on the conditions 1 and 2 will be described in detail in (2-2. Process of extracting a crack leading edge candidate) below.

Next, for each of extracted crack leading edge candidates, the elastic energy release rate $\delta U_e$ is calculated (Step S113). In the calculation of the elastic energy release rate $\delta U_e$, analysis of stress is performed using the FEM. To be specific, for the state in which a crack leading edge position is of the initial crack leading edge, distribution of stress in the shape model is calculated using the FEM under a predetermined external force factor condition, and thereby an elastic energy that the whole system has in the state in which the crack leading edge position is of the initial crack leading edge is calculated. Next, for the state in which the crack leading edge position is of a crack leading edge candidate, distribution of stress in the shape model is calculated using the FEM under the predetermined external force factor condition, and thereby an elastic energy that the whole system has in the state in which the crack leading edge position is of the crack leading edge candidate is calculated. By taking the difference between the computed elastic energies, the elastic energy release rate $\delta U_e$ is calculated. In Step S113, the calculation of the elastic energy release rate $\delta U_e$ is performed each of the extracted crack leading edge candidates. Herein, for m (m is an arbitrary natural number) crack leading edge candidates extracted in Step S111, each of elastic energy release rates $\delta U_{e1}$ to $\delta U_{em}$ is assumed to be calculated.

Here, in the general crack progress analysis method described above, one node is focused and the elastic energy release rate $\delta U_e$ is obtained from the difference of the elastic energies before and after the opening of the node in the process shown in Step S611. On the other hand, in the first embodiment, the elastic energy of the whole system in the state in which the crack leading edge position is of the initial crack leading edge and the elastic energy of the whole system in the state in which the crack leading edge position is of a crack leading edge candidate are calculated, and then, by calculating the difference between the values, each elastic energy release rate $\delta U_e$ is obtained. In this manner, elastic energy release rates $\delta U_e$ are obtained targeting a plurality of nodes and meshes in the present embodiment.

Next, for each of the extracted crack leading edge candidates, the crack progress evaluation function p is calculated (Step S115). The crack progress evaluation function p is an index indicating a possibility of realizing a crack leading edge candidate (a possibility of a crack progressing so as to realize a crack leading edge candidate). In the first embodiment, the progress of a crack can be evaluated by comparing an elastic energy release rate to the total toughness energy. To be specific, when an elastic energy release rate is greater than the total toughness energy, in other words, when an energy that can be released due to a progressing crack is greater than an energy necessary for causing a crack to progress, a crack is expected to progress. Thus, a crack progress evaluation function is defined as a function with which the magnitude relation of an elastic energy release rate and the total toughness energy can be compared.

In the example shown in FIGS. 3A and 3B, the crack progress evaluation function p is defined as a ratio of an elastic energy release rate to a total toughness energy, in other words, $p=(\delta U_e)/(G_c \cdot s)$. Note that, when the crack progress evaluation function p is calculated as a ratio of an elastic energy release rate to a total toughness energy, a predetermined coefficient may be multiplied if necessary. When m crack leading edge candidates are assumed to be extracted, $p_1=(\delta U_{e1})/(G_c \cdot s_1)$ to $p_m=(\delta U_{em})/(G_c \cdot s_m)$ with respect to m crack progress evaluation functions are calculated for the m crack leading edge candidates in Step S115. Here, $\delta U_e$ that is the numerator of the crack progress evaluation function p is the elastic energy release rate $\delta U_e$ that has been calculated in Step S113. In addition, $G_c \cdot$s that is the denominator of the crack progress evaluation function p is the total toughness energy necessary for separating the meshes when the crack leading edge progresses from the position of the initial crack leading edge to the position of a crack leading edge candidate. $G_c$ is a toughness value per unit area can be se when, for example, a physical property value of the shape model is set in the process shown in Step S103 as a physical property parameter intrinsic to a material constituting the structure. In addition, s is the area of the separation face of the meshes formed when the crack leading edge progresses from the position of the initial crack leading edge to the position of a crack leading edge candidate, and is obtained by comparing the position of the initial crack leading edge to the position of the crack leading edge candidate in the shape model. The area of the separation face s may be calculated together when, for example, the crack leading edge candidates are extracted in Step S111.

When the crack progress evaluation function p is defined as $p=(\delta U_e)/(G_c \cdot s)$, a crack can be considered as easily progressing as the value of the crack progress evaluation function p becomes greater. Thus, in the plurality of extracted crack leading edge candidates, a corresponding crack leading edge candidate can be determined to have a high possibility of realization as the value of the crack progress evaluation function p becomes greater. In the present embodiment, however, the crack progress evaluation function is not limited thereto. In the present embodiment, the crack progress evaluation function may be defined as a function with which the magnitude relation between an elastic energy release rate and a total toughness energy can be compared, and may be defined in any form other than the above. For example, the crack progress evaluation function p may be defined as the difference between an elastic energy release rate and a total toughness energy. In addition, when the structure is composed of a single material, for example, crack leading edge candidates are assumed to have substantially the same value of a total toughness energy (the value set in Step S109), and thus, the crack progress evaluation function p may be defined based on an elastic energy release rate. As a method for analyzing presence or absence of a crack and a progressing direction of the crack using the elastic energy release rate when the structure is formed of a single material, various known methods (for example, the method described in JP 2011-204081A above) can be used, and thus detailed description thereof will be omitted.

When the crack progress evaluation functions $p_1$ to $p_m$ for all of the extracted crack leading edge candidates are calculated, the values $p_1$ to $p_m$ are compared to one another, and the maximum value ($p_{max}$) is extracted (Step S117). Here, the reason for extracting the crack progress evaluation function $p_{max}$ that has the maximum value in Step S117 is that a crack is considered to easily occur as the value of the crack progress evaluation function p becomes greater in the present embodiment based on the definitions of an elastic energy release rate, a total toughness energy, and a crack progress evaluation function. In the process shown in Step S117, a crack leading edge candidate that is considered to have the highest possibility of realization based on the crack progress evaluation function may be extracted, and a specific extraction method may be appropriately set according to the definitions of an elastic energy release rate, a total toughness energy, and a crack progress evaluation function. Note that, when only one crack leading edge candidate is extracted in Step S111, the crack leading edge candidate may be extracted as a crack leading edge candidate that has the highest possibility of realization in Step S117.

Next, it is determined whether or not the crack progress evaluation function Amax that is the maximum value is equal to or greater than a predetermined value D (Step S119). Here, the predetermined value D is a threshold value for evaluating whether or not a crack will progress, and in the example shown in FIGS. 3A and 3B, for example, D=1 can be set. As described above, since the crack is expected to progress when the elastic energy release rate is greater than the total toughness energy, when $p_{max}$<D=1, the crack is considered to no longer progress unless the external force factor condition is not changed, for example, more external force or the like is applied, based on the definition of the crack progress evaluation function. Thus, when $p_{max}$<D=1 is determined in Step S119, the series of the crack progress analysis process ends.

On the other hand, when $p_{max}$≥D=1, it indicates that there is a possibility of a crack progressing so as to realize at least a crack leading edge candidate corresponding to the crack progress evaluation function $p_{max}$. Thus, when it is determined that $p_{max}$≥D=1 in Step S119, a crack is regarded as progressing so as to realize a crack leading edge candidate corresponding to the crack progress evaluation function $p_{max}$, and then a process of causing the crack to progress by opening the node and the meshes so as to realize the crack leading edge candidate in the shape model (Step S121). As described above, the process of Step S119 can be said to be a process of determining with respect to a crack leading edge candidate whether or not a crack will progress along the crack leading edge candidate. Note that, in the example shown in FIGS. 3A and 3B, since the crack progress evaluation function p is defined as a ratio of an elastic energy release rate to a total toughness energy, D=1 is set as the threshold value D, however, the threshold value D may be appropriately set according to the definition of the crack progress evaluation function p as a value with which the crack progress can be determined.

Next, by opening the nodes and meshes corresponding to the crack leading edge candidate in Step S121, it is determined whether or not the crack has reached an end of the shape model (Step S123). When the crack has reached the end of the shape model, analysis of the progress of the crack is no longer possible in that direction, and thus the series of the crack progress analysis processes ends. On the other hand, when the crack has not reached the end of the shape model, there is a possibility of the crack still progressing in that direction. Thus, when it is determined that the crack has not reached the end of the shape model in Step S123, a new crack leading edge including the open portion is re-set as a calculation target (Step S125), and the process of Step S111 and the following processes are repeated for all of the nodes adjacent to the new crack leading edge.

Note that, although the case in which the crack leading edge candidate that has the highest possibility of realization is extracted in Step S117, and then it is determined whether or not the crack has progressed along the crack leading edge candidate in Step S119 has been described in the above example, the order of the processes may be reversed in the present embodiment. In other words, first, it may be determined whether or not the crack will progress along a crack leading edge candidate with respect to each of the crack leading edge candidates extracted in Step S111, and then a crack leading edge candidate that has the highest possibility of realization may be extracted from the crack leading edge candidates from which the progress of the crack has been determined to occur. The order of the processes of Steps S117 and S119 may be appropriately set taking a calculation load or the like into account.

In the crack progress analysis method according to the first embodiment, the processes shown in Steps S101 to S125 described above are repeated until there is no crack leading edge candidate serving as a calculation target. There is no crack leading edge candidate when the progress of the crack stops (when it is determined that $p_{max}$<D=1 in Step S119 described above) or when the crack has reached the end of the shape model (when the crack is determined to have reached the end of the shape model in Step S123 described above). The case in which the crack has reached the end of the shape model can also include the case in which the shape model is completely separated due to the progress of the crack. When, however, the external force factor condition is changed even if it is determined that $p_{max}$<D=1 in Step S119 and thus the progress of the crack stops, the distribution of stress in the shape model can change and the value of the elastic energy release rate can also change, and thus the series of processes may repeated.

Hereinabove, the process procedure of the crack progress analysis method according to the first embodiment has been described with reference to FIGS. 3A and 3B. As described above, in the first embodiment, a total toughness energy that is an energy necessary when a crack progresses for one session is set, and a crack leading edge candidate after one session appropriate for the total toughness energy is extracted. Then, for the extracted crack leading edge candidate, the elastic energy release rate $\delta U_e$ and the crack progress evaluation function p are calculated. In the general crack progress analysis method, however, one node is focused on and the progress of the crack at the node is analyzed, and thus the amount of progress of the crack in one session is limited for one mesh. Specifically, with respect to all nodes adjacent to a crack leading edge in the crack progressing direction, the elastic energy release rates $\delta U_e$ are calculated with a heavy calculation load, and a mesh in which a crack progresses most easily is selected based on the calculation result. Thus, in order to calculate the progress of a crack of one session, FEM calculation with respect to all of the nodes adjacent to the crack leading edge is necessary, which results in an increase of the calculation load.

On the other hand, in the first embodiment, the elastic energy release rates $\delta U_e$ are calculated for the crack leading edge candidates as described above, rather than for each of the nodes. Thus, in the first embodiment, the calculation of the elastic energy release rates $\delta U_e$ which targets opening of a plurality of nodes and meshes can be performed. In this manner, by targeting the opening of the plurality of nodes for the calculation in the first embodiment, rather than targeting the opening of each node for the calculation one by one, it is possible to lower the number of calculations of the elastic energy release rates $\delta U_e$, which is accompanied by the FEM calculation having a heavy calculation load, and thereby a calculation load can be reduced. Therefore, it is possible to perform analysis such as the analysis of the three-dimensional crack progress that has been difficult to execute in the past due to a heavy calculation load. In addition, the crack progress analysis method using the elastic energy release rates $\delta U_e$ is a method with high adaptability that can also be applied to, for example, a crack that progresses through different kinds of materials in a structure obtained by combining the different kinds of materials, exfoliation on an interface, and the like, and thus the crack progress analysis with a lighter calculation load is realized while maintaining high adaptability in the first embodiment.

In addition, in the first embodiment, by changing a setting of the total toughness energy, the resolving power of the crack progress analysis can be adjusted. As described above, the total toughness energy set in Step S109 can be said to be a value for deciding the amount of the progress of a crack in one session. Thus, if the total toughness energy is set to a high value, the amount of the progress of the crack in one session relatively increases, and accordingly it is possible to finish the series of crack progress analysis processes for a shorter period of calculation time. On the other hand, if the total toughness energy is set to a low value, the amount of the progress of the crack in one session relatively decreases, and accordingly it is possible to perform the crack progress analysis with strong resolving power and high accuracy. As described above, by changing the setting of the total toughness energy in the present embodiment, the accuracy and the calculation time of a desired result can be appropriately adjusted, and therefore convenience for a user who performs the crack progress analysis can be enhanced.

(2-2. Process of Extracting a Crack Leading Edge Candidate)

The process of extracting a crack leading edge candidate according to the first embodiment shown in Step S111 of FIGS. 3A and 3B will be described in detail. As described above, in the extraction process, a crack leading edge candidate is extracted based on a pre-set total toughness energy, however, at that time, the two conditions which are the condition 1 for continuity of a crack leading edge and the condition 2 for continuity of a crack before and after its progress are considered. Hereinbelow, the two conditions considered in the process of extracting a crack leading edge candidate will be described.

(2-2-1. Condition for Continuity of a Crack Leading Edge)

Figure 4A:
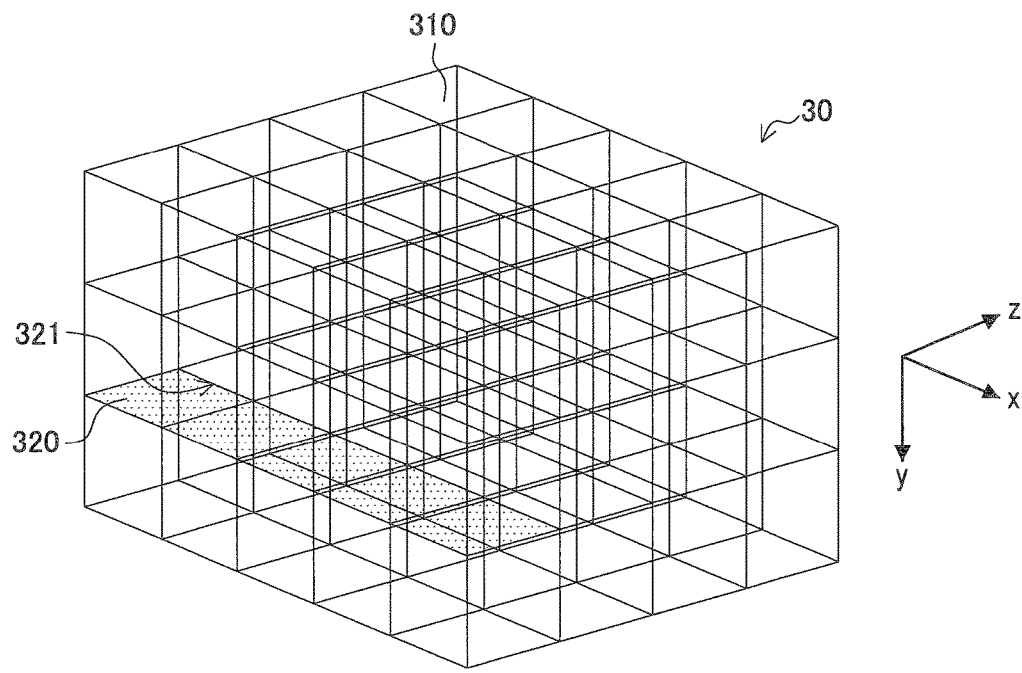
FIG. 4A is a schematic diagram showing a shape model of a structure for describing a condition for continuity of a crack leading edge.
Figure 4B:
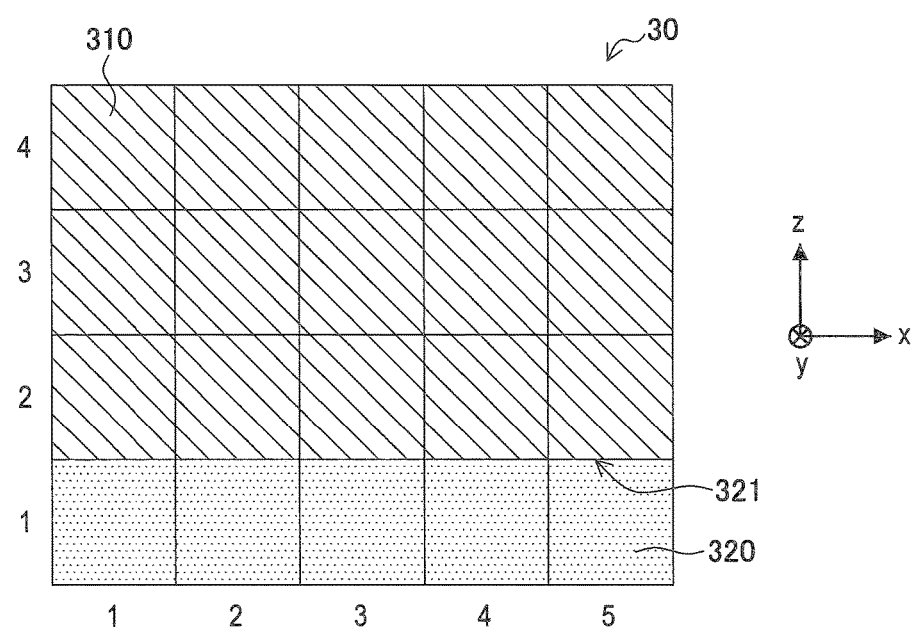
FIG. 4B is a schematic diagram showing a shape model of a structure for describing a condition for continuity of a crack leading edge.
Figure 5A:
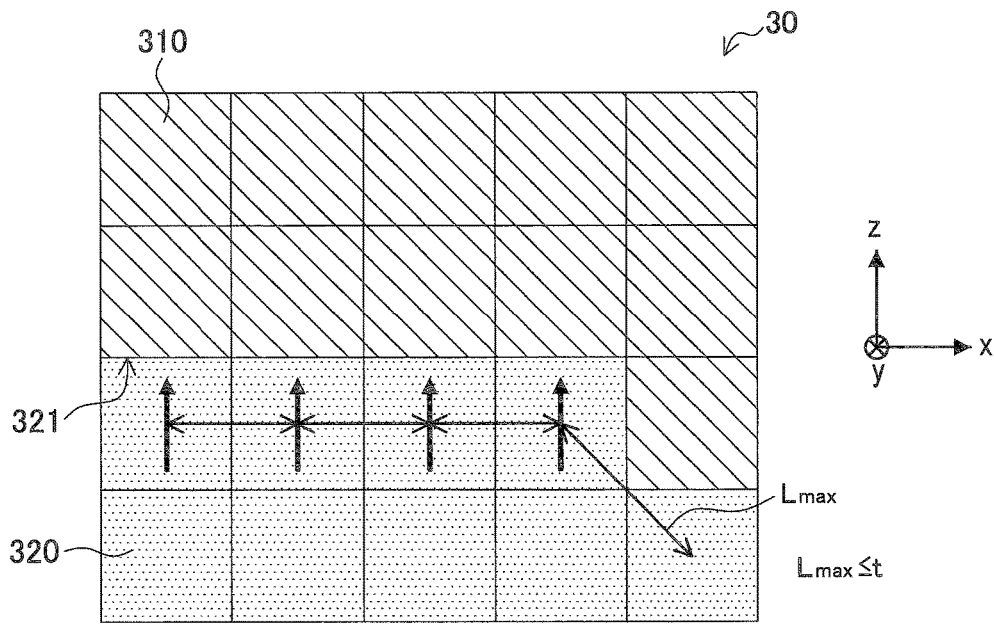
FIG. 5A is a schematic diagram exemplifying a crack leading edge candidate which satisfies the condition for continuity of a crack leading edge in the shape model shown in FIG. 4B.
Figure 5B:
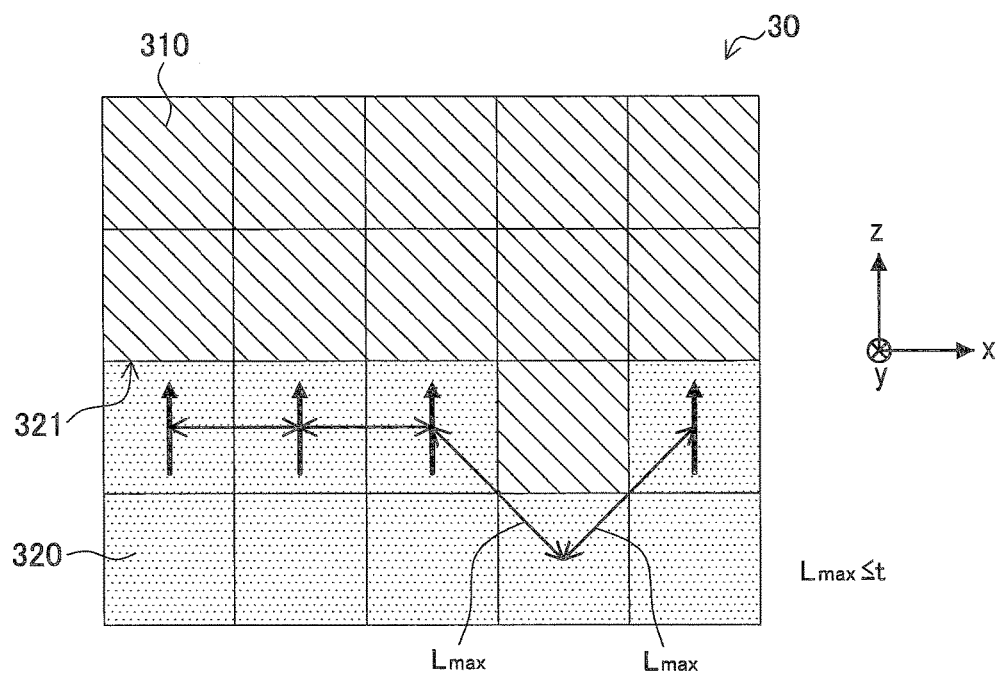
FIG. 5B is a schematic diagram exemplifying a crack leading edge candidate which satisfies the condition for continuity of a crack leading edge in the shape model shown in FIG. 4B.
Figure 5C:
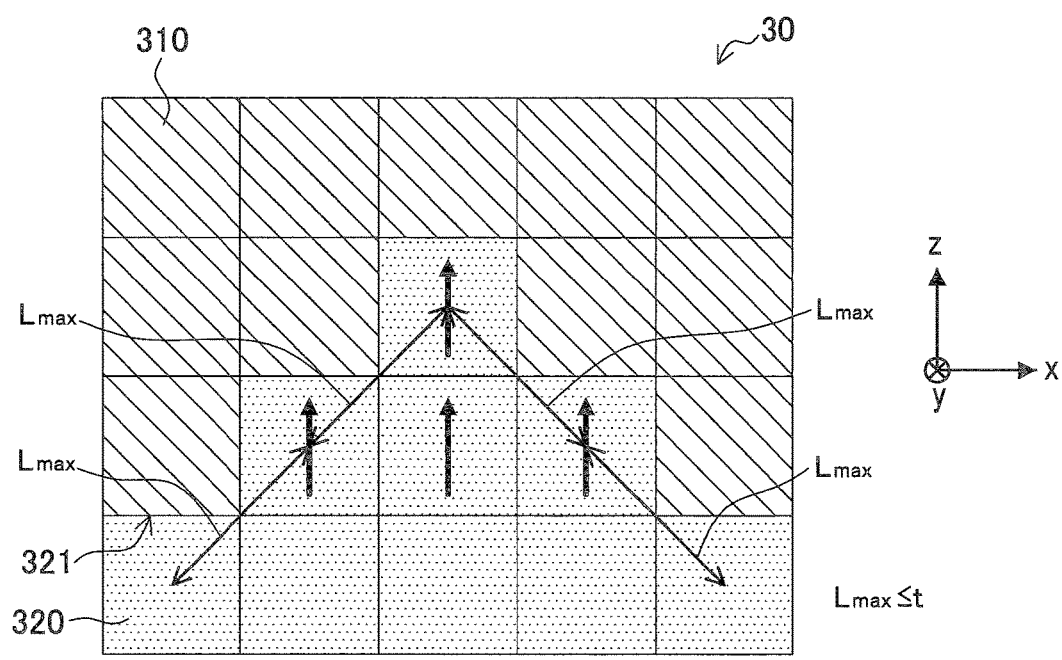
FIG. 5C is a schematic diagram exemplifying a crack leading edge candidate which satisfies the condition for continuity of a crack leading edge in the shape model shown in FIG. 4B.
Figure 6A:
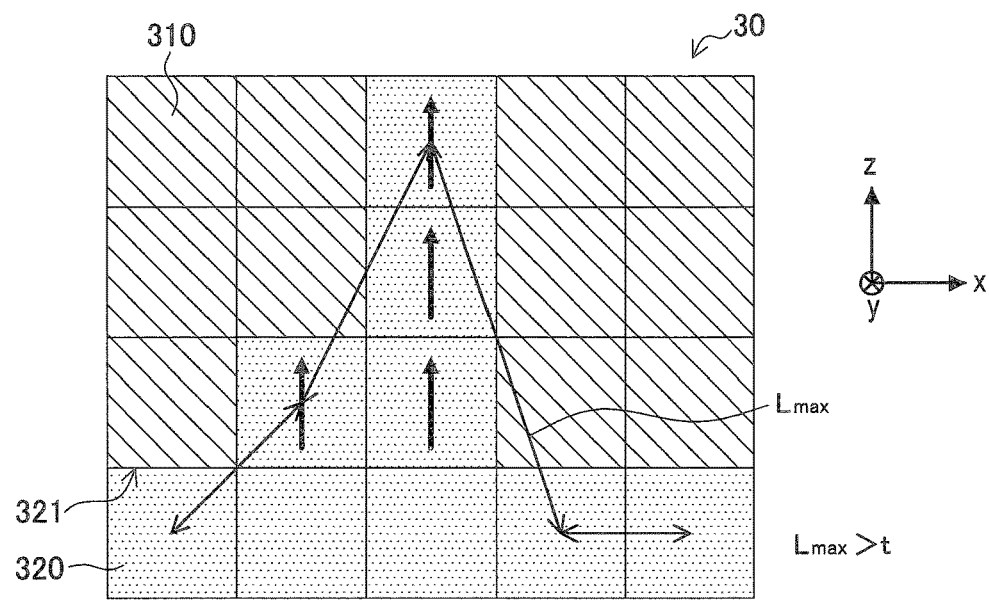
FIG. 6A is a schematic diagram exemplifying the crack leading edge candidate which does not satisfy the condition for continuity of a crack leading edge in the shape model shown in FIG. 4B.
Figure 6B:
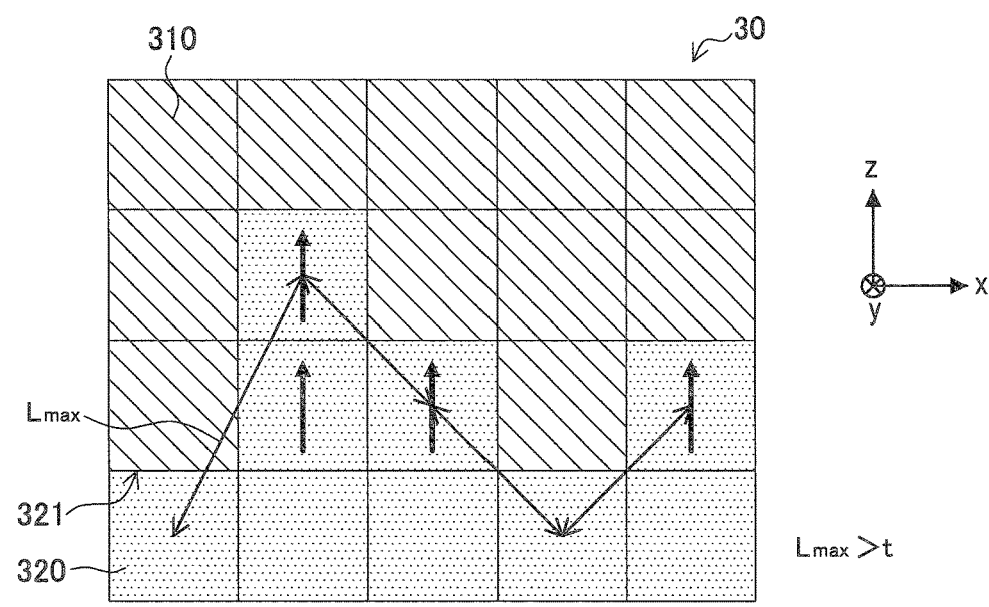
FIG. 6B is a schematic diagram exemplifying the crack leading edge candidate which does not satisfy the condition for continuity of a crack leading edge in the shape model shown in FIG. 4B.
Figure 7:
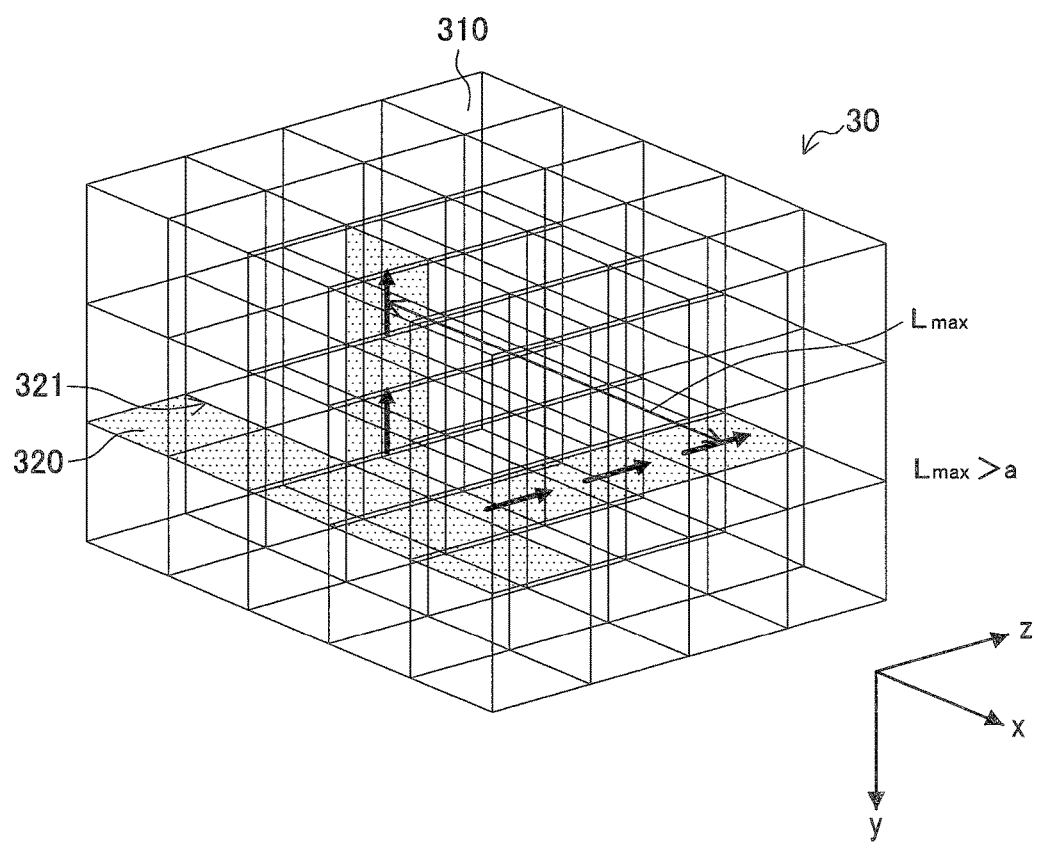
FIG. 7 is a schematic diagram exemplifying the crack leading edge candidate which does not satisfy the condition for continuity of a crack leading edge in the shape model shown in FIG. 4A.

First, continuity of a crack leading edge that is the first condition will be described with reference to FIGS. 4A, 4B, 5A to 5C, 6A, 6B, and 7. FIGS. 4A and 4B are schematic diagrams showing a shape model of a structure for describing the condition for continuity of a crack leading edge. FIGS. 5A to 5C are schematic diagrams exemplifying the crack leading edge candidate that satisfies the condition for continuity of a crack leading edge in the shape model shown in FIG. 4B. FIGS. 6A and 6B are schematic diagrams exemplifying the crack leading edge candidate that does not satisfy the condition for continuity of a crack leading edge in the shape model shown in FIG. 4B. FIG. 7 is a schematic diagram exemplifying the crack leading edge candidate that does not satisfy the condition for continuity of a crack leading edge in the shape model shown in FIG. 4A.

In actual progress of a crack, since it is difficult to think of only a specific portion of a crack leading edge progressing to protrude more than other portions when a crack progresses, the crack leading edge is assumed to be formed to smoothly continue in the progressing direction. Thus, in the first embodiment, taking such continuity of a crack leading edge into account, a crack leading edge candidate is extracted so that the distance between adjacent meshes is equal to or shorter than a predetermined value among a plurality of meshes constituting the crack leading edge after the progress of the crack.

In FIGS. 4A and 4B, a model of a structure for describing the conditions is shown. FIG. 4A is a perspective diagram of the shape model of the structure. Referring to FIG. 4A, the shape model 30 is constituted by a plurality of hexahedral meshes 310 and has a cuboid shape. A crack is occurring in a part of the shape model 30, and in FIG. 4A, a crack face 320 of the crack is illustrated using hatching. The crack face 320 corresponds to the separation face of the meshes 310 separated by the crack. In FIG. 4A, the crack face 320 is assumed to be present in one face of meshes 310 of one row extending in the x-axis direction, that is, the face parallel to the plane regulated by the x axis and the z axis (the x-z plane), for the sake of simplification. In addition, a crack leading edge 321 is present at the end of the crack face 320 in the positive direction of the z axis. In FIG. 4A, the crack leading edge 321 is illustrated by a dashed line.

FIG. 4B is a cross-sectional diagram illustrating when the shape model 30 shown in FIG. 4A is cut in the cross section that includes the crack face 320. The cross section shown in FIG. 4B is the cross section of the x-z plane of the shape model 30, having a rectangular shape in which five meshes and four meshes are arrayed in the x-axis direction and the z-axis direction respectively. Hereinbelow, for the sake of simplification, the conditions will be described exemplifying two-dimensional progress of the crack in the plane shown in FIG. 4B. The first embodiment, however, is not limited thereto, and as will be described with reference to FIG. 7, crack leading edge candidates can be extracted also in consideration of the condition for continuity of a crack leading edge likewise in three-dimensional progress of a crack. In addition, in order to simplify description, each mesh 310 shown in FIG. 4B will be indicated with x-z coordinates. Specifically, as shown in FIG. 4B, among the meshes 310 within the plane, the coordinates of the mesh 310 located in the lowermost and leftmost portion of the drawing are set to (x, z)=(1, 1), and the mesh 310 is also described as a mesh (1, 1). In addition, with the mesh (1, 1) as the starting point, the coordinate of the x axis is assumed to increase in the right direction of the drawing, and the coordinate of the z axis is assumed to increase in the upper direction of the drawing. For example, the coordinates of the mesh 310 located in the uppermost and rightmost portion of the drawing is (x, z)=(5, 4), and the mesh 310 is also described as a mesh (5, 4). Other meshes are also assumed to be described as mesh (x, z) using the values of the x-z coordinates in the same manner. In FIG. 4B, the values of the x-z coordinates corresponding to the position of each mesh are also illustrated.

Referring to FIG. 4B, the surface of the meshes 310 of one row located furthest in the negative direction of the z-axis direction, which are the mesh (1, 1) to the mesh (5, 1), corresponds to the crack face 320. In addition, the crack leading edge 321 is between the mesh (1, 1) to the mesh (5, 1) and the mesh (1, 2) to the mesh (5, 2) in parallel with the x-axis direction.

From the state shown in FIG. 4B, a crack leading edge candidate when the crack progresses in the positive direction of the z axis is considered. As described above, in the first embodiment, a crack leading edge candidate is extracted so that the distance between adjacent meshes among a plurality of meshes constituting the crack leading edge after the progress of the crack is equal to or shorter than the predetermined value, taking continuity of the crack leading edge into account. Specifically, the crack leading edge 321 is hypothetically caused to progress so as to be suitable for the total toughness energy set in the process shown in Step S109 of FIGS. 3A and 3B, and with respect to the meshes 310 constituting the crack leading edge after the progress, the distances between the adjacent meshes 310 are measured. Then, when the maximum value of the distances is equal to or lower than the predetermined threshold value, the crack leading edge can be extracted as a crack leading edge candidate.

First, referring to FIGS. 5A to 5C, the case in which a crack leading edge candidate satisfies the condition for continuity of a crack leading edge will be described. In the example shown in FIG. 5A, the crack face 320 has progressed to the meshes (1, 2), (2, 2), (3, 2), and (4, 2). As the crack face 320 progresses, the crack leading edge 321 also progresses in the positive direction of the z axis. Referring to FIG. 5A, the meshes 310 constituting the crack leading edge 321 after the progress are the meshes (1, 2), (2, 2), (3, 2), (4, 2), and (5, 1). Accordingly, the distances L between the adjacent meshes 310 among the above meshes 310 constituting the crack leading edge 321 are measured. In FIG. 5A, the length corresponding to the distance L is indicated by double-headed arrows (the distances of the adjacent meshes 310 are indicated by double-headed arrows also in FIGS. 5B, 5C, 6A, 6B, and 7 to be described later). In the example shown in FIG. 5A, the maximum value $L_{max}$ of the distances L is the distance between the meshes (4, 2) and (5, 1). Since the distance $L_{max}$ is, for example, equal to or shorter than the predetermined threshold value t, the crack leading edge 321 shown in FIG. 5A can be adopted as a crack leading edge candidate.

In the example shown in FIG. 5B, the crack face 320 has progressed to the meshes (1, 2), (2, 2), (3, 2), and (5, 2). Also in this case, the distances between the adjacent meshes 310 among the meshes 310 constituting the crack leading edge 321 after the progress are measured, and the maximum value of the distances is compared to the predetermined threshold value. Referring to FIG. 5B, the meshes 310 constituting the crack leading edge 321 after the progress are the meshes (1, 2), (2, 2), (3, 2), (4, 1), and (5, 2). Accordingly, the distances L between the adjacent meshes 310 among the above meshes 310 constituting the crack leading edge 321 are measured. In the example shown in FIG. 5B, the maximum values $L_{max}$ of the distances L are the distance between the meshes (3, 2) and (4, 1), and the distance between the meshes (4, 1) and (5, 2). Since the distances $L_{max}$ are, for example, equal to or shorter than the predetermined threshold value t, the crack leading edge 321 shown in FIG. 5B can be adopted as a crack leading edge candidate.

In the example shown in FIG. 5C, the crack face 320 has progressed to the meshes (2, 2), (3, 2), (4, 2), and (3, 3). Also in this case, the distances between the adjacent meshes 310 among the meshes 310 constituting the crack leading edge 321 after the progress are measured, and the maximum value of the distances is compared to the predetermined threshold value likewise. Referring to FIG. 5C, the meshes 310 constituting the crack leading edge 321 after the progress are the meshes (1, 1), (2, 2), (3, 3), (4, 2), and (5, 1). The distances L between the adjacent meshes 310 among the above meshes 310 constituting the crack leading edge 321 are measured. In the example shown in FIG. 5C, the distances between the meshes 310 are equal to each other, and thus the distances between the adjacent meshes 310 are the maximum value $L_{max}$. Since the distances $L_{max}$ are, for example, equal to or shorter than the predetermined threshold value t, the crack leading edge 321 shown in FIG. 5C can be adopted as a crack leading edge candidate.

Next, referring to FIGS. 6A and 6B, the case in which a crack leading edge candidate does not satisfy the condition for continuity of a crack leading edge will be described. In the example shown in FIG. 6A, the crack face 320 has progressed to the meshes (2, 2), (3, 2), (3, 3), and (3, 4). Also in this case, the distances between the adjacent meshes 310 among the meshes 310 constituting the crack leading edge 321 after the progress are measured, and the maximum value of the distances is compared to the predetermined threshold value likewise. Referring to FIG. 6A, the meshes 310 constituting the crack leading edge 321 after the progress are the meshes (1, 1), (2, 2), (3, 4), (4, 1), and (5, 1). Accordingly, the distances L between the adjacent meshes 310 among the above meshes 310 constituting the crack leading edge 321 are measured. In the example shown in FIG. 6A, the maximum value $L_{max}$ of the distances L is the distance between the meshes (3, 4) and (4, 1). Since the distance $L_{max}$ is, for example, longer than the predetermined threshold value t, the crack leading edge 321 shown in FIG. 6A is not adopted as a crack leading edge candidate.

In the example shown in FIG. 6B, the crack face 320 has progressed to the meshes (2, 2), (2, 3), (3, 2), and (5, 2). Also in this case, the distances between the adjacent meshes 310 among the meshes 310 constituting the crack leading edge 321 after the progress are measured, and the maximum value of the distances is compared to the predetermined threshold value. Referring to FIG. 6B, the meshes 310 constituting the crack leading edge 321 after the progress are the meshes (1, 1), (2, 3), (3, 2), (4, 1), and (5, 2). Accordingly, the distances L between the adjacent meshes 310 among the above meshes 310 constituting the crack leading edge 321 are measured. In the example shown in FIG. 6B, the maximum values $L_{max}$ of the distances L are the distance between the meshes (1, 1) and (2, 3). Since the distances $L_{max}$ are, for example, longer than the predetermined threshold value t, the crack leading edge 321 shown in FIG. 6B is not adopted as a crack leading edge candidate.

With regard to the crack leading edge 321 shown in FIGS. 6A and 6B, a part of the crack can be said to progress to protrude in the positive direction of the z axis in comparison to the crack leading edge 321 shown in FIGS. 5A to 5C. By applying the condition for continuity of a crack leading edge in the process of extracting a crack leading edge candidate, it is possible to exclude a crack leading edge candidate having a low possibility of actual occurrence, of which a part of the crack progresses to protrude as shown in, for example, FIGS. 6A and 6B.

Furthermore, referring to FIG. 7, the case in which the condition for continuity of a crack leading edge is applied in the process of extracting a crack leading edge candidate in three-dimensional crack progress analysis will be described. FIG. 7 illustrates the state in which the crack progresses three-dimensionally in the shape model 30 shown in FIG. 4A. In the example shown in FIG. 7, a crack progresses from the initial crack face 320 shown in FIG. 4A in each of the z-axis direction and the y-axis direction, and the progressing crack face 320 is present in a so-called twisted position. Also in this case, the distances between the adjacent meshes 310 among the meshes 310 constituting the crack leading edge 321 after the progress are measured, and the maximum value of the distances is compared to the predetermined threshold value likewise. As shown in the drawing, the maximum value $L_{max}$ of the distances L in this case is of the distance between the meshes 310 located at the ends of the crack face 320 progressing in each of the z-axis direction and the y-axis direction. Since the distance $L_{max}$ is, for example, longer than the predetermined threshold value t, the crack leading edge 321 shown in FIG. 7 is not adopted as a crack leading edge candidate. By applying the condition for continuity of a crack leading edge in the process of extracting a crack leading edge candidate, it is possible to exclude a crack leading edge candidate having a low possibility of actual occurrence of the crack face progressing three-dimensionally in the directions corresponding to the twisted position as shown in, for example, FIG. 7.

(2-2-2. Condition for Continuity of a Crack Before and after Progress)

Figure 8A:
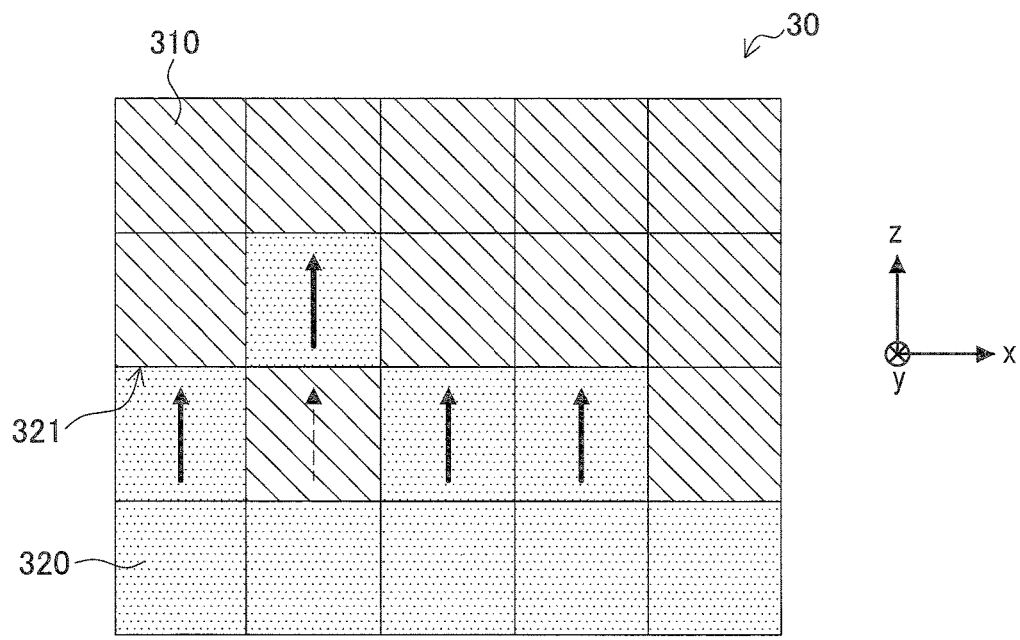
FIG. 8A is a schematic diagram exemplifying the crack leading edge candidate which does not satisfy the condition for continuity of a crack before and after progress in the shape model shown in FIG. 4B.
Figure 8B:
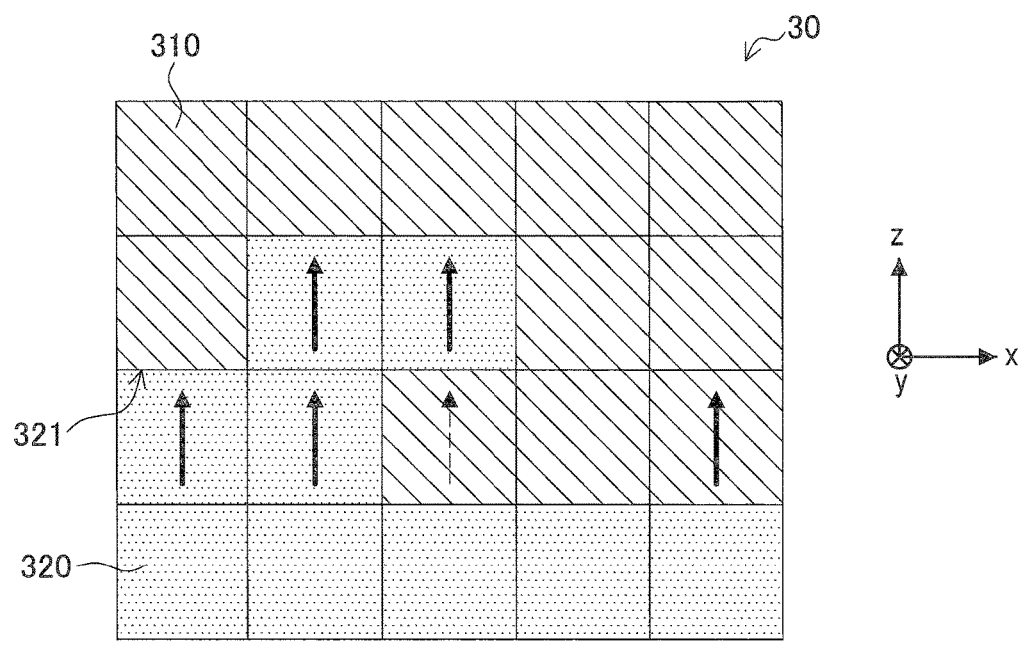
FIG. 8B is a schematic diagram exemplifying the crack leading edge candidate which does not satisfy the condition for continuity of a crack before and after progress in the shape model shown in FIG. 4B.
Figure 9:
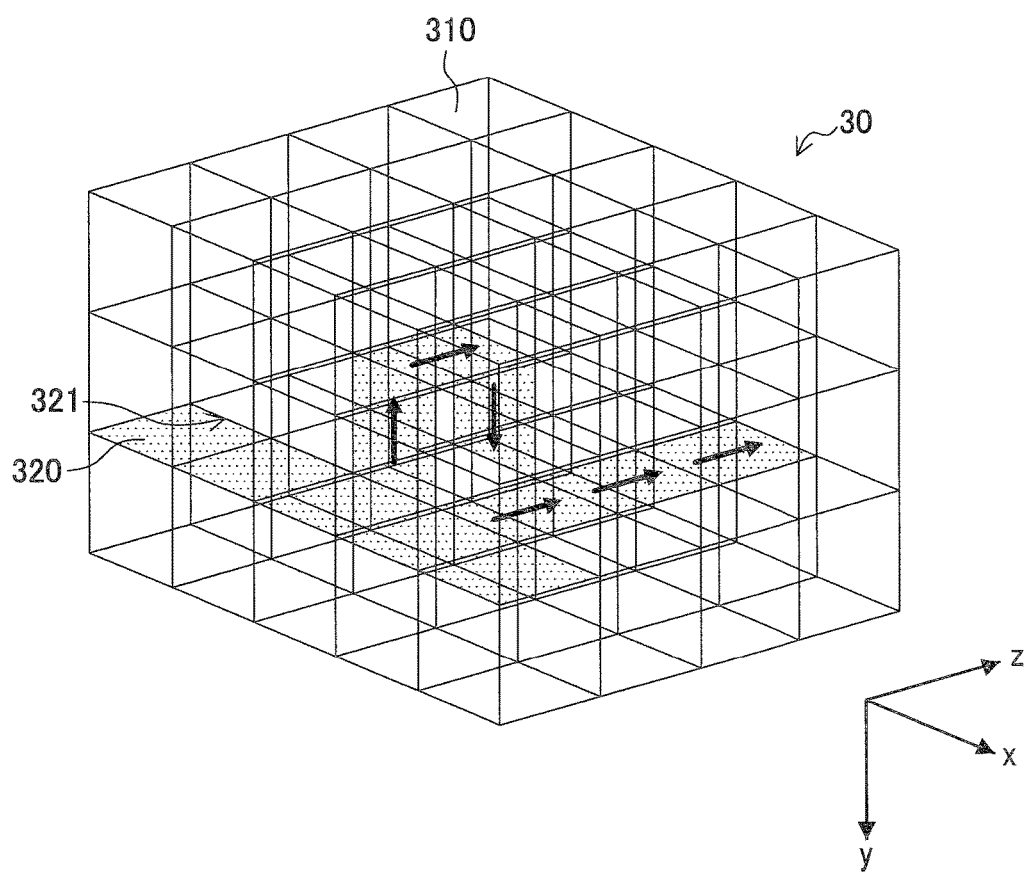
FIG. 9 is a schematic diagram exemplifying the crack leading edge candidate which does not satisfy the condition for continuity of a crack before and after progress in the shape model shown in FIG. 4A.

Next, continuity of a crack before and after progress which is the second condition will be described with reference to FIGS. 8A, 8B, and 9. FIGS. 8A and 8B are schematic diagrams exemplifying a crack leading edge candidate that does not satisfy the condition for continuity of a crack before and after progress in the shape model shown in FIG. 4B. FIG. 9 is a schematic diagram exemplifying the crack leading edge candidate that does not satisfy the condition for continuity of a crack before and after progress in the shape model shown in FIG. 4A.

In actual progress of a crack, it is difficult to think of a region in which a crack does not occur being on the straight line connecting the crack leading edge formed before the progress of the crack and the crack leading edge formed after the progress of the crack in the shape of an isolated field (shape of a floating island), or the crack progressing around three-dimensionally from the viewpoint of stability of energy. Therefore, in consideration of continuity of a crack before and after progress in the first embodiment, in order to prevent the presence of a discontinuous region in a crack progressing direction, in other words, in order to prevent the presence of a region in which meshes are combined within a plane in which the crack leading edge formed before the progress of the crack is connected to the crack leading edge formed after the progress of the crack in the shortest distance, a crack leading edge candidate is extracted.

Note that description with respect to the present condition will be provided with reference to the shape model 30 shown in FIGS. 4A and 4B. Also in the example shown in FIGS. 8A and 8B, the initial crack face 320 is assumed to be present in the meshes 310 of one row located furthest in the negative direction of the z axis, and the crack is assumed to progress in the z-axis direction within the cross section that is horizontal to the x-z plane shown in FIG. 4B. In addition, the position of each mesh 310 within the cross section is assumed to be indicated by (x, z) that is the coordinates of the x and z axes.

With reference to FIGS. 8A and 8B, the case in which the crack leading edge candidate does not satisfy the condition for continuity of a crack before and after progress will be described. In the example shown in FIG. 8A, the crack face 320 has progressed to the meshes (1, 2), (2, 3), (3, 2), and (4, 2). Here, the crack face 320 has not progressed in the mesh (2, 2) (in other words, the meshes 310 are combined in the y-axis direction). In this case, when the meshes 310 located in front of and behind the mesh (2, 2) in the crack progressing direction (z-axis direction) are focused on, the crack face 320 is formed in both of the meshes (2, 1) and (2, 3). Therefore, the mesh (2, 2) is determined to be the meshes 310 that are combined within the plane in which the crack leading edge formed before the progress of the crack is connected to the crack leading edge formed after the progress of the crack in the shortest distance (in other words, the mesh (2, 2) is a discontinuous region in the crack progressing direction), and thus, the crack leading edge 321 shown in FIG. 8A is not adopted as a crack leading edge candidate.

In the example shown in FIG. 8B, the crack face 320 has progressed to the meshes (1, 2), (2, 2), (2, 3), and (3, 3). Here, the crack face 320 has not progressed in the mesh (3, 2) (in other words, the meshes 310 are combined in the y-axis direction). In this case, when the meshes 310 located in front of and behind the mesh (3, 2) in the crack progressing direction (z-axis direction) are focused on, the crack face 320 is formed in both of the meshes (3, 1) and (3, 3). Therefore, the mesh (3, 2) is determined to be the meshes 310 that are combined within the plane in which the crack leading edge formed before the progress of the crack is connected to the crack leading edge formed after the progress of the crack in the shortest distance (in other words, the mesh (3, 2) is a discontinuous region in the crack progressing direction), and thus, the crack leading edge 321 shown in FIG. 8B is not adopted as a crack leading edge candidate.

Furthermore, with reference to FIG. 9, the case in which the condition for continuity of a crack leading edge before and after the progress of the crack is applied to the process of extracting a crack leading edge candidate in analysis of the three-dimensional progress of the crack will be described. FIG. 9 illustrates the state in which the crack progresses three-dimensionally in the shape model 30 shown in FIG. 4A. In the example shown in FIG. 9, the crack progresses from the initial crack face 320 shown in FIG. 4A in the z-axis direction and the y-axis direction. In addition, the crack progressing in the negative direction of the y axis changes its progress direction to the reverse direction halfway and then goes around to progress in the positive direction of the y axis. Also in this case, it is determined whether or not there are meshes 310 combining within the plane in which the crack leading edge formed before the progress of the crack is connected to the crack leading edge formed after the progress of the crack in the shortest distance (in other words, whether or not there is a discontinuous region in the crack progressing direction), and accordingly, the crack leading edge 321 shown in FIG. 9 is not adopted as a crack leading edge candidate.

As described above, by applying the condition for continuity of a crack before and after progress in the process of extracting a crack leading edge candidate, it is possible to exclude a crack leading edge candidate having a low possibility of actual occurrence when a non-crack face is present in the shape of an isolated field as exemplified in FIGS. 8A and 8B, or when the crack progresses as if it goes around a predetermined region three-dimensionally as exemplified in FIG. 9.

Hereinabove, the two conditions which are the condition for continuity of a crack leading edge and the condition for continuity of a crack before and after progress considered in the process of extracting a crack leading edge candidate according to the first embodiment have been described with reference to FIGS. 4A, 4B, 5A to 5C, 6A, 6B, 7, 8A, 8B, and 9. A crack leading edge which is closest to the actual crack progress phenomenon is extracted as a crack leading edge candidate in consideration of the conditions, and therefore the accuracy in the analysis of the progress of a crack can be enhanced.

Note that the two conditions described above are definitions with respect to the process of extracting a crack leading edge candidate in one session, and do not prohibit occurrence of a crack of which a part protrudes or a crack having strong discontinuity as a result of a plurality of sessions of the crack progress analysis in the first embodiment. Therefore, by securing a predetermined degree of freedom in the shape of a crack after the crack progresses a plurality of sessions, adaptability of a micro level can be maintained in the crack progress analysis according to the first embodiment.

(2-3. Comparison of Calculation Loads)

Next, the calculation load of the general crack progress analysis method described with reference to FIGS. 1A and 1B and the calculation load of the crack progress analysis method according to the first embodiment described with reference to FIGS. 3A and 3B will be compared to each other. Herein, the difference between the calculation loads will be described exemplifying the case in which the progress of a crack is analyzed in a shape model having a simple structure for the sake of simplification.

Figure 10A:
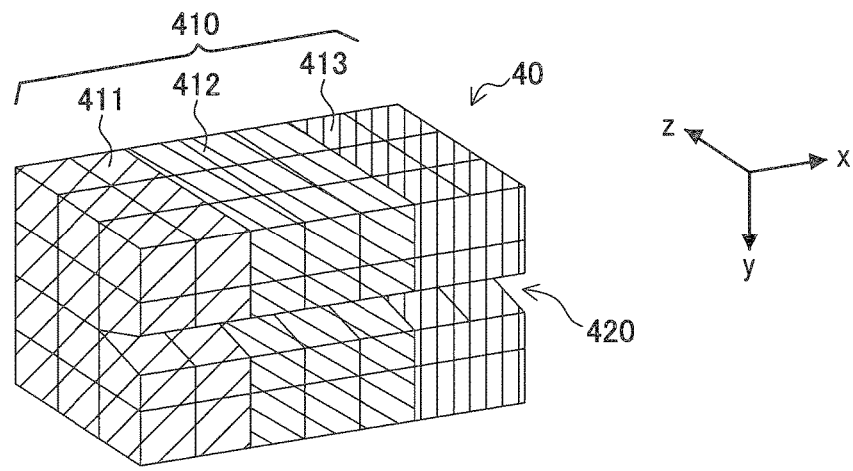
FIG. 10A is a diagram showing a shape model used in describing comparison of calculation loads.
Figure 10B:
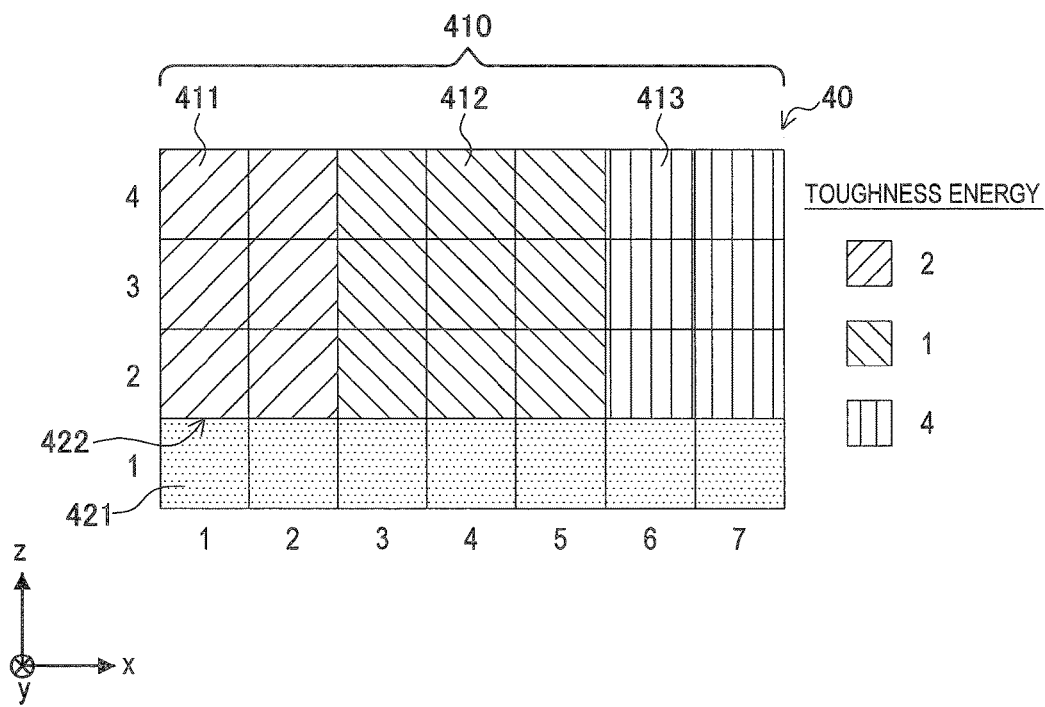
FIG. 10B is a diagram showing a shape model used in describing comparison of calculation loads.

The shape model used in describing the comparison of the calculation loads will be described with reference to FIGS. 10A and 10B. FIGS. 10A and 10B are diagrams showing the shape model used in describing the comparison of the calculation loads.

FIG. 10A is a perspective diagram showing the appearance of the shape model. Referring to FIG. 10A, the shape model 40 is constituted by a plurality of meshes 410 in cubic shapes, thereby forming a cuboid shape. A crack 420 that has a crack face that is substantially parallel to the x-z plane is formed on one face orthogonal to the z axis of the shape model 40. The crack 420 expresses an initial crack formed when the analysis of the progress of the crack is performed.

FIG. 10B is a cross-sectional diagram obtained when the shape model 40 shown in FIG. 10A is cut in the cross section that includes the crack 420. The cross section shown in FIG. 10B is a cross section on the x-z plane of the shape model 40, having a rectangular shape in which seven meshes 410 and four meshes 410 are arrayed in the x-axis direction and the z-axis direction respectively. For the sake of simplification in the shape model 40, the difference of the calculation loads will be described exemplifying the two-dimensional progress of the crack within the plane shown in FIG. 10B.

Here, as a position within the plane of the meshes 310 is expressed by x-z coordinates in FIG. 4B, a position within the plane of the meshes 410 is also expressed by x-z coordinates in FIG. 10B. Specifically, among the meshes 410 within the plane, the coordinates of the mesh 410 located in the lowermost and leftmost portion of the drawing are (x, z)=(1, 1) as shown in FIG. 10B, and the mesh 410 is also described as a mesh (1, 1). In addition, with the mesh (1, 1) as a starting point, the coordinate of the x axis is assumed to increase in the right direction in the drawing and the coordinate of z axis is assumed to increase in the upper direction of the drawing. For example, the coordinates of the mesh 410 located in the uppermost-rightmost portion of the drawing are (x, z)=(7, 4), and the mesh 410 is also described as a mesh (7, 4). Likewise, other meshes are set to be described as mesh (x, z) using the values of the x-z coordinates. In FIG. 10B, the values of the x-z coordinates corresponding to each position of the meshes are also illustrated.

Referring to FIG. 10B, the surface of the meshes 410 of one row located furthest in the negative direction of the z-axis direction, which are the mesh (1, 1) to the mesh (7, 1), corresponds to the crack face 421 of the crack 420. In addition, the crack leading edge 422 of the crack 420 is between the mesh (1, 1) to the mesh (7, 1) and the mesh (1, 2) to the mesh (7, 2) in parallel with the x-axis direction.

Here, the shape model 40 is composed of a plurality of different kinds of materials. Specifically, the meshes 410 constituting the shape model 40 include three different kinds of meshes 411, 412, and 413. The three kinds of meshes 411, 412, and 413 indicate different kinds of materials each having a different toughness value. In FIGS. 10A and 10B, the three kinds of meshes 411, 412, and 413 are illustrated by giving different kinds of hatching. As shown in FIGS. 10A and 10B, the shape model 40 is constituted by the two rows of meshes 411 of which the coordinates of the x axis are "1" and "2," the three rows of meshes 412 of which the coordinates of the x axis are "3," "4," and "5," and the two rows of meshes 413 of which the coordinates of the x axis are "6" and "7."

Toughness values of the meshes 411, 412, and 413 can be set in, for example, the process of Step S603 of the general crack progress analysis method shown in FIG. 1A, or the process of Step S103 of the crack progress analysis method according to the first embodiment shown in FIG. 3A. Here, for the sake of simplification, the toughness values of the meshes 411, 412, and 413 are set to simple integral values. Specifically, the toughness value of each mesh 411 is set to "2," the toughness value of each mesh 412 is set to "1," and the toughness value of each mesh 413 is set to "4." Although the toughness values of the meshes 410 can actually be set as toughness values per unit area, they are assumed herein to be set as toughness values necessary for separating one pair of meshes 411, 412, or 413 coming into contact with each other for the sake of simplification.

(2-3-1. Calculation Load in the General Crack Progress Analysis Method)

Figure 11A:
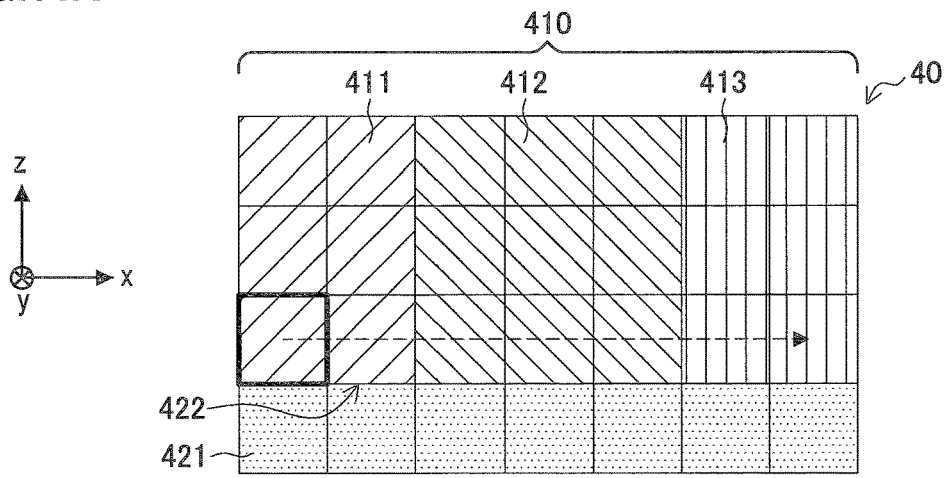
FIG. 11A is an illustrative diagram for describing a calculation load in the general crack progress analysis method.
Figure 11B:
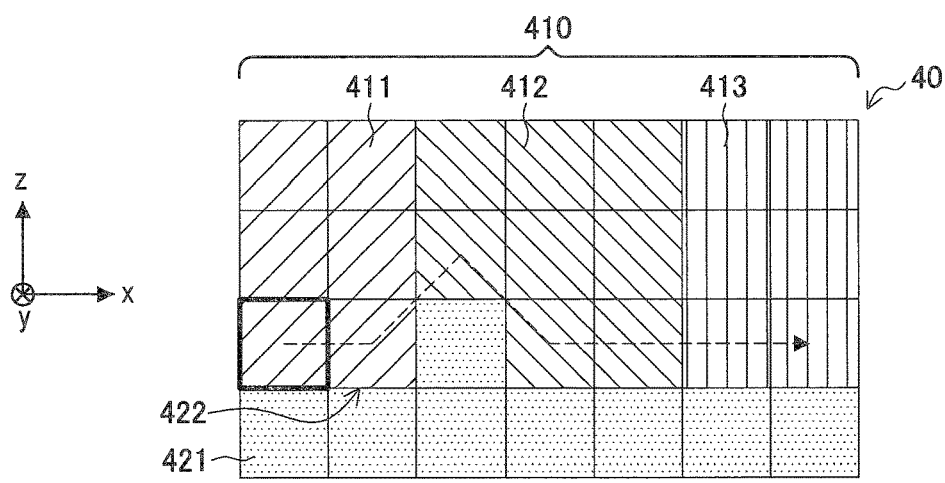
FIG. 11B is an illustrative diagram for describing a calculation load in the general crack progress analysis method.
Figure 11C:
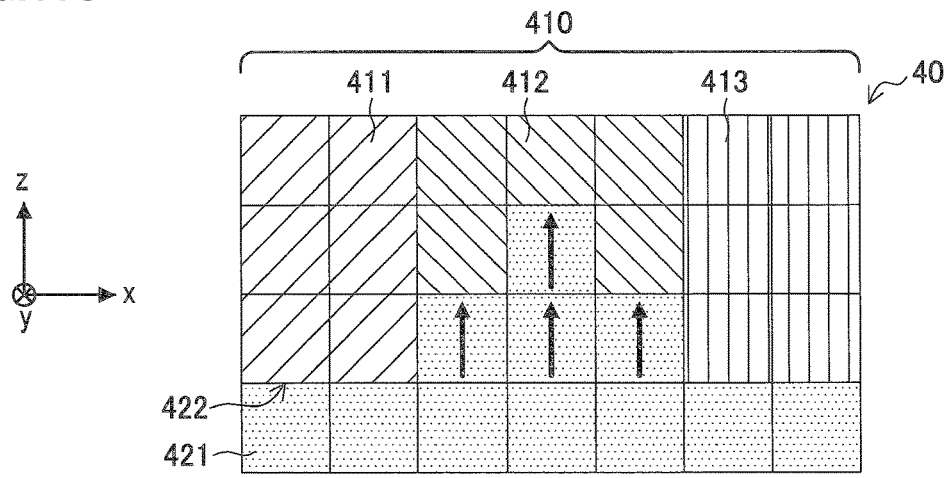
FIG. 11C is an illustrative diagram for describing a calculation load in the general crack progress analysis method.

First, with reference to FIGS. 11A to 11C, the case in which the progress of the crack in the cross section of the shape model 40 shown in FIG. 10B is analyzed based on the process flow of the general crack progress analysis method shown in FIGS. 1A and 1B will be described. FIGS. 11A to 11C are illustrative diagrams for describing a calculation load in the general crack progress analysis method. FIGS. 11A to 11C show the same cross section as that shown in FIG. 10B, illustrating the state in which the crack is progressing in the cross section. Note that, as described in (1-1. Process procedure of a general crack progress analysis method) above, for the calculation load of the general crack progress analysis method, a calculation load in calculation of an elastic energy release rate using the FEM is dominant. Thus, herein, the difference of the calculation loads will be described, focusing on the calculation of an elastic energy release rate using the FEM.

As described in (1-1. Process procedure of a general crack progress analysis method) above, an elastic energy release rate for each node adjacent to a crack leading edge in a crack progressing direction is calculated in the general crack progress analysis method. Thus, when the progress of a crack of one session is analyzed as having a crack leading edge 422 shown in FIG. 10B as an initial crack leading edge, the elastic energy release rate when the meshes 410 including the meshes (1, 2) to (7, 2) are separated in the y-axis direction (in other words, when the crack progresses in the meshes (1, 2) to (7, 2)) as shown in FIG. 11A are calculated. In FIG. 11A, the contour of the mesh 410 that is a calculation target of the elastic energy release rate is illustrated using a thick line, and the dashed-lined arrow showing sequential calculation is illustrated along the crack leading edge 422. In this manner, in the general crack progress analysis method, a total of seven FEM calculations are performed on the seven meshes (1, 2) to (7, 2) coming into contact with the crack leading edge 422 in the first session.

As a result of calculating crack progress evaluation functions p of the meshes (1, 2) to (7, 2) shown in FIG. 11A, the value of the crack progress evaluation function p of the mesh (3, 2), for example, is set to be the largest. In this case, crack progress analysis of a second session is performed with respect to the new crack leading edge 422 that causes the crack to progress in the mesh (3, 2). The shape model 40 of the second session is shown in FIG. 11B. In the second session, elastic energy release rates are calculated for all of the nodes adjacent to the new crack leading edge 422 in the crack progressing direction. Thus, in the second session, a total of seven FEM calculations are performed on the seven meshes (1, 2), (2, 2), (3, 3), (4, 2), (5, 2), (6, 2), and (7, 2) adjacent to the crack leading edge 422.

Then, in the same manner, renewal of the crack leading edge and the calculation of the elastic energy release rate for the nodes adjacent to the renewed crack leading edge in the crack progress direction are repeated. For example, the state of the crack leading edge 422 when a fourth session ends is shown in FIG. 11C. As shown in FIG. 11C, the crack has progressed to four more meshes 410 from the initial crack leading edge 422 shown in FIG. 11A in the stage in which the fourth session ends. As described above, since the calculation of the elastic energy release rate is performed seven times for the seven meshes 410 adjacent to the crack leading edge 422 in one session in the general crack progress analysis method, a total of 28 FEM calculations are expected for causing the crack to progress from the state shown in FIG. 11A to the state shown in FIG. 11C.

(2-3-2. Calculation Load in the Crack Progress Analysis Method According to the First Embodiment)

Next, with reference to FIGS. 12A to 12E, the case in which the progress of the crack in the cross section of the shape model 40 shown in FIG. 10B is analyzed using the process flow of the crack progress analysis method according to the first embodiment shown in FIGS. 3A and 3B will be described. FIGS. 12A to 12E are illustrative diagrams for describing a calculation load in the crack progress analysis method according to the first embodiment. FIGS. 12A to 12E show the same cross section as that shown in FIG. 10B, illustrating the state in which the crack is progressing in the cross section.

As described in (2-1. Process procedure of a crack progress analysis method according to the first embodiment) described above, a crack leading edge candidate appropriate for a set total toughness energy is extracted and an elastic energy release rate using the FEM is calculated on the extracted crack leading edge candidate in the crack progress analysis method according to the first embodiment. Herein, in the process of Step S109 shown in FIG. 3A, for example, the total toughness energy is assumed to be set to "4." In this case, in the crack progress analysis method according to the first embodiment, after taking the two conditions (the condition for continuity of a crack leading edge and the condition for continuity of a crack before and after progress) described above into account, the crack leading edge candidate that is likely to have the total toughness energy of "4" is extracted in Step S111. The process of extracting a crack leading edge based on the two conditions has been described in (2-2. Process of extracting a crack leading edge candidate), and thus detailed description thereof will be omitted.

Figure 12A:
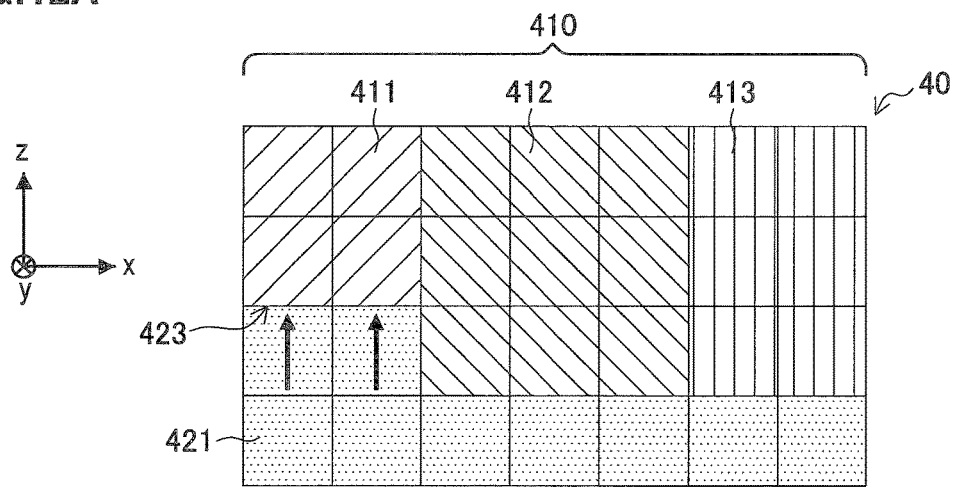
FIG. 12A is an illustrative diagram for describing a calculation load in the crack progress analysis method according to the first embodiment.
Figure 12B:
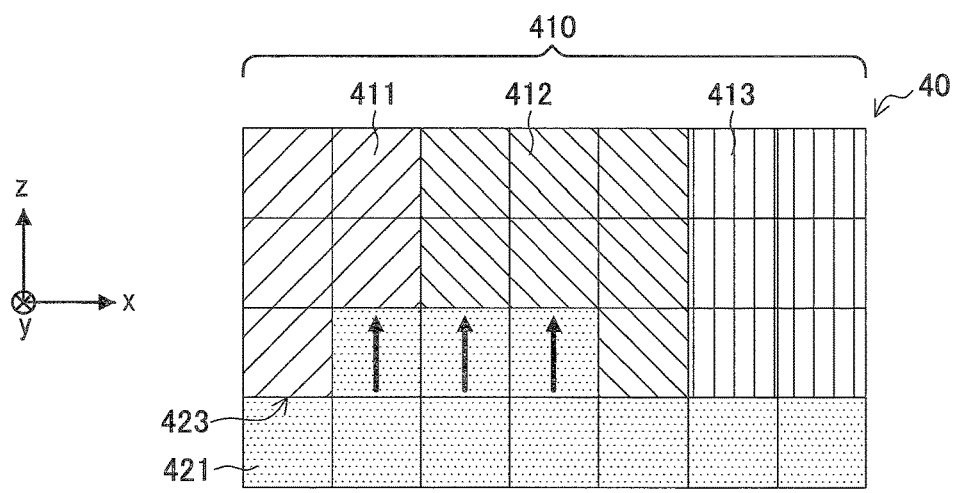
FIG. 12B is an illustrative diagram for describing a calculation load in the crack progress analysis method according to the first embodiment.
Figure 12C:
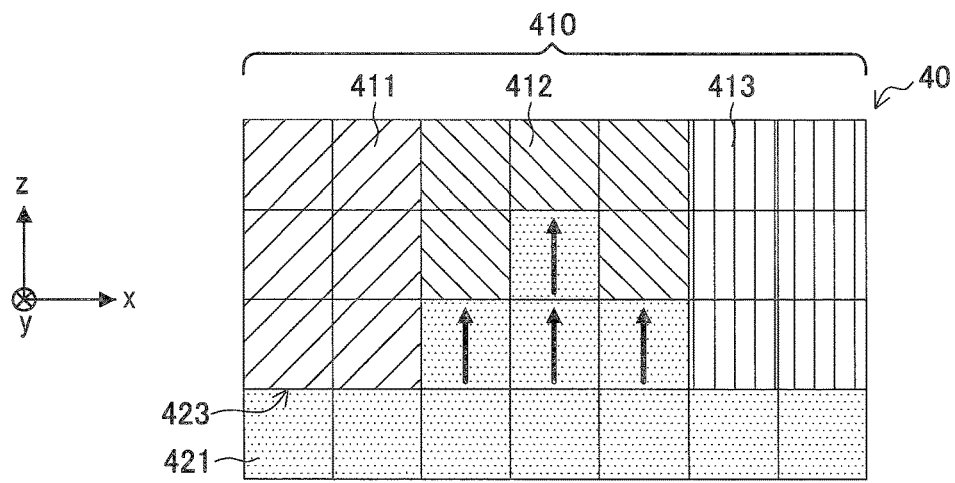
FIG. 12C is an illustrative diagram for describing a calculation load in the crack progress analysis method according to the first embodiment.
Figure 12D:
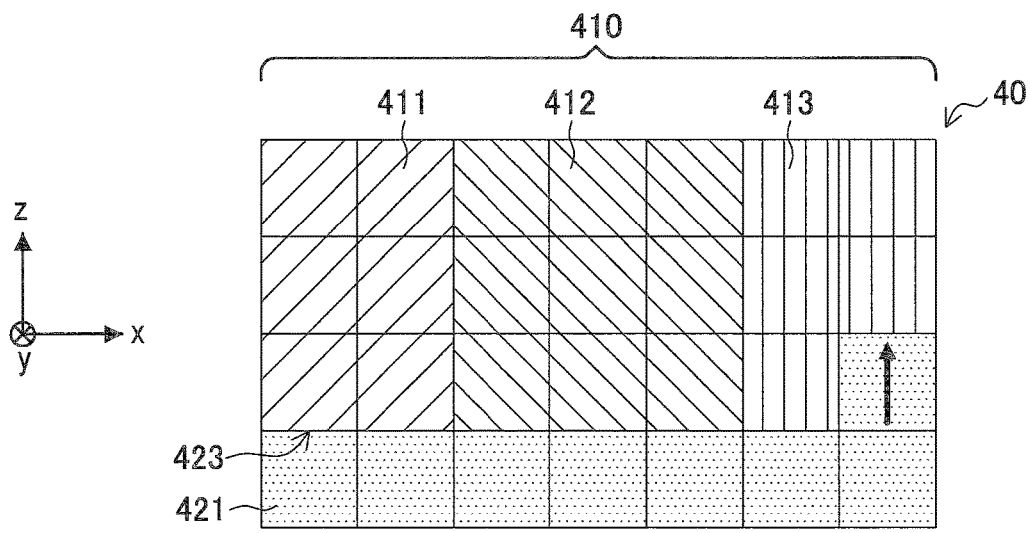
FIG. 12D is an illustrative diagram for describing a calculation load in the crack progress analysis method according to the first embodiment.
Figure 12E:
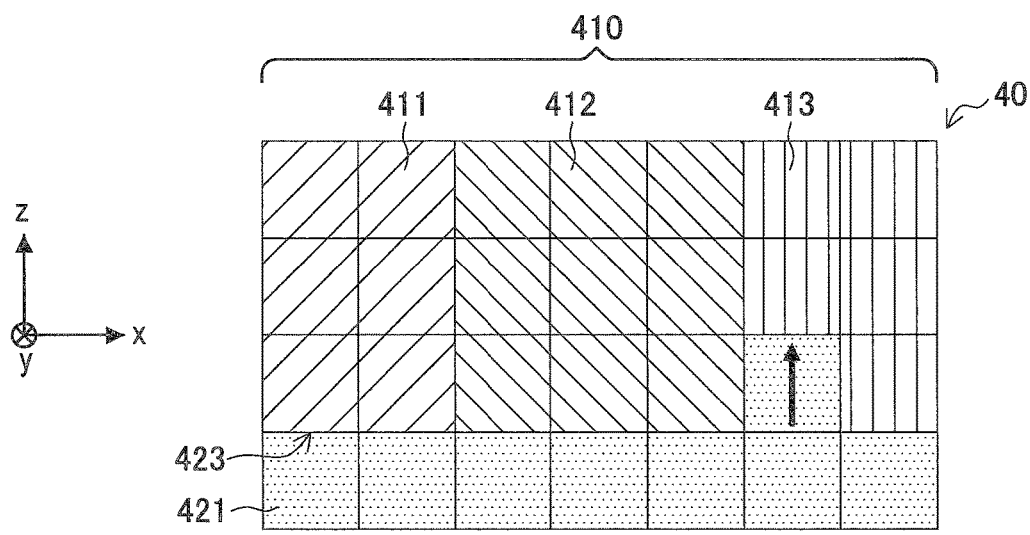
FIG. 12E is an illustrative diagram for describing a calculation load in the crack progress analysis method according to the first embodiment.

When a crack leading edge candidate is extracted having the crack leading edge 422 shown in FIG. 10B as the initial crack leading edge, for example, a crack leading edge candidate shown in FIGS. 12A to 12E can be extracted. FIGS. 12A to 12E show the crack leading edge candidate 423 that can be extracted in a first session in the crack progress analysis method according to the first embodiment. The crack leading edge candidate 423 shown in FIG. 12A is formed such that a crack face 421 progresses from the initial crack leading edge 422 shown in FIG. 10B to portions corresponding to the meshes (1, 2) and (2, 2) of which the set toughness value is "2." The crack leading edge candidate 423 shown in FIG. 12B is formed such that the crack face 421 progresses from the initial crack leading edge 422 shown in FIG. 10B to portions corresponding to the mesh (2, 2) of which the set toughness value is "2," and the meshes (3, 2) and (4, 2) of which the set toughness value is "1." The crack leading edge candidate 423 shown in FIG. 12C is formed such that the crack face 421 progresses from the initial crack leading edge 422 shown in FIG. 10B to portions corresponding to the meshes (3, 2), (4, 2), (5, 2), and (4, 3) of which the set toughness value is "1." The crack leading edge candidate 423 shown in FIG. 12D is formed such that the crack face 421 progresses from the initial crack leading edge 422 shown in FIG. 10B to a portion corresponding to the mesh (7, 2) of which the set toughness value is "4." The crack leading edge candidate 423 shown in FIG. 12E is formed such that the crack face 421 progresses from the initial crack leading edge 422 shown in FIG. 10B to a portion corresponding to the mesh (6, 2) of which the set toughness value is "4."

Thus, the crack leading edge candidate 423 shown in FIGS. 12A to 12E is extracted such that the sum of the toughness energies (i.e., the total toughness energy) for separating the meshes 410 selected when the crack progresses from the initial crack leading edge 422 shown in FIG. 10B to the crack leading edge candidate 423 of each drawing in the y-axis direction is "4" that is the set value of the total toughness energy. To be specific, the crack leading edge candidate 423 can be extracted such that, with respect to the meshes 410 which come in contact with the initial crack leading edge 422 and are located in the crack progressing direction, combinations of the meshes 410 of which the total toughness energy at the time of separation is the set value of "4" are extracted in a round-robin manner after taking the two conditions described above into account. Although the crack progressing in the two-dimensional direction has been shown for the sake of simplification in the examples shown in FIGS. 12A to 12E, the crack leading edge candidate 423 can be extracted in the same manner for a crack progressing in a three-dimensional direction by extracting combinations of the meshes 410 of which the total toughness energy at the time of separation is the set value in a round-robin manner after taking the two conditions described above into account.

In the first embodiment, when the crack leading edge progresses for one session, the elastic energy release rates of each of the five crack leading edge candidates 423 of FIGS. 12A to 12E are calculated using the FEM. Then, the crack progress evaluation functions p of each of the crack leading edge candidates 423 are calculated, the crack progress evaluation functions p are compared to each other, and thereby the crack leading edge 422 one session later is decided. Here, among the crack leading edge candidates 423 of FIGS. 12A to 12E, for example, the crack leading edge candidates 423 shown in FIG. 12C are decided as the crack leading edge 422 one session later. In the crack progress analysis method according to the present embodiment, the crack face 421 can progress from the state shown in FIG. 10B to the state shown in FIG. 12C in one session, and the number of FEM calculations necessary at that time is only five for each crack leading edge candidate 423.

Here, the crack face 421 shown in FIG. 12C has the same shape as the crack face 421 four sessions later in the general crack progress analysis method shown in FIG. 11C. As described above, in order to cause the crack face 421 to progress to the state shown in FIG. 11C, four sessions are necessary, and thus a total of 28 FEM calculations are necessary in the general crack progress analysis method. In the first embodiment, however, in order to cause the crack face 421 to progress to the state shown in FIG. 12C which has the same shape, a total of five FEM calculations are enough in one session. As such, in the first embodiment, by extracting crack leading edge candidates and calculating the crack progress evaluation function with respect to the extracted crack leading edge candidates, it is possible to drastically lower the calculation time in comparison to the general method. Thus, while performing the analysis method having high adaptability using the elastic energy release rate, the calculation load can be further lowered in the first embodiment.

3. Second Embodiment

Figure 13A:
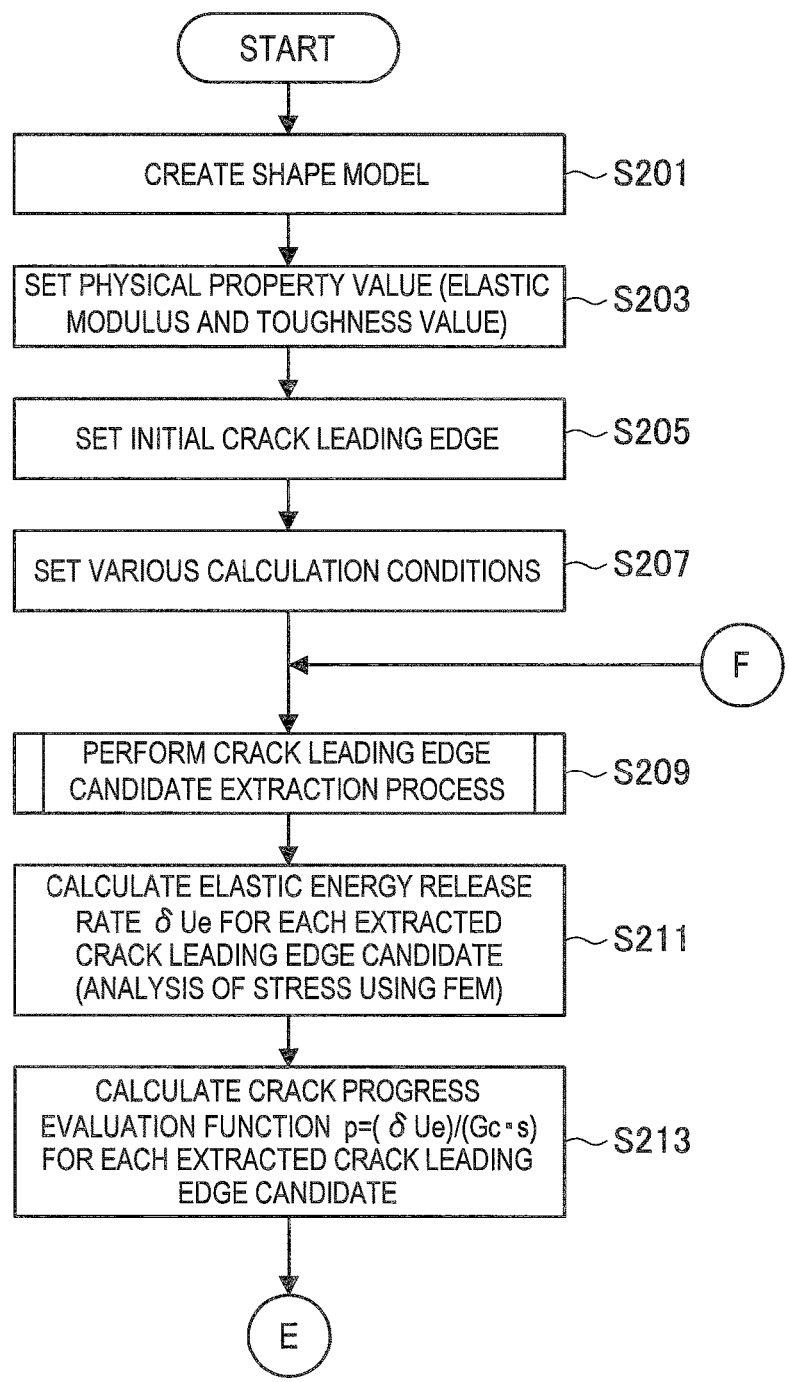
FIG. 13A is a flowchart showing a process procedure of a crack progress analysis method according to a second embodiment.
Figure 13B:
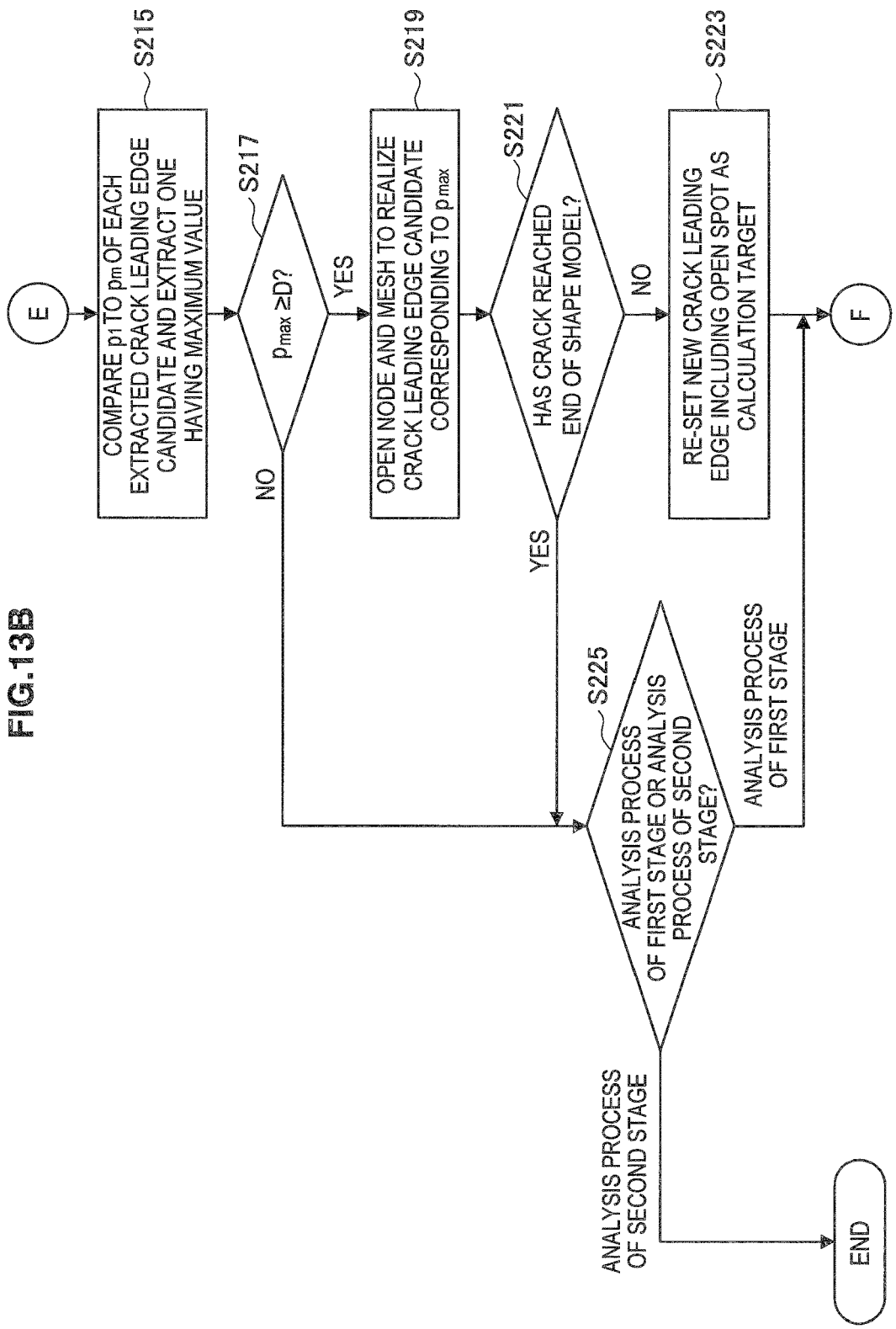
FIG. 13B is a flowchart showing a process procedure of the crack progress analysis method according to a second embodiment.
Figure 14:
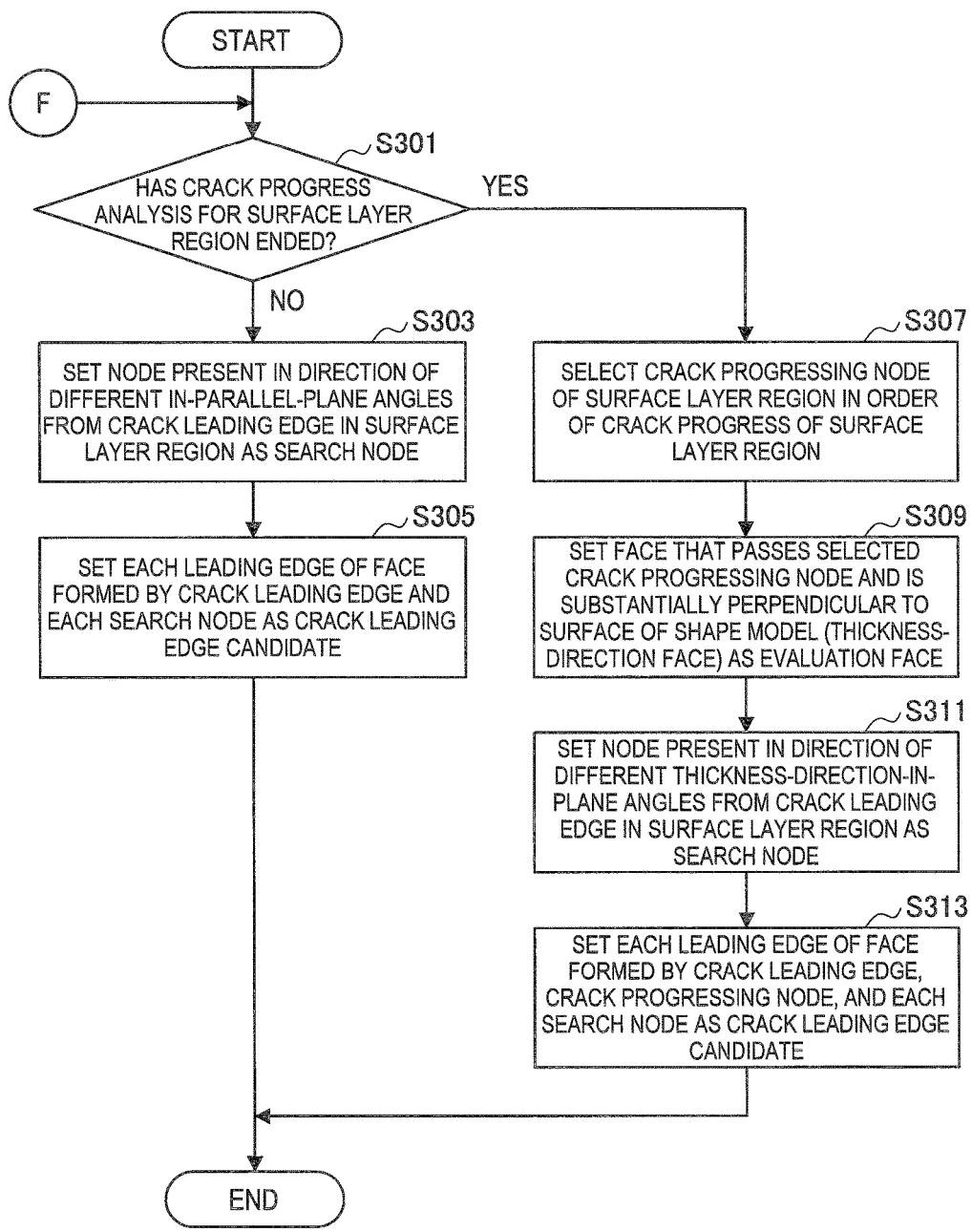
FIG. 14 is a flowchart showing a process procedure of the crack leading edge candidate extraction process (S209) shown in FIG. 13A.

The process procedure of a crack progress analysis method (or an information processing method) according to the second embodiment of the present disclosure will be described with reference to FIGS. 13A, 13B, and 14. FIGS. 13A and 13B are a flowchart showing the process procedure of the crack progress analysis method according to the second embodiment. FIG. 14 is a flowchart showing the process procedure of the crack leading edge candidate extraction process (S209) shown in FIG. 13A. Note that the processes of each of the steps shown in FIGS. 13A, 13B, and 14 can be executed by a processor of various kinds of information processing apparatuses, for example, a PC, a workstation, and the like by performing operations according to a predetermined program.

Herein, in the crack progress analysis method according to the second embodiment, a process of extracting crack leading edge candidates is different from that of the first embodiment. In addition, in the crack progress analysis method according to the second embodiment, the crack progress analysis process is executed in two stages. In other words, first as an analysis process of a first stage, progress of a crack in a surface layer region of a structure is analyzed. Next, as an analysis process of a second stage, the progress of the crack in an internal region of the structure is analyzed based on the progress of the crack in the surface layer region. Here, the surface layer region refers to a surface of the structure, or a layer present at a predetermined depth from the surface including the surface (which will also be referred to hereinafter as a surface layer). In addition, the internal region refers to a region inside the structure which is a region at a predetermined depth coming into contact with the surface layer region in which the progress of the crack is analyzed in the analysis process of the first stage. Since the process procedure of the crack progress analysis method according to the second embodiment is the same as that of the first embodiment described above except for the above point, the differences of the second embodiment from the first embodiment will be mainly described hereinbelow, and overlapping detailed description will be omitted.

Referring to FIGS. 13A and 13B, first a shape model indicating a structure to be analyzed is created using the crack progress analysis method according to the second embodiment (Step S201). Next, for the shape model created in Step S201, various physical property values of materials of the structure are set (Step S203), and then an initial crack leading edge is set (Step S205). Further, various calculation conditions for analyzing progress of a crack are set (Step S207). Since the processes shown in Steps S201 to S207 are substantially the same as the processes shown in Steps S101 to S107 of the crack progress analysis method according to the first embodiment shown in FIG. 3A, detailed description thereof will be omitted. In the second embodiment, however, in addition to formation of meshes, setting of an external force factor condition, setting of an arithmetic operation formula of an elastic energy release rate, setting of a definition formula of a crack progress evaluation function, and setting of the threshold value D to be compared to the crack progress evaluation function, a range of change (amplitude) of an angle r formed within a plane parallel to a surface (which will also be referred to hereinafter as an in-parallel-plane angle r) and an angle u formed within a plane perpendicular to a surface (which will also be referred to hereinafter as a thickness-direction-in-plane angle u) which are used in a process of extracting crack leading edge candidates shown in Step S209 to be described later may also be set in the process shown in Step S207. Details of the in-parallel-plane angle r and the thickness-direction-in-plane angle u will be described later with reference to FIG. 14.

Next, the process of extracting crack leading edge candidates is performed (Step S209). As described above, in the second embodiment, crack progress analysis is performed in two stages. Specifically, as the analysis process of the first stage, progress of a crack in the surface layer region of the shape model is analyzed, and as the analysis process of the second stage, the progress of the crack inside the shape model is analyzed based on the crack in the surface layer region which is obtained in the analysis process of the first stage. In Step S209, corresponding to the analysis process of the first stage, crack leading edge candidates for analyzing the progress of the crack formed in the surface layer region of the shape model are extracted. Note that details of the process shown in Step S209 will be described later with reference to FIG. 14.

Next, for each of the crack leading edge candidates extracted in Step S209, the elastic energy release rates $\delta U_e$ are calculated (Step S211). Then, using the calculated elastic energy release rates $\delta U_e$, the crack process evaluation functions p are calculated for each of the extracted crack leading edge candidates (Step S213). If m crack leading edge candidates are assumed to be extracted in Step S209, m crack progress evaluation functions $p_1$ to $p_m$ are calculated for the m crack leading edge candidates in Step S213. A crack progress evaluation function p is defined as a ratio of, for example, an elastic energy release rate $\delta U_e$ to a total toughness energy $G_c \cdot s$, i.e., $p = (\delta U_e)/(G_c \cdot s)$. The total toughness energy $G_c$·s is a toughness energy necessary when a crack progresses to a crack leading edge candidate, and can be obtained by multiplying, for example, an area s of a separation face resulting from progress of the crack which is calculated when the crack leading edge candidates are extracted in Step S209 by a toughness value per unit area of the structure $G_c$ which is set when the physical property values of the shape model are set in Step S203.

Next, the values of the crack progress evaluation functions $p_1$ to $p_m$ are compared to each other, and a maximum value ($p_{max}$) among them is extracted (Step S215). Then, in order to determine whether or not the crack will progress with respect to the crack leading edge candidate that corresponds to the crack progress evaluation function $p_{max}$ that is the maximum value, the crack progress evaluation function $p_{max}$ and the predetermined value D are compared (Step S217). Note that, since the processes shown in Steps S211 to S217 described above are the same as those shown in Steps S113 to S119 in the crack progress analysis method according to the first embodiment shown in FIGS. 3A and 3B, detailed description thereof will be omitted.

When $p_{max} \geq D=1$ is determined to be valid in Step S217, it indicates that there is a possibility of the crack progressing in the surface layer region to realize at least the crack leading edge candidate corresponding to the crack progress evaluation function $p_{max}$. Thus, when $p_{max} \geq D=1$ is determined to be valid, the crack is regarded as progressing in the surface layer region so that the crack leading edge candidate corresponding to the crack progress evaluation function $p_{max}$ is realized, and accordingly, a process of opening nodes and meshes to realize the crack leading edge candidate in the shape model and thereby cause the crack to progress is performed (Step S219).

Next, based on the opening of the nodes and meshes corresponding to the crack leading edge candidate in Step S219, it is determined whether or not the crack has reached an end of the shape model (Step S221). When the crack has not reached the end of the shape model, there is a possibility of the crack still progressing in that direction. Thus, when the crack is determined not to have reached the end of the shape model in Step S221, a new crack leading edge including the open portion is re-set as a calculation target (Step S223), and the processes from Step S209 of analyzing the progress of the crack in the surface layer region are repeated on the new crack leading edge. On the other hand, when the crack has reached the end of the shape model, it is not possible to further analyze progress of the crack in that direction. In this case, the process proceeds to Step S225, and it is determined whether the crack progress analysis that is currently performed is the analysis process of the first stage (in other words, a crack progress analysis process with respect to the surface layer region) or the analysis process of the second stage (in other words, a crack progress analysis process with respect to the internal region). When the crack is determined to have reached the end of the shape model in Step S221 and the crack progress analysis that is currently performed is determined to be the analysis process of the first stage (crack progress analysis with respect to the surface layer region) in Step S225, the analysis process of the first stage is determined to have ended, the process returns to Step S209, and the analysis process of the second stage is started.

On the other hand, when $p_{max} < D=1$ is determined to be valid in Step S217, the process proceeds to Step S225. As described above, it is determined whether the crack progress analysis that is currently performed is the analysis process of the first stage (i.e., the crack progress analysis process with respect to the surface layer region) or the analysis process of the second stage (i.e., the crack progress analysis process with respect to the internal region) in Step S225. When $p_{max} < D=1$ is determined to be valid in Step S217, the crack is considered to no longer progress in the direction that is currently considered unless the external force factor condition is changed including exerting more external force thereon. Thus, when $p_{max} < D=1$ is determined to be valid in Step S217 and the crack progress analysis that is currently performed in Step S225 is determined to be the analysis process of the first stage (crack progress analysis with respect to the surface layer region), the analysis process of the first stage is determined to have ended, the process returns to Step S209, and the analysis process of the second stage is started.

In the analysis process of the second stage, the crack leading edge candidates for analyzing the progress of the crack in the internal region of the shape model are extracted in the extraction process of the crack leading edge candidates shown in Step S209. The following processes are the same as those of the analysis process of the first stage. In other words, the elastic energy release rates 6U, and the crack progress evaluation functions p of the crack leading edge candidates extracted in Step S209 are calculated (Steps S211 and S213). The m, for example, calculated crack progress evaluation functions $p_1$ to $p_m$ are compared to each other and one that has the maximum value ($p_{max}$) among them is extracted (Step S215). Then, in order to determine whether or not the crack will progress with respect to the crack leading edge candidate that corresponds to the crack progress evaluation function $p_{max}$ that is the maximum value, the crack progress evaluation function $p_{max}$ and the predetermined value D are compared (Step S217).

When $p_{max} \geq D=1$ is determined to be valid in Step S217, it indicates that there is a possibility of the crack still progressing in the internal region, thus the crack is regarded as progressing in the internal region so as to realize the crack leading edge candidate corresponding to the crack progress evaluation function $p_{max}$, and then the process of causing the crack to progress by opening nodes and meshes is performed so as to realize the crack leading edge candidate in the shape model (Step S219). Then, based on the opening of the nodes and meshes corresponding to the crack leading edge candidate in Step S219, it is determined whether or not the crack has reached an end of the shape model (Step S221). When the crack has not reached the end of the shape model, there is a possibility of the crack still progressing in that direction. Thus, when the crack is determined not to have reached the end of the shape model in Step S221, a new crack leading edge including the open portion is re-set as a calculation target (Step S223), and the processes from Step S209 of analyzing the progress of the crack in the internal region are repeated on the new crack leading edge.

On the other hand, when the crack has reached the end of the shape model, it is not possible to further analyze the progress of the crack in that direction. In this case, the process proceeds to Step S225, and it is determined whether the crack progress analysis that is currently performed is the analysis process of the first stage (in other words, the crack progress analysis process with respect to the surface layer region) or the analysis process of the second stage (in other words, the crack progress analysis process with respect to the internal region). When the crack is determined to have reached the end of the shape model in Step S221 and the crack progress analysis that is currently performed is determined to be the analysis process of the second stage (crack progress analysis with respect to the internal region) in Step S225, the analysis process of the second stage is determined to have ended, the series of crack progress analysis processes ends.

In addition, when $p_{max}<D=1$ is determined to be valid in Step S217, the crack is considered as no longer progressing in the internal region unless the external force factor condition is changed. In this case, the process proceeds to Step S225, and at the same time, it is determined whether the crack progress analysis that is currently performed is the analysis process of the first stage (in other words, the crack progress analysis process with respect to the surface layer region) or the analysis process of the second stage (in other words, the crack progress analysis process with respect to the internal region). When the crack progress analysis that is currently performed is determined to be the analysis process of the second stage (crack progress analysis with respect to the internal region) in Step S225, the analysis process of the second stage is determined to have ended, and the series of crack progress analysis processes ends.

In the second embodiment, calculation relating to the crack progress in the surface layer region is performed until there is no crack leading edge candidate to be calculated in the analysis process of the first stage, and then calculation relating to the progress of the crack in the internal region is performed until there is no crack leading edge candidate to be calculated in the analysis process of the second stage. The state in which there is no crack leading edge candidate refers to the case in which the progress of the crack stops (in which $p_{max}<D=1$ is determined to be valid in Step S217) or the case in which the crack has reached the end of the shape model (in which the crack is determined to have reached the end of the shape model in Step S221 described above). The case in which the crack has reached the end of the shape model can also include a case in which the shape model is completely separated due to the progress of the crack. Even when the crack that is determined to satisfy $p_{max}<D=1$ in Step S217 stops progressing, however, distribution of stress added to the shape model can change and the values of the elastic energy release rates can also change when the external force factor condition is changed, and thus the series of the process may be repeated.

Next, the process procedure of the crack leading edge candidate extraction process (S209) shown in FIG. 13A will be described in detail with reference to FIG. 14. Referring to FIG. 14, it is first determined whether or not the crack progress analysis with respect to the surface layer region that is the analysis process of the first stage has ended (Step S301) in the crack leading edge candidate extraction process according to the second embodiment. When the crack progress analysis with respect to the surface layer region is determined not to have ended in Step S301, the process proceeds to Step S303, and then crack leading edge candidates when the crack progresses in the surface layer region are extracted to execute the analysis process of the first stage.

In the analysis process of the first stage, the crack leading edge candidates are extracted by searching for an angle r formed within a plane parallel to a surface of the structure (an in-parallel-plane angle r) from the crack leading edge. To be specific, first, a plurality of nodes present in the directions of different in-parallel-plane angles r of the crack leading edge are set as nodes for searching for a crack leading edge formed after progress of one session (search nodes) (Step S303). Then, leading edges of each crack candidate face formed in the crack leading edge and the search nodes are set as crack leading edge candidates (Step S305). The processes from Step S211 shown in FIGS. 13A and 13B are performed on each of the crack leading edge candidates set in Step S305.

On the other hand, when the crack progress analysis with respect to the surface layer region is determined to have ended in Step S301, the process proceeds to Step S307 and crack leading edge candidates in the internal region are extracted to execute the analysis process of the second stage. In the analysis process of the second stage, by searching for an angle within an evaluation face that passes the crack progressing node substantially perpendicular to the surface of the structure (a thickness-direction-in-plane angle u) from the node on the crack (crack progressing node) in the surface layer region obtained in the analysis process of the first stage, the crack leading edge candidates are extracted.

Specifically, nodes indicating the progress of the crack (crack progressing nodes) in the surface layer region are selected in the order of the progress of the crack in the surface layer region obtained as a result of the analysis process of the first stage (Step S307). Then, a plane that passes the selected crack progressing node and is substantially perpendicular to the surface of the shape mode (in other words, a plane in the thickness direction of the shape model) is set as an evaluation face (Step S309).

Next, the plurality of nodes present in different thickness-direction-in-plane angles u from the selected crack progress node on the set evaluation face (a thickness-direction face) are set as nodes for searching for a crack leading edge formed after progress of one session (search nodes) (Step S311). Then, the leading edges of the crack candidate face formed by the crack leading edge, the crack progressing node, and each of the search nodes is set as a crack leading edge candidate (Step S313). The processes from Step S211 shown in FIGS. 13A and 13B are performed on each of the crack leading edge candidates set in Step S313. Note that the process of extracting the crack leading edge candidates in the surface layer region performed in the analysis process of the first stage shown in Steps S303 and S305 and the process of extracting the crack leading edge candidates in the internal region performed in the analysis process of the second stage shown in Steps S307 to S313 will be described later in detail with reference to FIGS. 15 to 18E.

Hereinabove, the process procedure of the crack progress analysis method according to the second embodiment has been described with reference to FIGS. 13A, 13B, and 14. As described above, the crack progress analysis process is performed in two stages in the second embodiment, and specifically, after the progress of the crack is analyzed in the surface layer region as the analysis process of the first stage, the progress of the crack is analyzed in the internal region based on the crack present in the surface layer region. In addition, in the analysis process of the first stage, the search nodes for searching for the crack leading edge candidates are selected as the in-parallel-plane angle r changes, and in the analysis process of the second stage, the search nodes are selected as the thickness-direction-in-plane angle u changes.

Here, in the general crack progress analysis method, all nodes adjacent to the crack leading edge in the crack progressing direction (all nodes that can be taken in terms of the structure of the structure) are sequentially opened, and the elastic energy release rates $\delta U_e$ are calculated with each opening. In other words, all nodes adjacent to the crack leading edge in the crack progressing direction are selected as search nodes.

On the other hand, as described above, only the search nodes present in the direction of the in-parallel-plane angles r are selected in the analysis process of the first stage, and only the search nodes present in the direction of the thickness-direction-in-plane angle u are selected in the analysis process of the second stage according to the second embodiment. Thus, the number of selected search nodes in the second embodiment is smaller than that of the general crack progress analysis method. Therefore, the number of calculations of the elastic energy release rates $\delta U_e$ accompanied by FEM calculation executed for the crack leading edge candidates extracted according to the search nodes can be reduced and a calculation load thereof can be lowered. As such, according to the second embodiment, it is possible to perform analysis such as analysis of three-dimensional directional crack progress which has been difficult to execute in the past due to a heavy calculation load. In addition, the crack progress analysis method that uses the elastic energy release rate $\delta U_e$ is a method having high adaptability which can also be applied to analysis of a crack that progresses through different kinds of materials of a structure composed of the different kinds of materials and exfoliation thereof occurring on the interfaces, and thus in the second embodiment, crack progress analysis is realized with a lighter calculation load while maintaining high adaptability as in the first embodiment.

Note that, in the progress of a crack present in a structure, the progress of the crack present in a surface layer region is considered to heavily affect the progress of an internal crack. For example, when a crack or the like occurs on a surface of a structure, there is a high possibility of a crack progressing from the crack. In the second embodiment, even when the progress of the crack is analyzed in two stages for divided regions by analyzing the progress of the crack present in the surface layer region that has greater influence as the analysis process of the first stage and then analyzing the progress of the crack present in the interval region based on the progress of the crack present in the surface layer region, the analysis can be performed without deterioration of accuracy.

In addition, although "surface layer region" is used as a term indicating a surface of a structure or a region a predetermined depth from a surface in the above description, the second embodiment is not limited thereto. The surface layer region may refer to an interface between different kinds of materials or a region a predetermined depth from the interface with respect to one material. By setting a surface layer region regarding a surface of a structure as an interface between different kinds of materials and executing the crack progress analysis method according to the second embodiment described above, it is possible to analyze progress of a crack present in the vicinity of an interface between the materials with a lighter calculation load when the structure is composed of a combination of the different kinds of materials.

(3-2. Process of Extracting Crack Leading Edge Candidates)

Next, the process of extracting the crack leading edge candidates according to the second embodiment described with reference to FIG. 14 will be described in more detail with reference to FIGS. 15 to 18E. Herein, when the progress of the crack in the surface layer region is analyzed in the analysis process of the first stage in the second embodiment, it is possible to perform one of a method in which the progress of the crack on the surface of the shape model is analyzed and a method in which the shape model is divided into a plurality of layers and then the progress of the crack in a surface layer that is the uppermost layer is analyzed. In both methods, the progress of the crack in the internal region is analyzed in the analysis process of the second stage based on the progress of the crack on the surface or the surface layer. Hereinbelow, the two methods will be described in order.

(3-2-1. Method of Analyzing Progress of a Crack on a Surface)

Figure 15:
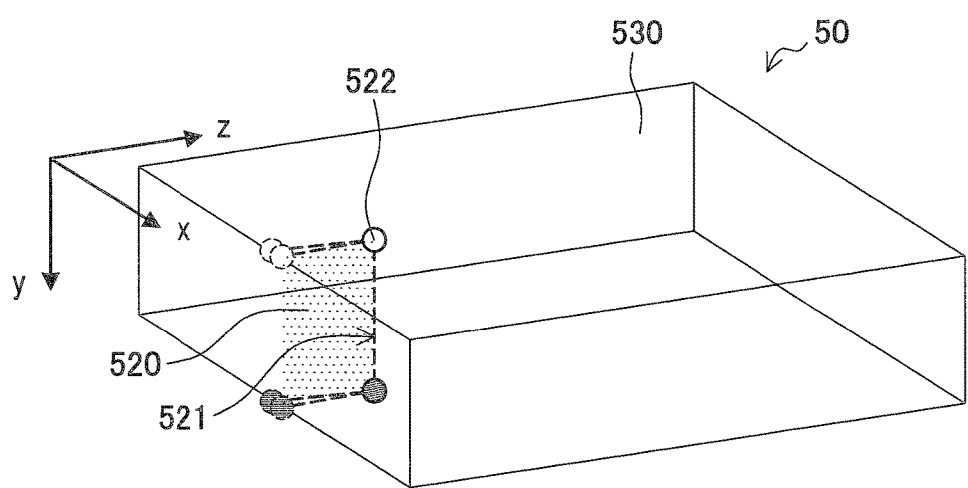
FIG. 15 is a schematic diagram showing a shape model of a structure for describing a crack progress analysis process performed on a surface.

First, the method of analyzing the progress of a crack on the surface in the analysis process of the first stage will be described with reference to FIGS. 15 and 16A to 16F. FIG. 15 is a schematic diagram showing a shape model of a structure for describing a crack progress analysis process performed on a surface. FIGS. 16A to 16F are illustrative diagrams for describing the crack progress analysis method according to the second embodiment with respect to the shape model shown in FIG. 15.

FIG. 15 is a perspective view of the shape model of the structure. Referring to FIG. 15, the shape model 50 has a cuboid shape constituted by a plurality of meshes. In order to avoid complicating the drawings, however, lines showing the meshes are not illustrated in FIGS. 15 and 16A to 16F, and nodes that can be present between the meshes are not illustrated except for those necessary for description.

A crack is occurring in a part of the shape model 50 and a crack face 520 is illustrated with hatching in FIG. 15. In the example shown in FIG. 15, the crack face 520 is present as a face substantially parallel with the y-z plane in the shape model 50. In addition, FIG. 15 illustrates nodes 522 constituting the crack face 520. Among the nodes 522, nodes 522 located on the same plane as a surface 530 are illustrated with white circles and the other nodes 522 not located in the surface 530 are illustrated with hatching. Note that, in the example shown in FIG. 15, the surface 530 is illustrated as the surface of the shape model 50, and the surface 530 can also be regarded as an interface of different kinds of materials of the structure. In addition, a crack leading edge 521 is present at an end of the crack face 520 in the positive direction of the z axis. In FIG. 15, lines forming the edges of the crack face 520 including the crack leading edge 521 are illustrated as dashed lines.

With reference to FIGS. 16A to 16F, the crack progress analysis method according to the second embodiment described with reference to FIGS. 13A, 13B, and 14 will be described again in detail showing a state in which the crack progresses in the shape model 50. A case in which the crack progresses from the state shown in FIG. 15 having the crack leading edge 521 shown in FIG. 15 set as an initial crack leading edge will be considered. As described above, the progress of the crack in the surface layer region, i.e., on the surface 530 in the example shown in FIG. 15 is analyzed as the analysis process of the first stage in the second embodiment.

Figure 16A:
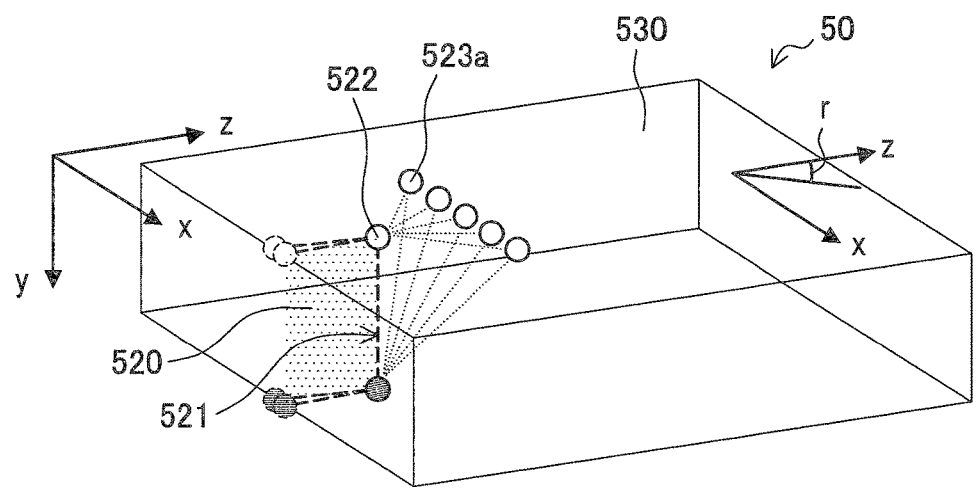
FIG. 16A is an illustrative diagram for describing the crack progress analysis method according to the second embodiment with respect to the shape model shown in FIG. 15.

In the crack progress analysis with respect to the surface 530, a plurality of nodes which are nodes on the surface 530 having different angles (in-parallel-plane angles r) formed from the initial crack leading edge 521 on the surface 530 are set as nodes 523a for searching for the crack leading edge after progress of one session (search nodes 523a) (which corresponds to the process of Step S303 shown in FIG. 14) as shown in FIG. 16A. The search nodes 523a may be nodes adjacent to the crack leading edge 521 in the crack progressing direction (in other words, nodes located adjacent thereto by one mesh). Note that, since the in-parallel-plane angle r is an angle formed within a plane parallel to the surface 530 (x-z plane), the in-parallel-plane angle r may also be referred to hereinafter as an in-x-z-plane angle r. In addition, although the in-parallel-plane angle r is defined as an angle with respect to the z-axis direction in the examples shown in FIGS. 16A to 16F and FIGS. 18A to 18E to be described later, a direction serving as a reference of the in-parallel-plane angle r may be arbitrarily set from directions parallel to the x-z plane.

FIG. 16A schematically illustrates the five search nodes 523a in the directions of five different in-parallel-plane angles r. In reality, however, i search nodes 523a corresponding to i (i is an arbitrary natural number) in-parallel-plane angles $r_1$ to $r_i$ may be set more generally. Leading edges of crack candidate faces formed by the initial crack leading edge 521 and the search nodes 523a are each set as crack leading edge candidates (which corresponds to the process of Step S305 shown in FIG. 14). Then, by performing the processes of Steps S211 to S217 shown in FIGS. 13A to 13B on the crack leading edge candidates, a crack leading edge after one session is decided.

Figure 16B:
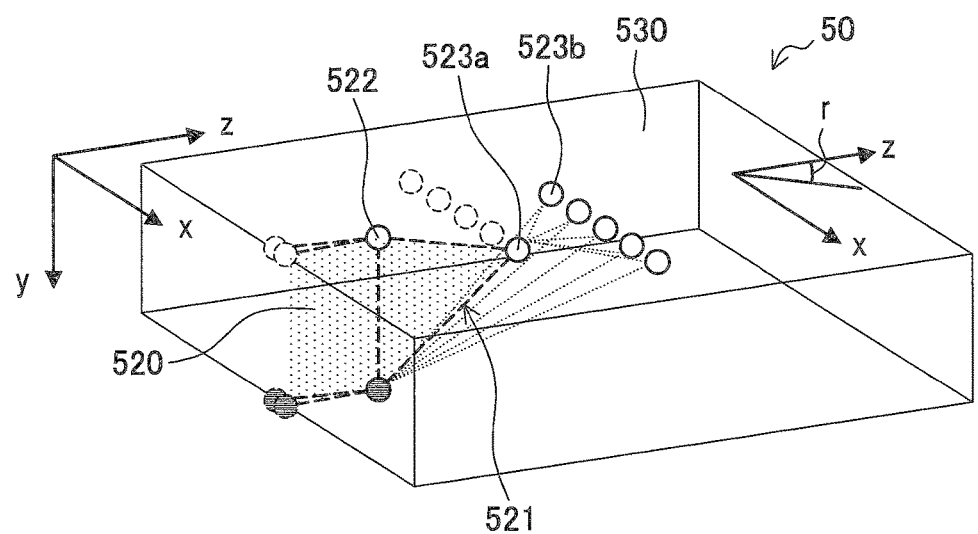
FIG. 16B is an illustrative diagram for describing the crack progress analysis method according to the second embodiment with respect to the shape model shown in FIG. 15.
Figure 16C:
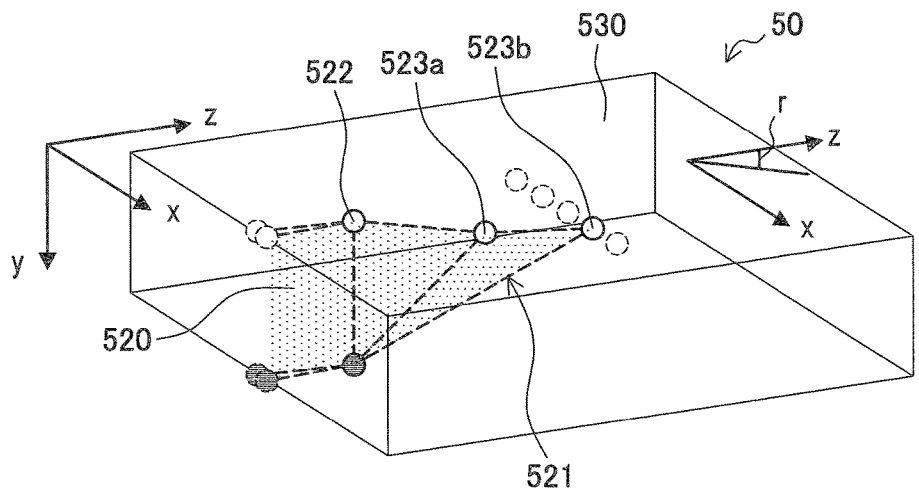
FIG. 16C is an illustrative diagram for describing the crack progress analysis method according to the second embodiment with respect to the shape model shown in FIG. 15.

FIG. 16B illustrates the crack face 520 and the crack leading edge 521 formed when the crack progresses on the surface 530 for one session from the initial crack leading edge 521 shown in FIG. 15. The crack leading edge 521 after one session is formed from the initial crack leading edge 521 that is formed before the progress of the crack by opening nodes and meshes (not illustrated) including the search nodes 523a at which the crack is determined to progress based on the crack progress evaluation function p as shown in FIG. 16B. In the same manner for the crack leading edge 521 shown in FIG. 16B, a plurality of nodes which are nodes on the surface 530 having different in-parallel-plane angles r from the initial crack leading edge 521 are set as search nodes 523b, and leading edges of crack candidate faces formed by the crack leading edge 521 and the search nodes 523b are each set as crack leading edge candidates. Then, by executing the processes of Steps S211 to S217 shown in FIGS. 13A and 13B on the crack leading edge candidates, a crack leading edge after one session is decided. FIG. 16C illustrates a crack leading edge formed when the crack progresses for one session on the surface 530 from the crack leading edge 521 shown in FIG. 16B.

Figure 16D:
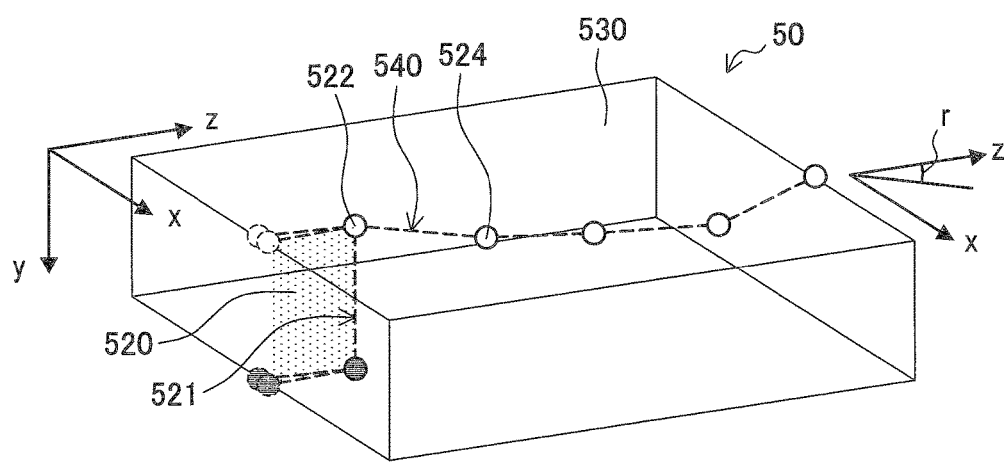
FIG. 16D is an illustrative diagram for describing the crack progress analysis method according to the second embodiment with respect to the shape model shown in FIG. 15.

Thereafter, the same processes are repeated until the progress of the crack is determined to have ended in the process of Step S217 shown in FIG. 13B and the process of Step S221. For example, when the crack progress analysis process is executed for the surface 530 until the crack reaches an end of the shape model 50, the shape of a crack 540 on the surface 530 of the shape model 50 is computed as shown in FIG. 16D. In this manner in the method of analyzing the progress of the crack on the surface 530, the shape of the crack 540 on the surface 530 can be computed in a stage after the analysis process of the first stage has ended. Note that, since the nodes constituting the crack 540 on the surface 530 shown in FIG. 16D are nodes indicating the progress of the crack on the surface 530, the nodes are also referred to as crack progressing nodes 524 for the sake of convenience of description.

Figure 16E:
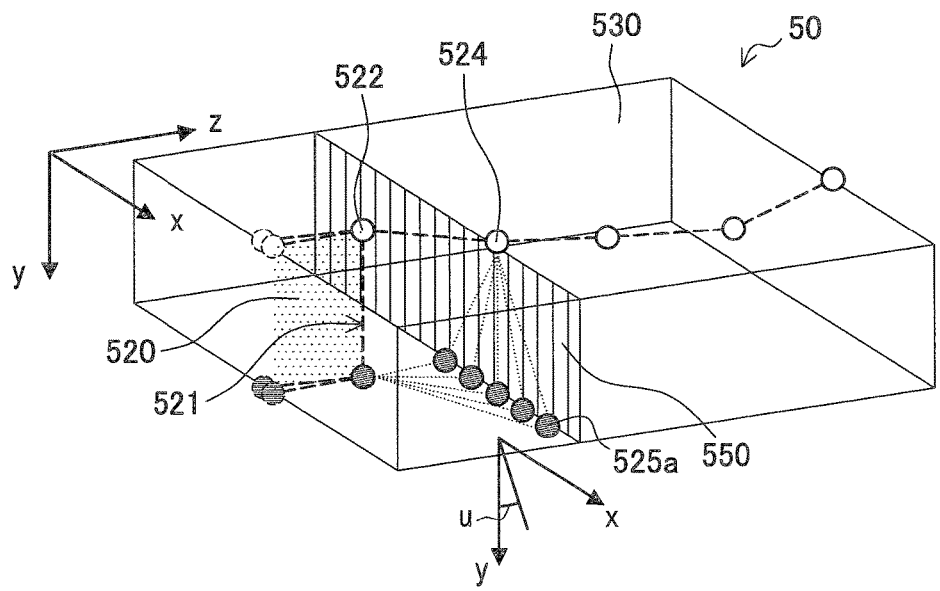
FIG. 16E is an illustrative diagram for describing the crack progress analysis method according to the second embodiment with respect to the shape model shown in FIG. 15.

When the analysis process of the first stage ends, the progress of the crack occurring in the internal region of the shape model 50 is next analyzed as the analysis process of the second stage. In the crack progress analysis with respect to the internal region, the crack progressing nodes 524 indicating the progress of the crack 540 on the surface 530 are selected (which corresponds to the process of Step S307 shown in FIG. 14) following the order of the progress of the crack 540 on the surface 530 obtained as a result of the analysis process of the first stage as shown in FIG. 16E. Then, faces of the shape model 50 in its thickness direction which passes the selected crack progressing nodes 524 and is substantially perpendicular to the surface 530 are set as an evaluation face 550 (which corresponds to the process of Step S309 shown in FIG. 14). FIG. 16E illustrates the evaluation face 550 with hatching. Note that, although the evaluation face 550 is illustrated as a face parallel to the x-y plane in the example shown in FIG. 16E, the second embodiment is not limited thereto. The evaluation face 550 may be faces substantially perpendicular to the surface 530, or the direction of the face may be arbitrary. For example, the evaluation face 550 may be set as a face that is substantially perpendicular to the surface 530 and to the progressing direction of the crack 540.

Next, a plurality of nodes which are nodes on the set evaluation face 550 having different angles from the selected crack progressing nodes 524 formed on the evaluation face 550 (thickness-direction-in-plane angles u) are set as nodes 525a for searching for a crack leading edge after progress of one session (search nodes 525a) (which corresponds to the process of Step S311 shown in FIG. 14). The thickness-direction-in-plane angle u is an angle formed on the face (x-y plane) perpendicular to the surface 530, and thus the thickness-direction-in-plane angle u will also be referred to hereinafter as an in-x-y-plane angle u. In addition, although the thickness-direction-in-plane angle u is defined as an angle formed in the y-axis direction in the examples shown in FIGS. 16A to 16F and FIGS. 18A to 18E to be described later, the direction serving as a reference of the thickness-direction-in-plane angle u may be arbitrarily set among directions parallel to the x-y plane.

FIG. 16E schematically illustrates the five search nodes 525a which correspond to the directions of five different thickness-direction-in-plane angles u. In reality, however, j (j is an arbitrary natural number) search nodes 525a which correspond to j thickness-direction-in-plane angles $u_m$ to $u_j$ may be set more generally. Leading edges of crack candidate faces formed by each of the crack leading edge 521, the crack progressing nodes 524, and the search nodes 525a are set as crack leading edge candidates (which corresponds to the process of Step S313 shown in FIG. 14). By executing the processes of Steps S211 to S217 shown in FIGS. 13A and 13B on the crack leading edge candidates, a crack leading edge after one session is decided.

Figure 16F:
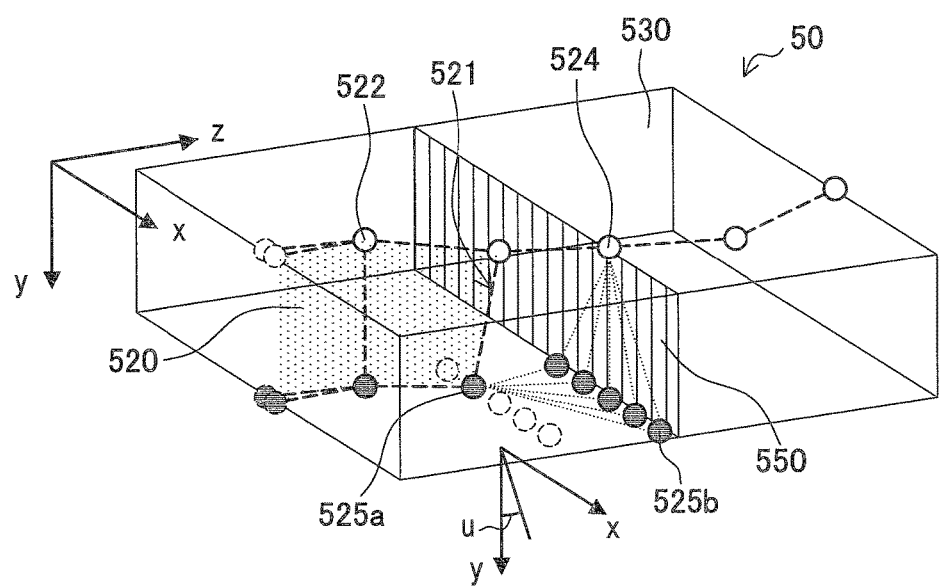
FIG. 16F is an illustrative diagram for describing the crack progress analysis method according to the second embodiment with respect to the shape model shown in FIG. 15.

FIG. 16F illustrates the crack face 520 and the crack leading edge 521 when the crack progresses for one session in the internal region from the initial crack leading edge 521 shown in FIG. 16D. The crack leading edge 521 after one session is formed from the initial crack leading edge 521 by opening nodes and meshes (not illustrated) including the selected crack progressing node 524 and the search nodes 525a at which the crack is determined to progress based on the crack progress evaluation function p as shown in FIG. 16F. Thereafter, the same processes are performed on the crack progressing nodes 524 in the order of the progress of the crack 540 on the surface 530. FIG. 16F illustrates a state in which the evaluation face 550 is set with respect to the next crack progressing node 524 likewise and a plurality of search nodes 525b having different thickness-direction-in-plane angles u from the crack progressing node 524 are set within the evaluation face.

The crack progress analysis process with respect to the internal region described above is repeated until the progress of the crack is determined to have ended in the process of Step S217 and the process of Step S221 shown in FIG. 13B, the analysis process of the second stage ends accordingly, and thereby the series of the crack progress analysis process ends. Hereinabove, the crack progress analysis method according to the second embodiment has been described using the method of analyzing the progress of the crack on the surface 530.

Note that the progress of a crack may not be analyzed for one mesh in the crack progress analysis process with respect to the surface 530. For example, the search node 523a shown in FIG. 16A may be a node separated from the crack leading edge 521 by one mesh, or may be a node present in a location separated by an arbitrary number of meshes. In the crack progress analysis process with respect to the surface 530, an amount of progress of a crack for one session may be arbitrarily set by a user. Thus, when improvement in resolving power of crack progress analysis is desired, an amount of progress for one session is finely set, and when reduction in a calculation time taken for crack progress analysis is desired, an amount of progress for one session is roughly set, and accordingly, crack progress analysis catering to users' applications is realized.

In addition, the process of extracting crack leading edge candidates of the first embodiment may be combined with the crack progress analysis process with respect to the surface 530. For example, in the case shown in FIG. 16A, a range of a total toughness energy for defining an amount of progress of a crack for one session is set and a node which enables a toughness energy when the crack progresses from the crack leading edge 521 to fall within the range of the total toughness energy may be set as the search node 523a as in the first embodiment.

(3-2-2. Method of Analyzing Progress of a Crack in a Surface Layer)

Figure 17:
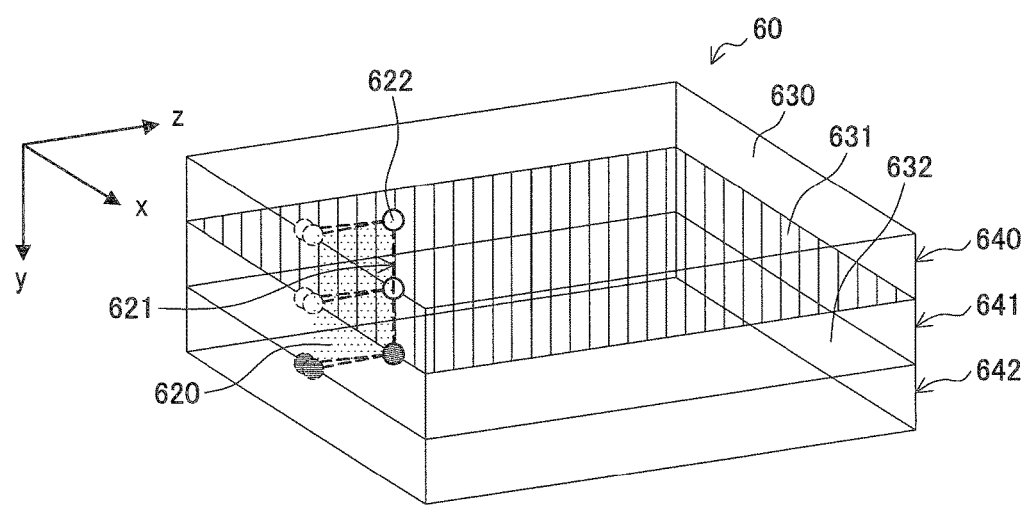
FIG. 17 is a schematic diagram showing a shape model of a structure for describing a crack progress analysis process performed on a surface layer.

Next, a method of dividing a shape model into a plurality of layers and analyzing the progress of the crack on the surface layer in the analysis process of the first stage will be described with reference to FIGS. 17 and 18A to 18E. FIG. 17 is a schematic diagram showing the shape model of a structure for describing a crack progress analysis process performed on a surface layer. FIGS. 18A to 18E are illustrative diagrams for describing the crack progress analysis method according to the second embodiment with respect to the shape model shown in FIG. 17.

FIG. 17 is a perspective view of the shape model of the structure. Referring to FIG. 17, the shape model 60 is constituted by a plurality of laminated layers. For the sake of convenience of description, the uppermost layer is referred to as a first layer 640, the second layer from the top is referred to as a second layer 641, and the third layer from the top is referred to as a third layer 642. The first layer 640 is a layer corresponding to a surface region of the shape model 60. Hereinafter, the first layer 640 is also referred to as a surface layer 640. The upper face of the surface layer 640 corresponds to a surface 630. In addition, the plane between the surface layer 640 and the second layer 641 is referred to as a second face 631, and the plane between the second layer 641 and the third layer 642 is referred to as a third face 632. In FIG. 17, the second face 631 is illustrated with hatching for easy understanding of the drawing. Although the surface layer 640, the second layer 641, and the third layer 642 can be constituted by a plurality of meshes, lines indicating meshes are not illustrated in FIGS. 17 and 18A to 18E in order to avoid complicating the drawings. In addition, in FIGS. 17 and 18A to 18E, nodes which can be present between meshes are not illustrated except for those necessary for description.

A crack has occurred in a part of the shape model 60 and a crack face 620 is illustrated with hatching in FIG. 17. In the example shown in FIG. 17, the crack face 620 is present as a face substantially parallel to the y-z plane spanning from the surface layer 640 and the second layer 641. In addition, FIG. 17 illustrates nodes 622 constituting the crack face 620. Among the nodes 622, nodes 622 located in the surface layer 640 are illustrated using white circles, and nodes 622 not located in the surface layer 640 are illustrated with hatching. Note that, although the surface layer 640 is illustrated as the surface layer of the shape model 60 in the example shown in FIG. 17, the surface layer 640 can also be regarded as a layer constituting an interface between different kinds of materials of the structure. In addition, a crack leading edge 621 is present at the end of the crack face 620 in the positive direction of the z axis. In FIG. 17, the lines constituting the edges of the crack face 620 including the crack leading edge 621 are illustrated using dashed lines.

With reference to FIGS. 18A to 18E, the crack progress analysis method according to the second embodiment described with reference to FIGS. 13A, 13B, and 14 will be described again showing a state in which the crack progresses in the shape model 60. A case in which the crack progresses from the state shown in FIG. 17 will be considered having the crack leading edge 621 shown in FIG. 17 set as an initial crack leading edge. As described above, crack progress analysis with respect to a surface layer region, i.e., the surface layer 640, is performed in the example shown in FIG. 17 as the analysis process of the first stage in the second embodiment.

Figure 18A:
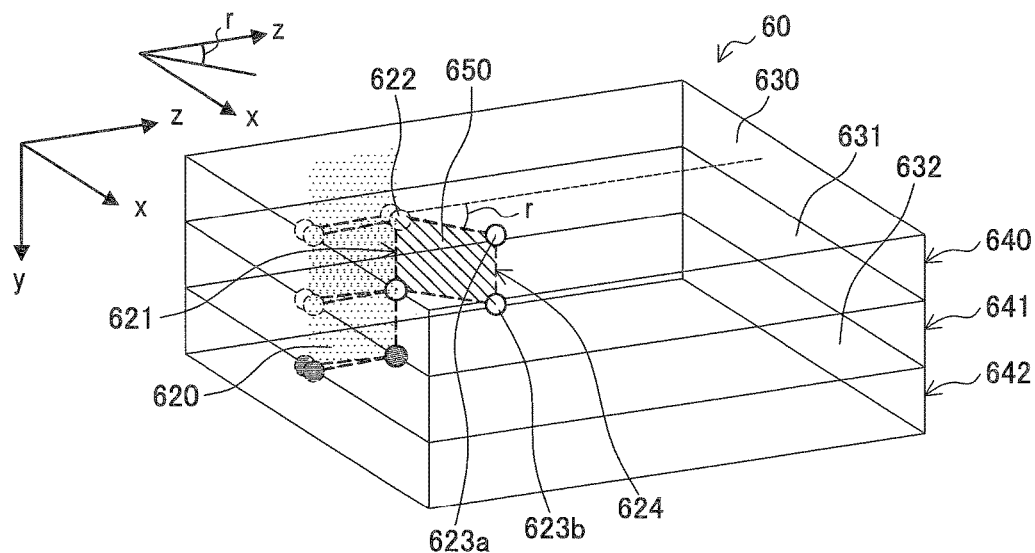
FIG. 18A is an illustrative diagram for describing the crack progress analysis method according to the second embodiment with respect to the shape model shown in FIG. 17.

In crack progress analysis with respect to the surface layer 640, a plurality of nodes which are nodes within the surface layer 640 having different angles (in-parallel-plane angles r) in the surface 630 from the initial crack leading edge 621 are set as nodes 623a and 623b for searching for a crack leading edge formed after progress for one session (search nodes 623a and 623b) as shown in FIG. 18A (which corresponds to the process of Step S303 shown in FIG. 14). Here, as the search nodes 623a and 623b in the crack progress analysis with respect to the surface layer 640, two search nodes 623a and 623b located on both faces of the surface layer 640, which are the search node 623a on the surface 630 (which is also referred to as a first search node 623a for convenience) and the search node 623b on the second face 631 (which is also referred to as a second search node 623b for convenience), are set. The first and second search nodes 623a and 623b may be set such that the line connecting the first and second search nodes 623a and 623b is substantially perpendicular to the surface 630. Note that, although FIG. 18A illustrates only one pair of the search nodes 623a and 623b, in reality, k (k is an arbitrary natural number) pairs of search nodes corresponding to k in-parallel-plane angles $r_1$ to $r_k$ may be set. In addition, the first and second search nodes 623a and 623b may be nodes, for example, adjacent to the crack leading edge 621 in the crack progressing direction (in other words, nodes located one mesh away).

Then, the leading edge of a crack candidate face 650 formed by the initial crack leading edge 621, the first search node 623a, and the second search node 623b is extracted as a crack leading edge candidate 624 (which corresponds to the process of Step S305 shown in FIG. 14). Since the first and second search nodes 623a and 623b are set such that the line connecting the first and second search nodes 623a and 623b is substantially perpendicular to the surface 630, the crack candidate face 650 can be substantially perpendicular to the surface 630.

A plurality of crack leading edge candidates 624 can be extracted with respect to a plurality of different in-parallel-plane angles r. By executing the processes of Steps S211 to S217 shown in FIGS. 13A and 13B on each of the extracted crack leading edge candidates 624, the crack leading edge 621 formed one session later is decided.

Figure 18B:
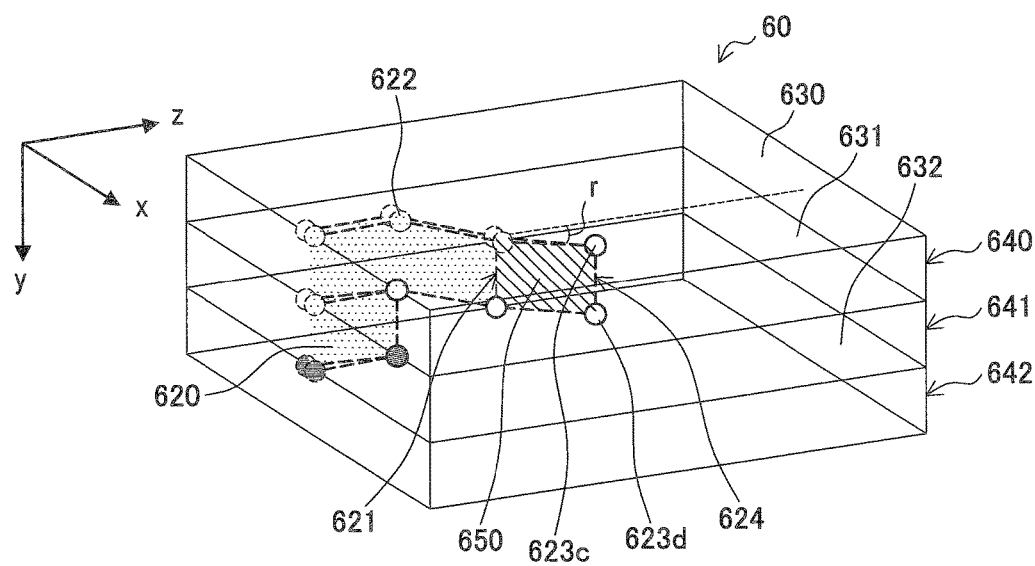
FIG. 18B is an illustrative diagram for describing the crack progress analysis method according to the second embodiment with respect to the shape model shown in FIG. 17.

For example, the crack leading edge candidate 624 shown in FIG. 18A is assumed to have been selected as the crack leading edge 621 formed one session later. By opening nodes and meshes (not illustrated) from the initial crack leading edge 621 formed before the progress of the crack to the first and second search nodes 623a and 623b constituting the crack leading edge candidate 624 shown in FIG. 18A, the new crack leading edge 621 is formed. As shown in FIG. 18B, with respect to the new crack leading edge 621, a plurality of pairs of nodes having different in-parallel-plane angles r from the crack leading edge 621 are set as search nodes for searching for the crack leading edge formed after progress of one session, and crack progress analysis based on the crack progress evaluation function p is executed on the plurality of crack leading edge candidates 624 corresponding to the pairs of the search nodes. In FIG. 18B, the crack candidate face 650 formed by one pair of search nodes 623c and 623d, the crack leading edge 621, the first search node 623a, and the second search node 623b is illustrated as an example. The leading edge of the crack candidate face 650 is the crack leading edge candidate 624.

Figure 18C:
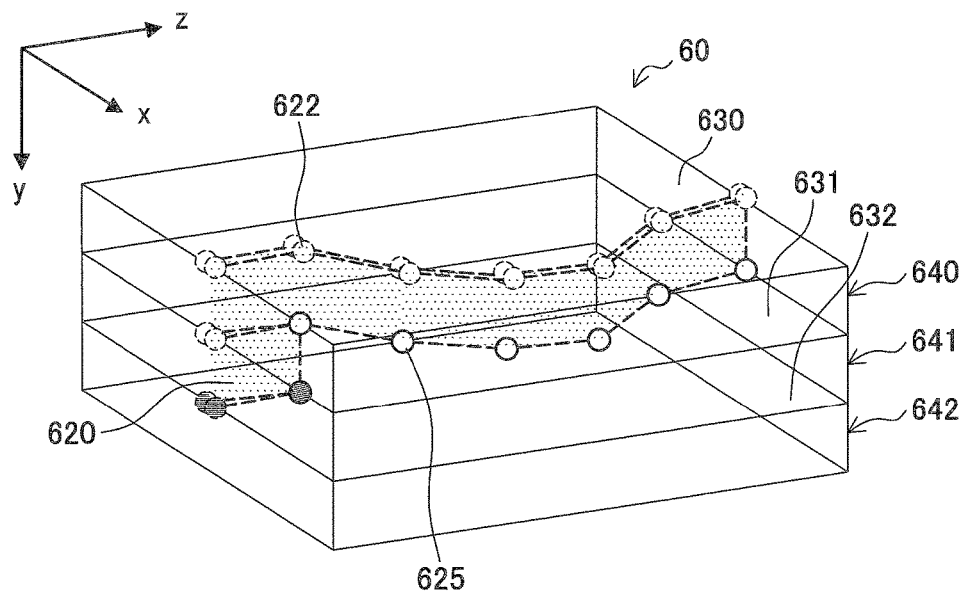
FIG. 18C is an illustrative diagram for describing the crack progress analysis method according to the second embodiment with respect to the shape model shown in FIG. 17.

Thereafter, the same processes are repeated until the progress of the crack is determined to have ended in the process of Step S217 or the process of Step S221 shown in FIG. 13B. For example, when the crack progress analysis process with respect to the surface layer 640 is executed until the crack reaches an end of the shape model 60, the shape of the crack face 620 in the surface layer 640 of the shape model 60 is computed as shown in FIG. 18C. As such, in the method of analyzing the progress of the crack in the surface layer 640, the shape of the crack face 620 in the surface layer 640 is computed in the state in which the analysis process of the first stage ends. Note that, since nodes constituting the crack face 620 in the surface layer 640 shown in FIG. 18C are nodes indicating progress of the crack face 620 in the surface layer 640, the nodes are also referred to as crack progressing nodes 625 for the sake of convenience of description.

Figure 18D:
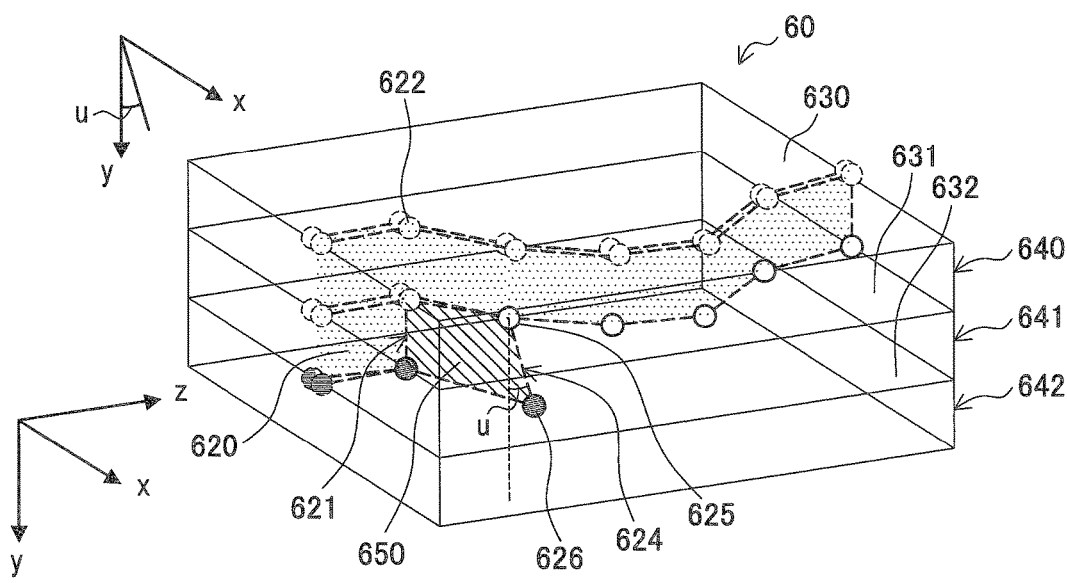
FIG. 18D is an illustrative diagram for describing the crack progress analysis method according to the second embodiment with respect to the shape model shown in FIG. 17.

When the analysis process of the first stage ends, the progress of the crack in the internal region of the shape model 60 is next analyzed as the analysis process of the second stage. Here, in the crack progress analysis with respect to the internal region, the progress of the crack in the second layer 641 can be analyzed. In the crack progress analysis with respect to the internal region, the crack progressing nodes 625 indicating the progress of the crack face 620 in the surface layer 640 which are the crack progressing nodes 625 on the second face 631 which is the interface between the surface layer 640 and the second layer 641 are selected in the order of the progress of the crack face 620 in the surface layer 640 obtained as a result of the analysis process of the first stage as shown in FIG. 18D (which corresponds to the process of Step S307 shown in FIG. 14). Then, a thickness-direction face of the shape model 60 that passes the selected crack progressing node 625 and is substantially perpendicular to the surface 630 is set as an evaluation face (which corresponds to the process of Step S309 shown in FIG. 14). Then, a plurality of nodes which are nodes on a set evaluation face having different angles (thickness-direction-in-plane angles u) from the selected crack progressing nodes 625 on the evaluation face are set as nodes 626 for searching for a crack leading edge formed after progress of one session (search nodes 626) (which corresponds to the process of Step S311 shown in FIG. 14).

Note that, although the evaluation face is not illustrated in FIG. 18D in order to avoid complicating the drawing, the evaluation face is set as, for example, a face parallel to the x-y plane as the evaluation face 550 shown in FIG. 16E described above. The second embodiment, however, is not limited thereto, and the evaluation face may be a face substantially perpendicular to the surface 630, or a direction of the face may be arbitrarily set. For example, the evaluation face may be set as a face that is substantially perpendicular to the surface 630 and to the progressing direction of the crack face 620. In addition, although FIG. 18D illustrates only one search node 626, in reality, l (l is an arbitrary natural number) search nodes corresponding to l thickness-direction-in-plane angles $u_1$ to $u_l$ may be set.

The leading edge of the crack candidate face 650 formed by the crack leading edge 621, the crack progressing node 625, and the search node 626 is extracted as a crack leading edge candidate 624 (which corresponds to the process of Step S313 shown in FIG. 14). Note that FIG. 18D illustrates only one crack leading edge candidate 624 corresponding to one search node 626 as a representative. In reality, a plurality of crack leading edge candidates 624 can be extracted with respect to a plurality of different thickness-direction-in-plane angles u. By executing the processes of Steps S211 to S217 shown in FIGS. 13A and 13B on the crack leading edge candidates 624, a crack leading edge 621 formed one session later is decided.

Figure 18E:
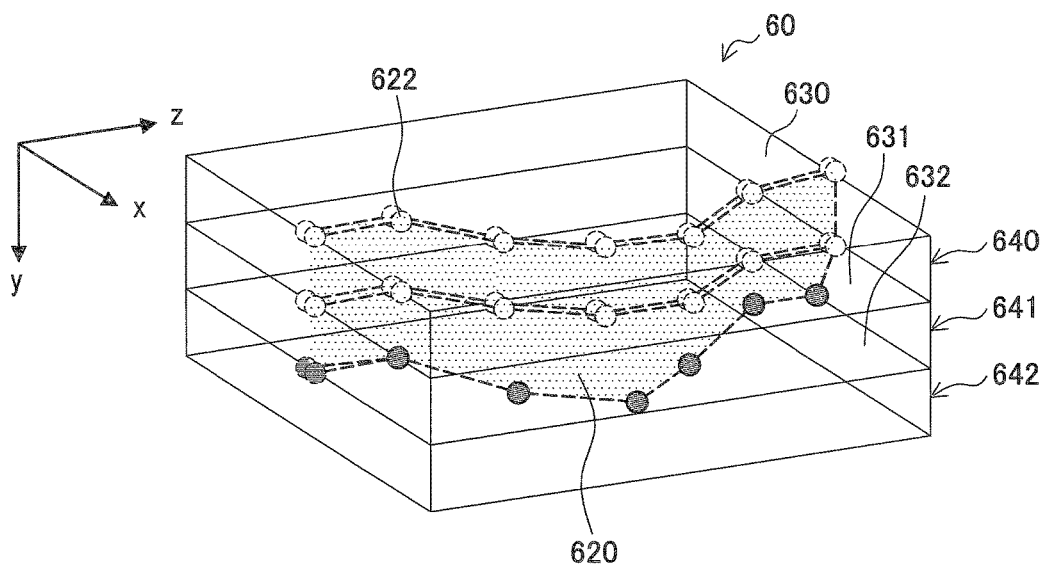
FIG. 18E is an illustrative diagram for describing the crack progress analysis method according to the second embodiment with respect to the shape model shown in FIG. 17.

After the crack progress analysis process with respect to the internal region described above is repeated until the progress of the crack is determined to have ended in the process of Step S217 and the process of Step S221 shown in FIG. 13B, the analysis process of the second stage ends, and the series of crack progress analysis process ends. An example of the shape of the crack face 620 in the stage in which the crack progress analysis process ends is shown in FIG. 18E. Note that the crack progress analysis with respect to the internal region may not be finished in the stage in which the crack progress analysis with respect to the second layer 641 ends, and the crack progress analysis process may be further executed for another layer (the third layer 642 in the illustrated example) inside the shape model 60, for example, from the state shown in FIG. 18E in the same manner. When the analysis process is sequentially executed in the thickness direction of the shape model 60 and the progress of the crack in the thickness direction also ends, the series of crack progress analysis processes may be determined to have ended.

Hereinabove, the method of analyzing the progress of the crack in the surface layer 640 in the crack progress analysis method according to the second embodiment has been described. Herein, in the method described in (3-2-2. Method of analyzing progress of a crack in a surface layer) above, there is a possibility of the crack face 520 having a triangular shape with a high aspect ratio in the analysis process of the first stage as shown in, for example, FIG. 16C. If FEM calculation is performed on the shape model 50 having the crack face 520 of the shape, there is concern of calculation not converging depending on the shape of the crack face 520. On the other hand, when the progress of the crack on the surface layer 640 is analyzed in the analysis process of the first stage as described above, the search nodes on the second face 631 (for example, the nodes 623b and 623d shown in FIGS. 18A and 18B) play a role of so-called connection nodes which connect the surface region and the internal region. As such, by providing the connection nodes which connect the surface region and the internal region and analyzing the progress of the crack in the surface region using the connection nodes, the accuracy of FEM calculation can be enhanced and more stable crack progress analysis can be performed.

Note that, as in (3-2-1. Method of analyzing progress of a crack on a surface) described above, the progress of the crack may not be analyzed for each mesh in the crack progress analysis process with respect to the surface layer 640. For example, the search nodes 623*a* and 623*b* shown in FIG. 18A may be nodes separated from the crack leading edge 621 by one mesh, or may be nodes present in a location separated by an arbitrary number of meshes. In the crack progress analysis process with respect to the surface layer 640, an amount of progress of a crack for one session may be arbitrarily set by a user. Accordingly, when improvement in resolving power of crack progress analysis is desired, the amount of progress for one session is finely set, and when reduction in a calculation time taken for crack progress analysis is desired, the amount of progress for one session is roughly set, and accordingly, crack progress analysis catering to users' applications is realized.

In addition, the process of extracting crack leading edge candidates of the first embodiment may be combined with the crack progress analysis process with respect to the surface layer 640. For example, in the case shown in FIG. 18A, a range of a total toughness energy for defining an amount of progress of a crack for one session is set and nodes which enable a toughness energy when the crack progresses from the crack leading edge 621 to fall within the range of the total toughness energy may be set as the search nodes 623*a* and 623*b* as in the first embodiment.

(3-3. Comparison of Calculation Loads)

Herein, a calculation load of the general crack progress analysis method described with reference to FIGS. 1A and 1B will be compared to a calculation load of the crack progress analysis method according to the second embodiment described with reference to FIGS. 13A and 13B. Herein, the difference of the calculation loads will be described exemplifying the crack progress analysis with respect to the shape model 50 and the initial crack leading edge 521 shown in FIG. 15 when the crack progresses in the z-axis direction for one session as an example.

(3-3-1. Calculation Load of the General Crack Progress Analysis Method)

Figure 19A:
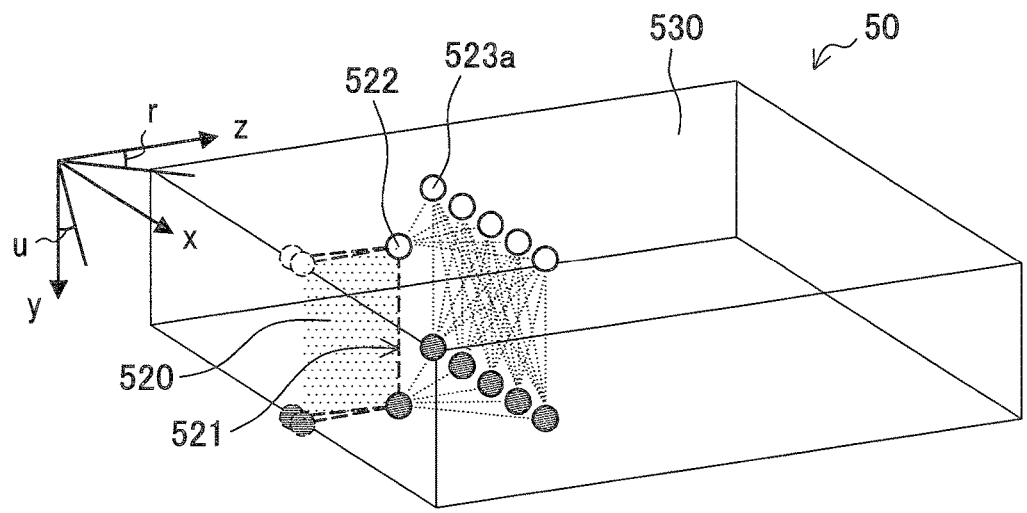
FIG. 19A is an illustrative diagram for describing a calculation load of the general crack progress analysis method.
Figure 19B:
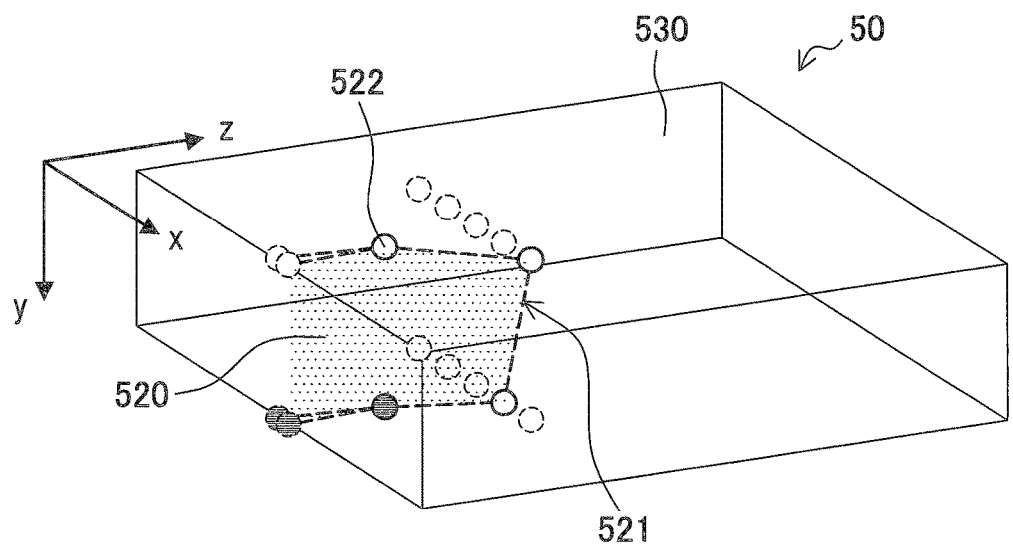
FIG. 19B is an illustrative diagram for describing the calculation load of the general crack progress analysis method.

First, a case in which the progress of the crack in the shape model 50 shown in FIG. 15 is analyzed according to the process procedure of the general crack progress analysis method shown in FIGS. 1A and 1B will be described with reference to FIGS. 19A and 19B. FIGS. 19A and 19B are illustrative diagrams for describing a calculation load of the general crack progress analysis method. Note that, as described in (1-1. Process procedure of a general crack progress analysis method) above, the calculation load of the calculation of an elastic energy release rate using the FEM is dominant with respect to the calculation load of the general crack progress analysis method. Thus, the difference of the calculation load will be described herein, focusing on the number of calculations of the elastic energy release rate using the FEM.

As described in (1-1. Process procedure of a general crack progress analysis method) above, an elastic energy release rate is calculated for each node (all nodes which can form crack leading edge candidates in terms of the structure of the shape model 50) adjacent to the crack leading edge in the crack progressing direction in the general crack progress analysis method. For simplification, it is assumed that there are a total of ten nodes including five node 523*a* (search node 523*a*) adjacent to the crack leading edge 521 in the crack progressing direction on the surface 530 and five more nodes on a face other than the surface 530 as shown in FIG. 19A. In this case, crack progress evaluation functions p are calculated for each combination of all of the nodes 523*a* located on the surface 530 and the nodes 523*a* located on the opposite face to the surface 530 (5×5=25) in the general crack progress analysis method. Accordingly, 25 FEM calculations are executed to analyze the progress of the crack for one session. As such, since the FEM calculation is performed for all crack leading edge candidates which can be obtained, so to speak, in terms of the construction of the shape model 50 in the general crack progress analysis method, a calculation load thereof can be heavy. As a result of evaluating the crack progress evaluation functions p calculated for each of the general crack leading edge candidates, for example, the crack face 520 shown in FIG. 19B is computed as a crack face after the progress.

(3-3-2. Calculation Load of the Crack Progress Analysis Method According to the Second Embodiment)

Figure 20A:
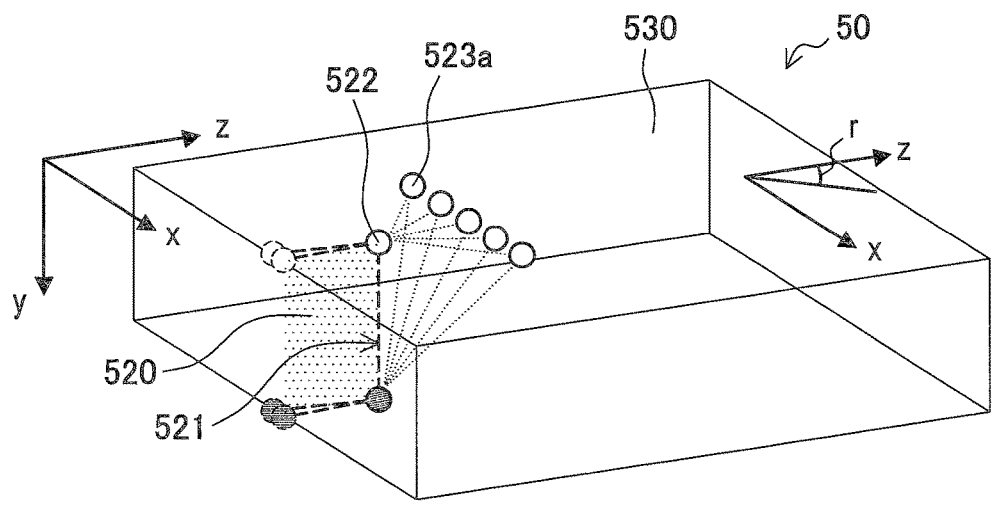
FIG. 20A is an illustrative diagram for describing a calculation load of the crack progress analysis method according to the second embodiment.
Figure 20B:
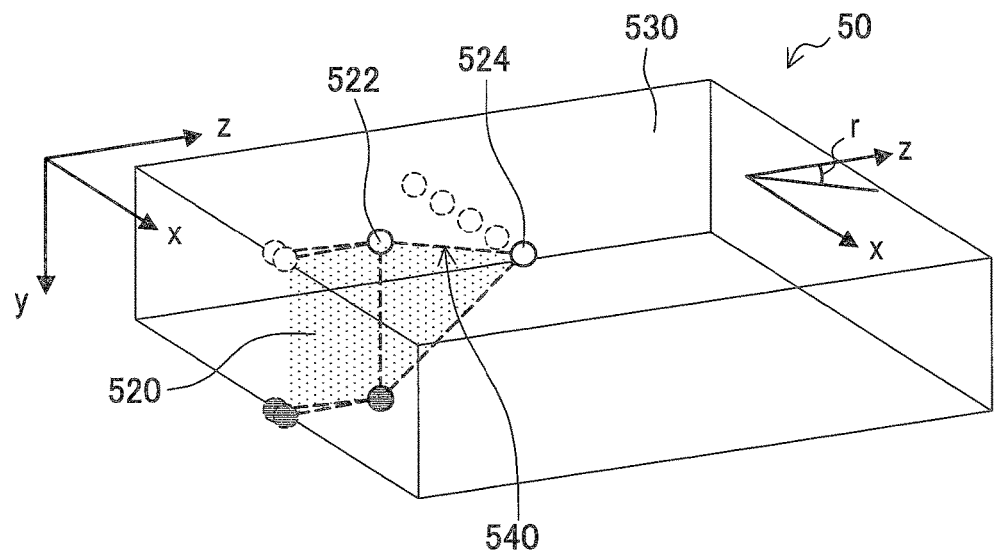
FIG. 20B is an illustrative diagram for describing the calculation load of the crack progress analysis method according to the second embodiment.
Figure 20C:
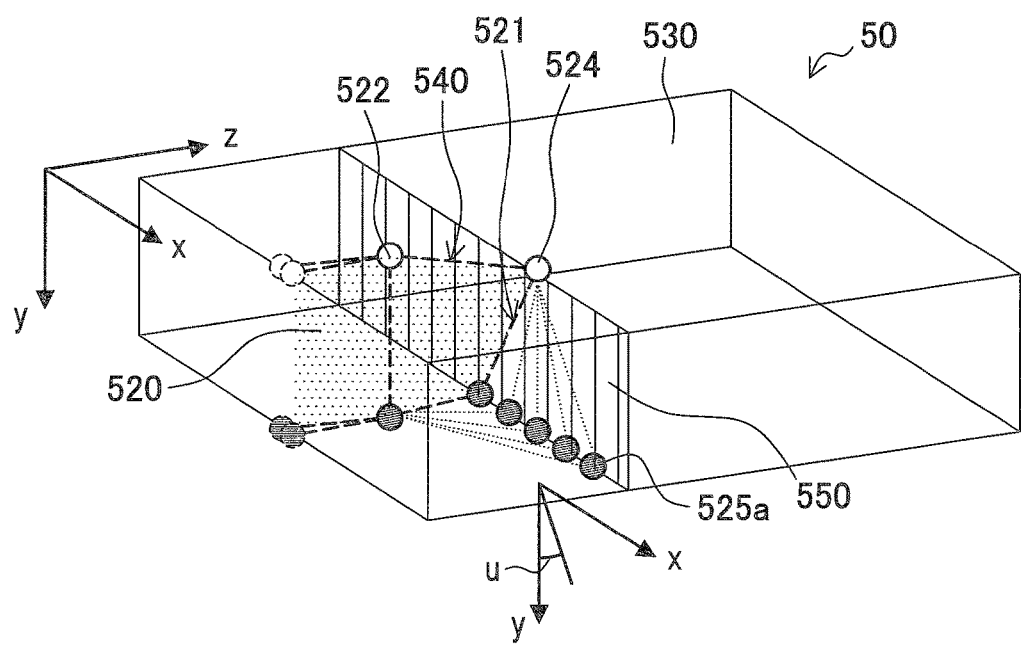
FIG. 20C is an illustrative diagram for describing the calculation load of the crack progress analysis method according to the second embodiment.

Next, a case in which the progress of the crack in the shape model 50 shown in FIG. 15 is analyzed according to process procedure of the crack progress analysis method according to the second embodiment shown in FIGS. 13A and 13B will be described with reference to FIGS. 20A to 20C. FIGS. 20A to 20C are illustrative diagrams for describing a calculation load of the crack progress analysis method according to the second embodiment. Herein, a calculation load when crack progress analysis is performed using the method described in (3-2-1. Method of analyzing progress of a crack on a surface) above will be described as an example.

As described in (3-1. Process procedure of a crack progress analysis method according to the second embodiment) above, the progress of the crack in the surface layer region (for example, the surface 530) of the shape model 50 is analyzed as the analysis process of the first stage and the progress of the crack in the internal region of the shape model 50 is analyzed as the analysis process of the second stage in the crack progress analysis method according to the second embodiment.

First, in the analysis process of the first stage, the plurality of nodes 523*a* located at different in-parallel-plane angles r from the crack leading edge 521 on the surface 530 are set as the search nodes 523*a* for searching for a crack leading edge after the progress as shown in FIG. 20A. Then, leading edges of the crack candidate faces formed by the crack leading edge 521 and the search nodes 523*a* are each set as crack leading edge candidates. In the same manner as in (3-3-1. Calculation load of the general crack progress analysis method) above, when there are a total of ten nodes including five nodes 523*a* adjacent to the crack leading edge 521 in the crack progressing direction on the surface 530 and five more nodes on the opposite face to the surface 530, five crack leading edge candidates are extracted in the analysis process of the first stage in the crack progress analysis method according to the second embodiment. Since the crack progress evaluation functions p are calculated for each of the five crack leading edge candidates, five FEM calculations are performed in the analysis process of the first stage.

An example of the crack face 520 in the stage in which the analysis process of the first stage, i.e., the crack progress analysis process with respect to the surface 530, ends is shown in FIG. 20B. In the second embodiment, the analysis process of the second stage, i.e., the crack progress analysis with respect to the internal region of the shape model 50, is performed in the state shown in FIG. 20B. To be specific, the crack progressing node 524 indicating the progress of the crack 540 on the surface 530 is selected and a face of the shape model 50 in the thickness direction that passes the selected crack progressing node 524 and is substantially perpendicular to the surface 530 is set as the evaluation face 550 as shown in FIG. 20C. Then, a plurality of nodes which are nodes within the evaluation face 550 having different thickness-direction-in-plane angles u from the selected crack progressing node 524 are set as the search nodes 525a for searching for a crack leading edge after the progress.

In the example shown in FIG. 20C, five search nodes 525a can be set. Thus, a total of five crack leading edge candidates each corresponding to the crack candidate faces formed by the crack leading edge 521, the crack progressing node 524, and the search nodes 525a are extracted. Since crack progress evaluation functions p are calculated for each of the five crack leading edge candidates, five FEM calculations are performed in the analysis process of the second stage. As the analysis process of the second stage ends, the progress of the crack for one session is analyzed. As such, according to the second embodiment, since five of the FEM calculations are performed in the analysis process of the first stage and five of the FEM calculations are performed in the analysis process of the second stage, a total of ten of the FEM calculations are executed to analyze the progress of the crack for one session.

Hereinabove, with respect to a calculation load generated when the progress of a crack for one session is analyzed for the same shape model 50, the calculation load of the general crack progress analysis method and the calculation load of the crack progress analysis method according to the second embodiment have been described. In the general crack progress analysis method, a total of 25 of the FEM calculations are necessary for analyzing the progress of the crack for one session as described above. On the other hand, according to the crack progress analysis method of the second embodiment, the number of FEM calculations necessary for analyzing the progress of the crack for one session can be reduced to ten in total.

In the general crack progress analysis method, all nodes adjacent to the crack leading edge (all nodes which can be obtained in terms of the structure of the shape model 50) can be selected as nodes constituting the crack leading edge formed after the progress of the crack. This means that, when nodes constituting the crack leading edge formed after the progress of the crack are searched for, searching of the search nodes 523a within a face parallel to the surface 530 (in other words, searching of the search nodes 523a on the surface 530 by changing the in-parallel-plane angles r) and searching of the search nodes 523a in the internal region of the shape model 50 (in other words, searching of the search nodes 523a within a thickness-direction face by changing the thickness-direction-in-plane angles u) are performed at the same time in a round-robin manner. Thus, the number of search nodes 523a to be extracted increases and the number of FEM calculations to be executed also increases. On the other hand, in the crack progress analysis method according to the second embodiment, the progress of the crack is analyzed in two stages, the progress of the crack on the surface 530 of the shape model 50 is analyzed in the analysis process of the first stage and the progress of the crack in the internal region of the shape model 50 is analyzed using the result of the analysis process of the first stage in the analysis process of the second stage. Thus, in comparison with the case in which the search nodes 523a are selected in a round-robin manner as in the general crack progress analysis method, the number of search nodes 523a to be selected can be lowered and the calculation time can be dramatically reduced. Therefore, in the second embodiment, the calculation load can be further lessened while performing the analysis method with high adaptability using the elastic energy release rate.

(4. Device Configuration)

Figure 21:
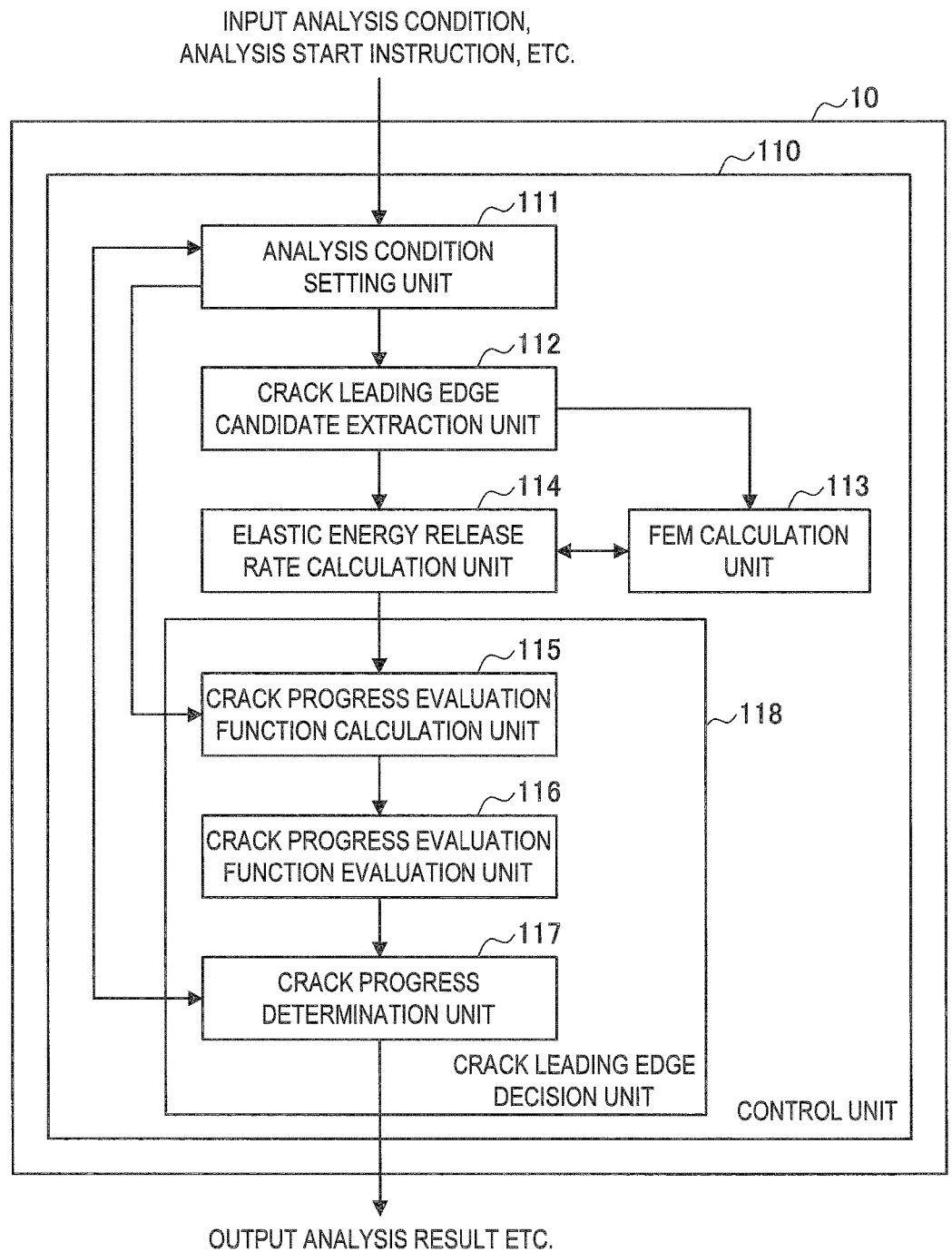
FIG. 21 is a functional block diagram showing a functional configuration of an information processing apparatus according to the first and second embodiments.

Next, a configuration of an information processing apparatus for realizing the crack progress analysis method according to the first and second embodiments described above will be described with reference to FIG. 21. FIG. 21 is a functional block diagram showing a functional configuration of the information processing apparatus according to the first and second embodiments.

Referring to FIG. 21, the information processing apparatus 10 according to the first and second embodiments has a control unit 110. The information processing apparatus 10 may be any of various kinds of information processing apparatuses, for example, a PC, a workstation, and the like and can be realized with a hardware configuration to be described later.

Note that, among functions of the information processing apparatus 10, FIG. 21 mainly illustrates the functions that relate to the crack progress analysis method according to the first and second embodiments, and for the sake of simplification does not illustrate other functions. Since the other functions which are not illustrated are the same as various functions that a general known information processing apparatus includes, detailed description thereof will be omitted. For the functions not illustrated, the information processing apparatus 10 may further include, for example, an input unit configured with a mouse, a keyboard, a touch panel, and the like for users to input various kinds of information to the information processing apparatus 10, a display unit configured with a display device or the like for visually outputting various results processed in the information processing apparatus 10 to users, a communication unit that exchanges various kinds of information with an external device of the information processing apparatus 10 via various kinds of networks, and/or a storage unit configured with a storage device or the like for storing various kinds of information processed in the information processing apparatus 10.

The control unit 110 is configured with various kinds of processors, for example, a central processing unit (CPU), a digital signal processor (DSP), and the like, and comprehensively controls operations of the information processing apparatus 10 by performing various signal processes according to a predetermined program. In the above embodiments, each of the processes shown in the flowchart of FIGS. 3A and 3B and the flowcharts shown in FIGS. 13A, 13B, and 14 can be executed by the control unit 110. Referring to FIG. 21, the control unit 110 has an analysis condition setting unit 111, a crack leading edge candidate extraction unit 112, an FEM calculation unit 113, an elastic energy release rate calculation unit 114, and a crack leading edge decision unit 118 for its functions.

The analysis condition setting unit 111 sets various analysis conditions necessary for the series of crack progress analysis processes according to the present embodiment. As processes of setting analysis conditions, for example, the analysis condition setting unit 111 performs processes of creating a shape model expressing a structure to be analyzed, setting physical property values (an elastic modulus, a toughness value, and the like) of the structure, setting of an initial crack leading edge, forming meshes in the shape model, setting of an arithmetic operation formula of an elastic energy release rate, setting of a definition formula of a crack progress evaluation function, setting of various parameters used in the FEM calculation such as the external force factor condition, and the like. In addition, in the first embodiment, the analysis condition setting unit 111 can further set a total toughness energy for extracting a crack leading edge candidate obtained one session later. In addition, in the second embodiment, the analysis condition setting unit 111 can further set a change range of the in-parallel-plane angle r and the thickness-direction-in-plane angle u for extracting the crack leading edge candidate obtained one session later. As such, the processes performed by the analysis condition setting unit 111 corresponds to the processes of Steps S101 to S109 of the crack progress analysis method according to the first embodiment shown in FIG. 3A or the processes of Steps S201 to S207 of the crack progress analysis method according to the second embodiment shown in FIG. 13A. The analysis condition setting unit 111 provides information regarding the set analysis conditions to the crack leading edge candidate extraction unit 112.

Note that specific content of an analysis condition set by the analysis condition setting unit 111 may be input to the information processing apparatus 10 according to a manipulation by a user via, for example, the above-described input unit, or may be input to the information processing apparatus 10 from another external device via the above-described communication unit. The analysis condition input to the information processing apparatus 10 may be stored once in the above-described storage unit, and the analysis condition setting unit 111 may set various analysis conditions referring to the storage unit. In addition, a timing at which the analysis condition setting unit 111 starts a setting of an analysis condition may be, for example, a timing at which a user inputs a command of instructing start of the analysis of progress of a crack to the information processing apparatus 10 via the input unit or the communication unit.

The crack leading edge candidate extraction unit 112 extracts a crack leading edge candidate based on the set analysis conditions. The crack leading edge candidate extraction unit 112 can extract the crack leading edge candidate which satisfies the predetermined conditions from crack leading edge candidates which can be obtained in terms of the construction of a structure (shape model).

In the first embodiment, in the structure constituted by a plurality of meshes, the crack leading edge candidate extraction unit 112 extracts a crack leading edge candidate after the progress of the crack of which the total toughness energy necessary for separating the plurality of meshes is likely to fall within a predetermined range when the crack progresses. In addition, in the first embodiment, the crack leading edge candidate extraction unit 112 can extract a crack leading edge candidate based on the two conditions (the condition for continuity of a crack leading edge and the condition for continuity of a crack before and after progress) described in (2-2. Process of extracting a crack leading edge candidate) above.

In addition, in the second embodiment, the crack leading edge candidate extraction unit 112 can extract a crack leading edge candidate under different conditions in the analysis process of the first stage and the analysis process of the second stage. In the analysis process of the first stage, the crack leading edge candidate extraction unit 112 extracts the crack leading edge candidate when the crack progresses in the surface layer region of the structure. To be specific, in the analysis process of the first stage, the crack leading edge candidate extraction unit 112 searches for angles (in-parallel-plane angles r) within a face parallel to the surface of the structure from the crack leading edge formed before the progress of the crack, and thereby sets nodes of the surface layer region located in the direction of a plurality of different in-parallel-plane angles r formed from the current crack leading edge as search nodes, and then extracts the leading edge of the crack candidate face formed by the current crack leading edge and the search nodes as the crack leading edge candidate. In addition, in the analysis process of the second stage, the crack leading edge candidate extraction unit 112 extracts the crack leading edge candidate formed when the crack progresses in the internal region of the structure based on the crack in the surface layer region obtained as a result of the analysis process of the first stage. To be specific, in the analysis process of the second stage, the crack leading edge candidate extraction unit 112 searches for angles (thickness-direction-in-plane angles u) within an evaluation face which passes a crack progressing node and is substantially perpendicular to the surface of the structure from nodes on the crack in the surface layer region (crack progressing nodes), accordingly sets nodes in the internal region of the structure which are located in the direction of the plurality of different thickness-direction-in-plane angles u formed from the crack progressing nodes as search nodes, and then extracts the leading edges of the crack candidate faces formed by the current crack leading edge, the crack progressing nodes, and the search nodes as crack leading edge candidates.

The process performed by the crack leading edge candidate extraction unit 112 corresponds to the process of Step S111 in the crack progress analysis method according to the first embodiment shown in FIG. 3A or the process of Step S209 in the crack progress analysis method according to the second embodiment shown in FIG. 13A (in other words, each of the processes shown in FIG. 14). The crack leading edge candidate extraction unit 112 provides information of the extracted crack leading edge candidate to the FEM calculation unit 113 and the elastic energy release rate calculation unit 114.

The FEM calculation unit 113 performs analysis of stress using the FEM on a structure in order to calculate an elastic energy release rate. To be specific, the FEM calculation unit 113 computes the elastic energy of the whole system in the state in which a position of a crack leading edge is that of an initial crack leading edge by calculating distribution of stress in the structure in the state in which a position of a crack leading edge is that of an initial crack leading edge using the FEM under a predetermined external force factor condition. In addition, the FEM calculation unit 113 computes the elastic energy of the whole system in the state in which the position of the crack leading edge is that of a crack leading edge candidate by calculating distribution of stress exerted on the structure using the FEM under a predetermined external force factor condition for the state in which the position of the crack leading edge is that of a crack leading edge candidate. The FEM calculation unit 113 provides information of the result of the analysis of stress with respect to the structure which includes information of the computed elastic energy to the elastic energy release rate calculation unit 114. Note that, since various known methods generally used in the FEM are applied to the analysis of stress performed by the FEM calculation unit 113 using the FEM, description of the detailed calculation method will be omitted.

Based on the result of the analysis of stress performed by the FEM calculation unit 113, the elastic energy release rate calculation unit 114 calculates an elastic energy release rate that is an elastic energy released as the meshes are separated when the crack progresses to the state indicated by the extracted crack leading edge candidate. To be specific, the elastic energy release rate calculation unit 114 can obtain the difference between the elastic energy of the whole system in the state in which a position of a crack leading edge is that of an initial crack leading edge and the elastic energy of the whole system in the state in which the position of the crack leading edge is that of the crack leading edge candidate to calculate the elastic energy release rate. The processes performed by the FEM calculation unit 113 and the elastic energy release rate calculation unit 114 correspond to the process of Step S113 in the crack progress analysis method according to the first embodiment shown in FIG. 3A or the process of Step S211 in the crack progress analysis method according to the second embodiment shown in FIG. 13A. The elastic energy release rate calculation unit 114 provides information of the calculated elastic energy release rate to the crack leading edge decision unit 118.

The crack leading edge decision unit 118 decides a crack leading edge after the progress of a crack at least based on the elastic energy release rate. Specifically, the crack leading edge decision unit 118 selects a crack leading edge candidate having the highest possibility of realization in light of the energy of the whole system from a plurality of crack leading edge candidates extracted by the crack leading edge candidate extraction unit 112, and thereby can decide a crack leading edge after the progress of the crack. In addition, the crack leading edge decision unit 118 can also determine whether or not the crack will progress along the crack leading edge candidate in light of the energy of the whole system.

The function of the crack leading edge decision unit 118 will be described in more detail. The crack leading edge decision unit 118 has a crack progress evaluation function calculation unit 115, a crack progress evaluation function evaluation unit 116, and a crack progress determination unit 117 for its functions.

The crack progress evaluation function calculation unit 115 calculates a crack progress evaluation function that is an index indicating a possibility of realizing the crack leading edge candidate at least based on the elastic energy release rate. When there are a plurality of crack leading edge candidates, the crack progress evaluation function calculation unit 115 calculates crack progress evaluation functions of the respective crack leading edge candidates. The crack progress evaluation function p can be calculated according to the definition formula set by the analysis condition setting unit 111. The crack progress evaluation function p may be defined as, for example, the ratio of an elastic energy release rate to a total toughness energy (in other words, a toughness energy necessary for causing a crack to progress to a crack leading edge candidate) (($p=(\delta U_e)/(G_c \cdot s)$)). Note that, when the crack progress evaluation function p is calculated as the ratio of an elastic energy release rate to a total toughness energy, a predetermined coefficient may be multiplied if necessary. The crack progress evaluation function calculation unit 115 calculates the area of the separation face of meshes that has occurred due to the progress of a crack based on a crack leading edge candidate extracted by the crack leading edge candidate extraction unit 112, then calculates the total toughness energy corresponding to the crack leading edge candidate based on the area and the toughness value per unit area of a structure set by the analysis condition setting unit 111, and thereby can calculate the crack progress evaluation function p. As such, the process performed by the crack progress evaluation function calculation unit 115 corresponds to the process of Step S115 in the crack progress analysis method according to the first embodiment shown in FIG. 3A or the process of Step S213 in the crack progress analysis method according to the second embodiment shown in FIG. 13A.

Here, in the first and second embodiments, the crack progress evaluation function is not limited to the form described above, and can have any other form as long as it is defined as a function obtained by comparing the magnitude relation between an elastic energy release rate and a total toughness energy. For example, the crack progress evaluation function calculation unit 115 may calculate a crack progress evaluation function p as the difference between an elastic energy release rate and a total toughness energy. In addition, when a structure is composed of a single material, for example, the crack progress evaluation function calculation unit 115 may calculate a crack progress evaluation function p as a function that can determine progress or non-progress and a progressing direction of a crack based on an elastic energy release rate. The crack progress evaluation function calculation unit 115 provides information of the calculated crack progress evaluation function to the crack progress evaluation function evaluation unit 116.

The crack progress evaluation function evaluation unit 116 decides a crack leading edge after the progress of the crack by selecting the crack leading edge candidate having the highest possibility of realization from the plurality of crack leading edge candidates based on the calculated crack progress evaluation function. For example, when the crack progress evaluation function is calculated with $p=(\delta U_e)/(G_c \cdot s)$, the crack progress evaluation function evaluation unit 116 compares the magnitude of crack progress evaluation functions p calculated for each of crack leading edge candidates, and selects a crack leading edge candidate having the highest value of p among them as the crack leading edge candidate having the highest possibility of realization. As such, the process performed by the crack progress evaluation function evaluation unit 116 corresponds to the process of Step S117 in the crack progress analysis method according to the first embodiment shown in FIG. 3B or the process of Step S215 in the crack progress analysis method according to the second embodiment shown in FIG. 13B. When the crack leading edge candidate extraction unit 112 extracts only one crack leading edge candidate, the crack progress evaluation function evaluation unit 116 may select the crack leading edge candidate as the crack leading edge candidate having the highest possibility of realization. In addition, when the form of a crack progress evaluation function is different, the crack progress evaluation function evaluation unit 116 can appropriately select one having the highest possibility of realization among crack leading edge candidates using a method suitable for the form of the crack progress evaluation function. The crack progress evaluation function evaluation unit 116 provides information of the selected crack leading edge candidate having the highest possibility of realization to the crack progress determination unit 117.

The crack progress determination unit 117 determines whether or not a crack will progress along the crack leading edge candidate based on the crack progress evaluation function. For example, the crack progress determination unit 117 determines, with respect to the crack leading edge candidate having the highest possibility of realization selected by the crack progress evaluation function evaluation unit 116, whether or not the crack will progress along the crack leading edge candidate. To be specific, when the crack progress evaluation function is calculated with $p=(\delta U_e)/(G_c \cdot s)$, the crack progress determination unit 117 determines whether or not the value of p corresponding to the selected crack leading edge candidate is equal to or greater than the threshold value D=1, and thereby determines whether or not the crack has progressed along the crack leading edge candidate. When the value of p is equal to or greater than D=1, the crack progress determination unit 117 determines that the crack has progressed along the crack leading edge candidate, and then provides information of the crack leading edge candidate to the analysis condition setting unit 111. On the other hand, when the value of p is smaller than D=1, the crack progress determination unit 117 determines that the crack has not progressed along the crack leading edge candidate, and notifies a user of information of the determination result and information that the analysis has ended by, for example, outputting the information to the output unit of the information processing apparatus 10 described above. As such, the crack progress determination unit 117 compares the value of the elastic energy release rate and the value of the total toughness energy (in other words, the value of the toughness energy necessary when the crack progresses to the crack leading edge candidate), and thereby can determine whether or not the crack will progress along the crack leading edge candidate.

The process performed by the crack progress determination unit 117 corresponds to the process of Step S119 in the crack progress analysis method according to the first embodiment shown in FIG. 3B or the process of Step S217 in the crack progress analysis method according to the second embodiment shown in FIG. 13B. Note that, when the form of the crack progress evaluation function is different, the crack progress determination unit 117 can appropriately determine whether or not the crack has progressed along the crack leading edge candidate using a method proper for the form of the crack progress evaluation function.

Note that, although the case in which the crack progress evaluation function evaluation unit 116 extracts a crack leading edge candidate having the highest possibility of realization and then the crack progress determination unit 117 determines whether or not a crack will progress along the crack leading edge candidate has been described in the above example, the order of the processes performed by the crack progress evaluation function evaluation unit 116 and the crack progress determination unit 117 may be reversed. In other words, the crack progress determination unit 117 may determine whether or not a crack will progress along a crack leading edge candidate with respect to each of crack leading edge candidates extracted by the crack leading edge candidate extraction unit 112, and then the crack progress evaluation function evaluation unit 116 may select the crack leading edge candidate having the highest possibility of realization from the crack leading edge candidates at which the crack has progressed. The order of the processes performed by the crack progress evaluation function evaluation unit 116 and the crack progress determination unit 117 may be appropriately set in consideration of, for example, calculation loads thereof, or the like.

When the crack progress determination unit 117 determines that the crack has progressed along the crack leading edge candidate and then provides information of the crack leading edge candidate to the analysis condition setting unit 111, the analysis condition setting unit 111 allows the crack to progress (in other words, opens nodes and meshes) in the structure so as to correspond to the crack leading edge candidate, and re-sets a new crack leading edge that includes the open portions as a calculation target. As such, the analysis condition setting unit 111 further performs the processes of Steps S121 and S125 in the crack progress analysis method according to the first embodiment shown in FIG. 3B or the processes of Steps S219 and S223 in the crack progress analysis method according to the second embodiment shown in FIG. 13B. The crack leading edge candidate extraction unit 112, the FEM calculation unit 113, the elastic energy release rate calculation unit 114, and the crack leading edge decision unit 118 repeat the same processes described above on the set new crack leading edge.

Here, the crack progress determination unit 117 may further determine the progress of the crack based on whether or not the crack has reached the end of the shape model in the stage in which the crack has progressed in the structure so as to correspond to the crack leading edge candidate by the analysis condition setting unit 111. When the crack has not reached the end of the shape model, the crack progress determination unit 117 determines that there is a possibility of the crack still progressing in that direction, instructs the analysis condition setting unit 111 to set the new crack leading edge for the shape model after the progress of the crack as a calculation target, and then causes the crack leading edge candidate extraction unit 112, the FEM calculation unit 113, the elastic energy release rate calculation unit 114, and the crack leading edge decision unit 118 to execute the analysis process on the new set crack leading edge candidate. On the other hand, when the crack has reached the end of the shape model, the crack progress determination unit 117 determines that the crack will no longer progress in that direction, and then notifies the user of the information of the determination result and information that the analysis has ended by, for example, outputting them to the output unit of the information processing apparatus 10 described above. As such, the crack progress determination unit 117 can further perform the process of Step S123 in the crack progress analysis method according to the first embodiment shown in FIG. 3B or the process of Step S221 in the crack progress analysis method according to the second embodiment shown in FIG. 13B.

Note that, even when the crack progress determination unit 117 determines that the crack will no longer progress in the second embodiment, if the analysis of the progress of the crack is of the analysis process of the first stage (in other words, the crack progress analysis process with respect to the surface layer region), the process continuously transitions to the analysis process of the second stage. Thus, when the crack progress determination unit 117 determines that the progress of the crack has stopped based on the crack progress evaluation function or whether or not the crack has reached the end of the shape mode, the crack progress determination unit further determines whether or not the currently performed analysis process is the crack progress analysis process with respect to the surface layer region, and when the currently performed analysis process is the crack progress analysis process with respect to the surface layer region, the crack progress determination unit can instruct the analysis condition setting unit 111 to set an analysis condition according to the analysis process of the second stage. On the other hand, when the currently performed analysis process is the crack progress analysis process with respect to the internal region that is the analysis process of the second stage, the crack progress determination unit outputs information that the series of crack progress analysis processes has ended to, for example, the output unit of the information processing apparatus 10 described above.

Hereinabove, the configuration of the information processing apparatus 10 for realizing the crack progress analysis methods according to the first and second embodiments has been described with reference to FIG. 21. As described above, in an embodiment of the present disclosure, when the crack leading edge candidate formed after the progress of the crack is extracted in the crack progress analysis process, the crack leading edge candidate that satisfies predetermined conditions is extracted from the crack leading edge candidates which can be obtained in terms of the construction of the structure. Thus, since the crack progress evaluation function p is calculated for the crack leading edge candidate that has been narrowed down based on the predetermined conditions, rather than for all of the crack leading edge candidates which can be obtained in terms of the structure, an overall calculation load can be reduced even when calculation with a relatively heavy calculation load caused by, for example, the FEM calculation imposed during computation of the crack progress evaluation function p is performed.

Note that a computer program for realizing each of the functions of the information processing apparatus 10 according to the first and second embodiments described above, particularly, each of the functions of the control unit 110, can be produced and installed in a PC or the like. In addition, a computer-readable recording medium on which the computer program is stored can also be provided. The recording medium is, for example, a magnetic disk, an optical disc, a magneto-optical disc, a flash memory, or the like. In addition, the computer program may be distributed via, for example, a network, rather than using the recording medium.

Herein, the functions of the information processing apparatus 10 are necessarily realized by a single information processing apparatus, but may be realized in cooperation with a plurality of information processing apparatuses connected to one another through a network. For example, when the functions of the control unit 110 illustrated in FIG. 21 as the functional blocks are implemented by control units of the plurality of information processing apparatuses connected to one another through a network, various calculation processes can be performed in parallel, and thereby further reduction of the calculation time can be realized. In addition, an input and output interface of the information processing apparatus 10 and other functions, for example, may be configured by individual devices. For example, a user terminal that at least includes an input unit and an output unit and a workstation specialized in numerical calculation may be connected to each other through a wired or wireless network so as to be communicable, input and output of various kinds of information to and from the workstation may be performed by a user using the user terminal, and various kinds of calculation performed by the control unit 110 during analysis of the progress of a crack may be performed by the workstation. The workstation can be arranged on, for example, a network (on a so-called cloud) that a user terminal can access. As such, by executing various arithmetic operations by a workstation specialized in numerical calculation, it is possible to execute crack progress analysis in a shorter period of time.

5. Modified Examples

Next, several modified examples according to the embodiments described above will be described.

(5-1. Crack Progress Analysis in Consideration of Anisotropy)

Figure 22:
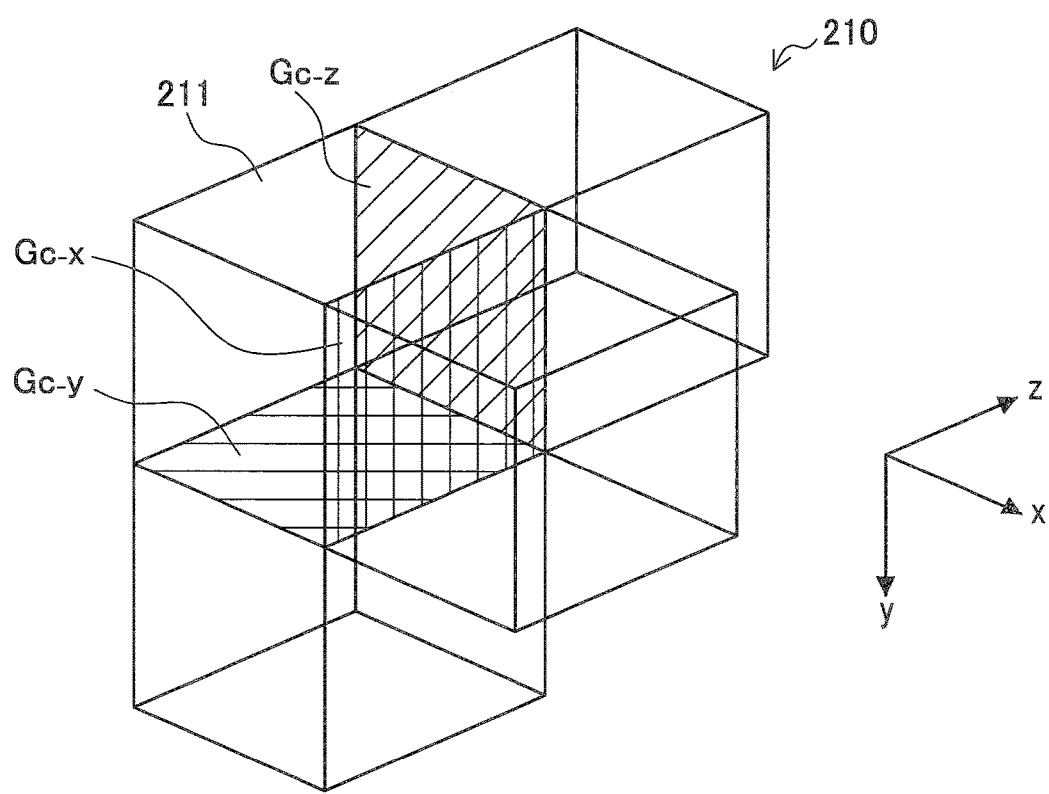
FIG. 22 is an illustrative diagram for describing a modified example in which anisotropy is considered in crack progress analysis according to the first and second embodiments.

In the first and second embodiments, crack progress analysis in consideration of anisotropy may be performed. A modified example of crack progress analysis according to the first and second embodiments considering anisotropy will be described with reference to FIG. 22. FIG. 22 is an illustrative diagram for describing the modified example in which anisotropy is considered in the crack progress analysis according to the first and second embodiments.

Referring to FIG. 22, a shape model 210 expressing an example of a structure to be analyzed according to the present modified example is illustrated. In the example shown in FIG. 22, the shape model 210 is constituted by a plurality of meshes 211 having cubic shapes. Here, in general, there are cases in which a material which is a crystalline material having strong anisotropy or a material formed by embedding fibrous materials in one direction has an anisotropic elastic modulus and an anisotropic toughness value. In the present modified example, when an elastic modulus and a toughness value are set for the shape model 210, the elastic modulus and the toughness value are set taking the anisotropy into consideration. Specifically, in the present modified example, toughness values of a structure according to binding force in each direction of the inside of the structure are set with respect to the directions. More specifically, in the present modified example, when the toughness values per unit area are set in the shape model 210, individual values are set in each direction of a surface of the meshes 211 constituting the shape model 210.

Setting anisotropy of an elastic modulus is widely performed in the general FEM, and can be set as, for example, an amount of tensors. When anisotropy of a toughness value is set, for example, toughness values of a material to be analyzed in each direction are calculated in advance based on experiments, tests, and the like, and the calculated values are set as the toughness values of each direction. For example, with respect to surfaces of the mesh 211, in the example shown in FIG. 22, the toughness value per unit area on a surface orthogonal to the x axis is set to $G_c\_x$, the toughness value per unit area on a surface orthogonal to the y axis is set to $G_c\_y$, and the toughness value per unit area on a surface orthogonal to the z axis is set to $G_c\_z$. $G_c\_x$, $G_c\_y$, and $G_c\_z$ may be, for example, experimentally obtained toughness values of a material constituting the structure in each direction. When the toughness values of the material have three-dimensionally different values, a different toughness value ($G_c\_x$, $G_c\_y$, and $G_c\_z$) can be given to each face according to normal vectors of the faces of the mesh 211 as shown in FIG. 22. As a specific method for setting toughness values, toughness values may be set as predetermined continuous functions so that toughness values can be elicited in all three-dimensional directions, or a toughness value is discretely set in each direction and a toughness value of a position corresponding to a gap may be interpolated with a predetermined function.

As such, by setting a toughness value of a structure according to binding force exerted in each direction of the inside of the structure in each of the directions, crack progress analysis of the structure in which the toughness values have anisotropy can be performed more accurately, and accordingly, convenience and adaptability of the crack progress analysis improve.

(5-2. Crack Progress Analysis in Consideration of an Interface Between Different Kinds of Materials)

Figure 23:
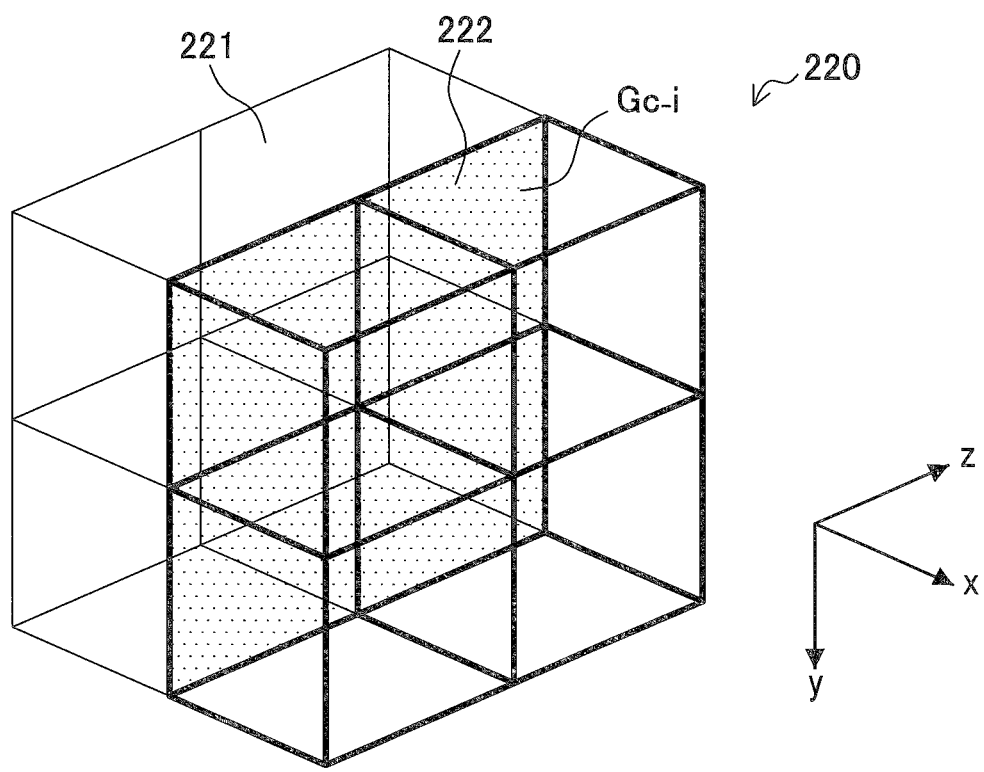
FIG. 23 is an illustrative diagram for describing a modified example in which an interface between different kinds of materials is considered in crack progress analysis according to the first and second embodiments.

In the first and second embodiments, crack progress analysis in consideration of an interface between different kinds of materials may be performed. A modified example of crack progress analysis according to the first and second embodiments considering an interface between different kinds of materials will be described with reference to FIG. 23. FIG. 23 is an illustrative diagram for describing the modified example in which an interface between different kinds of materials is considered in the crack progress analysis according to the first and second embodiments.

Referring to FIG. 23, a shape model 220 expressing an example of a structure to be analyzed according to the present modified example is illustrated. In the example shown in FIG. 23, the shape model 220 is constituted by a plurality of meshes 221 having cubic shapes. Here, the shape model 220 is composed of a combination of two different materials, and an interface 222 between the different kinds of materials is present on the boundary between the meshes 221, which distinguishes the different materials. There are cases with respect to an interface between different kinds of materials in which interface binding force (adherence force) of the interface is different from a toughness value of any material. Thus, in the present modified example, when a toughness value is set for the shape model 220, a toughness value corresponding to interface binding force is set for the interface 222.

Specifically, in the present modified example, when a toughness value per unit area is set for the shape model 220, a value can be individually set for a face corresponding to the interface between different kinds of materials. For example, for the interface 222 between a material 1 and a material 2 in the example shown in FIG. 23, a toughness value $G_c\_i$ corresponding to interface binding force thereof is set as a toughness value per unit area.

As such, when the structure is composed of a plurality of different materials in the present modified example, a toughness value according to binding force of each material is set for a region corresponding to the material of the structure, and a toughness value according to binding force of the interface between materials is set for a face corresponding to the interface between the different materials of the structure. When a toughness value is set for the structure, a toughness value is set taking the interface between different kinds of materials into account, and thus exfoliation occurring on the interface between the different kinds of materials can be analyzed more accurately, and thereby convenience and adaptability of crack progress analysis improve.

(5-3. Modified Example in which the Shape of Meshes is Different)

Figure 24A:
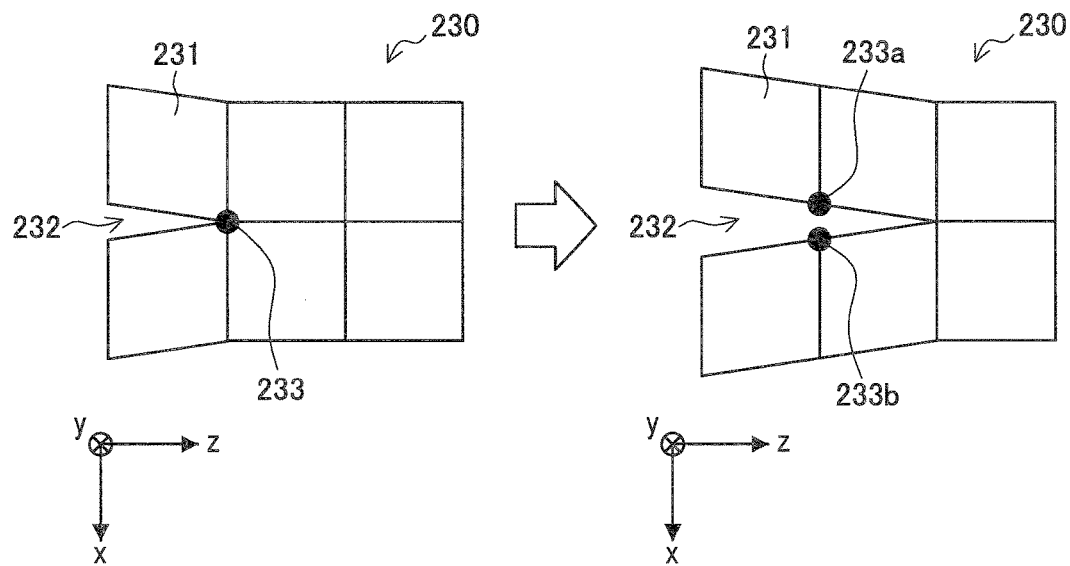
FIG. 24A is an illustrative diagram for describing a modified example in which the shape of meshes is different in crack progress analysis according to the first and second embodiments.
Figure 24B:
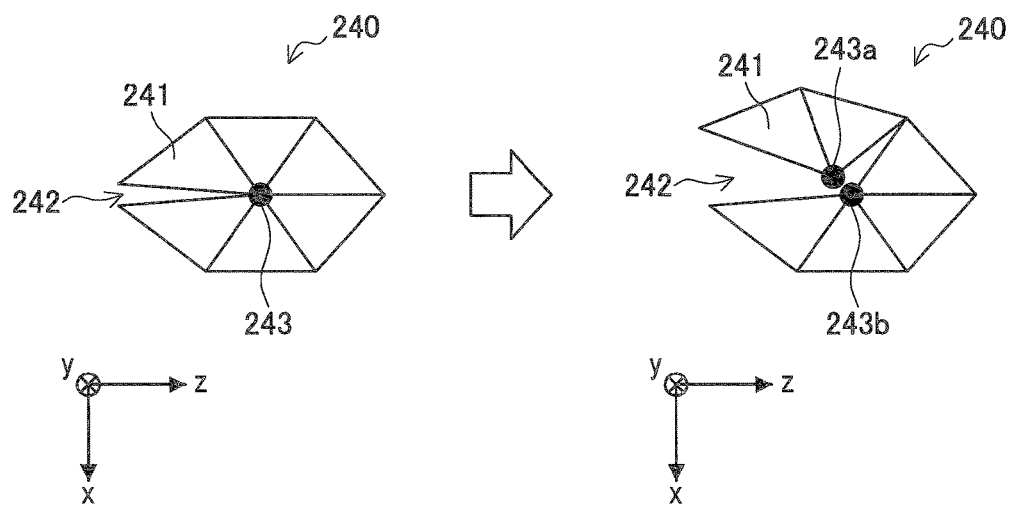
FIG. 24B is an illustrative diagram for describing a modified example in which the shape of meshes is different in crack progress analysis according to the first and second embodiments.

In the embodiments and modified examples described above, the shape of the meshes constituting the shape models is hexahedron. In the first and second embodiments, however, the shape of meshes constituting the shape model may be another shape. A modified example in which the shape of meshes is different in the crack progress analysis according to the first and second embodiments will be described with reference to FIGS. 24A and 24B. FIGS. 24A and 24B are illustrative diagrams for describing the modified example in which the shape of meshes is different in the crack progress analysis according to the first and second embodiments.

For the sake of simplification, FIGS. 24A and 24B only illustrate a cross section that includes a crack in a shape model to be analyzed. FIG. 24A illustrates the shape model 230 constituted by meshes 231 having a hexahedral shape as the shape models which have been describe so far. There is a crack 232 in the shape model 230, and a node 233 on a crack leading edge. When a crack leading edge candidate is extracted in the crack progress analysis according to the first and second embodiments, the meshes 231 are separated from each other at the node 233 and accordingly the crack progresses. The example shown in FIG. 24A illustrates the state in which the node 233 is separated into a node 233a and a node 233b, the meshes 231 are accordingly separated in the x-axis direction, and thereby the crack 232 progresses.

On the other hand, FIG. 24B illustrates a shape model 240 constituted by meshes 241 having a tetrahedron shape, different from the shape models which have been described so far. A crack 242 is present in the shape model 240, and a node 243 is present in a crack leading edge. In the crack progress analysis according to the first and second embodiments, when a crack leading edge candidate is extracted, the meshes 241 are separated at the node 243 and thus the crack progresses. The example shown in FIG. 24B illustrates the state in which the crack 242 progresses as the node 243 is separated into a node 243a and a node 243b and accordingly the meshes 241 are separated.

Note that the shape of the meshes according to the first and second embodiments is not limited to a tetrahedron or a hexahedron, and various other shapes used in the FEM may be applied. As such, since the crack progress analysis according to the first and second embodiments can be applied to a variety of shapes of meshes, even when the shape of meshes is limited to a specific shape due to, for example, a request from FEM calculation, the progress of a crack can be analyzed along the shape, and thus adaptability is enhanced.

(5-4. Crack Progress Analysis in Consideration of Internal Stress of a Material)

Figure 25:
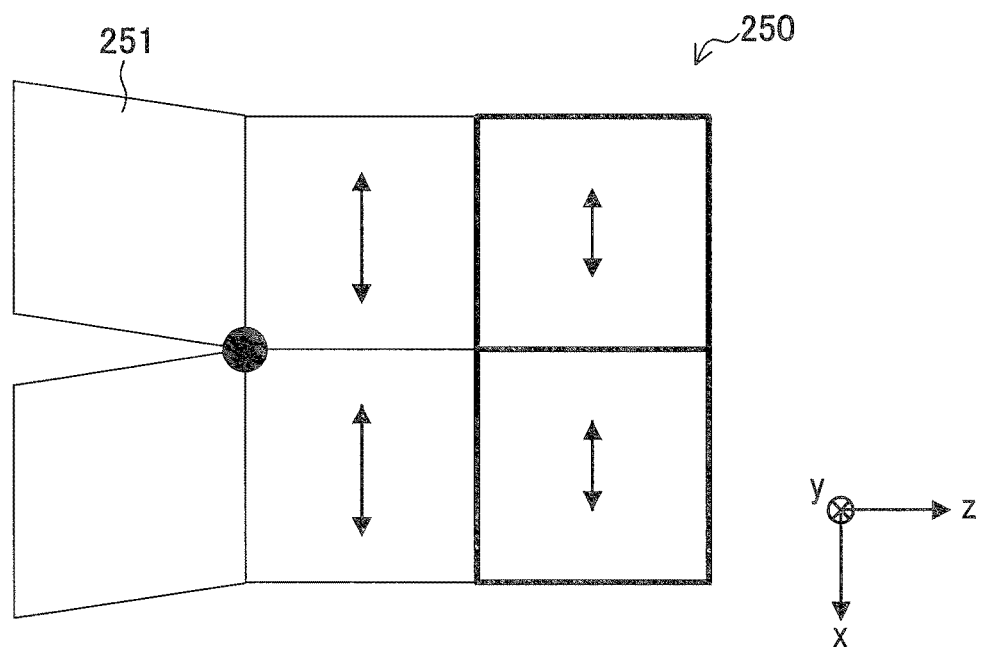
FIG. 25 is an illustrative diagram for describing a modified example in which internal stress of a material is considered in crack progress analysis according to the first and second embodiments.

A semiconductor device, for example, has a structure in which thin films formed of various materials are laminated, however, there are cases in which thermal stress occurs in each thin film according to a processing condition. In addition, there are cases in other structures, not limited to a semiconductor device, in which residual stress locally occurs according to a processing condition or the like. In the first and second embodiments, crack progress analysis that considers internal stress of a material as above may be performed. With reference to FIG. 25, a modified example in which internal stress of a material is considered in the crack progress analysis method according to the first and second embodiments will be described. FIG. 25 is an illustrative diagram for describing the modified example in which internal stress of a material is considered in the crack progress analysis method according to the first and second embodiments.

Referring to FIG. 25, a shape model 250 expressing an example of a structure to be analyzed according to the present modified example is illustrated. The example shown in FIG. 25 only illustrates a cross section that includes a crack in the shape model 250 to be analyzed for the sake of simplification. The shape model 250 is constituted by a plurality of meshes 251 having cubic shapes. The shape model 250 is composed of, for example, a plurality of different materials and physical property values corresponding to each of the materials are set for the meshes 251. In FIG. 25, in order to indicate different kinds of materials, contours of the meshes 251 are illustrated with fine lines and thick lines.

In the present modified example, internal stress present inside of each material such as thermal stress or residual stress described above, strain corresponding to the internal stress, or the like can be set for each mesh 251. As the internal stress, different values may be set for, for example, each material and each position. In FIG. 25, internal stress having different values set for each mesh 251 is schematically illustrated using, for example, double-headed arrows with different lengths. Note that setting of internal stress and strain accompanied by the internal stress may be made in, for example, the process of Step S103 of the flow shown in FIG. 3A or the process of Step S203 of the flow shown in FIG. 13A. In addition, after the stress and the strain are considered in addition to an external force factor condition, the stress is analyzed using the FEM, and thereby an elastic energy release rate is calculated.

As such, according to the present modified example, the internal stress according to a position inside the structure is set, and an elastic energy release rate can be calculated adding the set internal stress thereto. Therefore, the progress of a crack is analyzed in consideration of the internal stress such as thermal stress occurring during manufacturing of the structure, residual stress generated according to a processing condition, and the like in addition to the external force factor condition, and thereby analysis with higher accuracy can be executed.

(5-5. Two-Dimensional Crack Progress Analysis in Consideration of Three-Dimensional Anisotropy of Toughness)

As described in (5-1. Crack progress analysis in consideration of anisotropy) above, it is possible to create a shape model by reflecting three-dimensional anisotropy of toughness of a structure therein. Here, as described with reference to FIGS. 16A to 16F and 18A to 18E, for example, two-dimensional progress of the crack within the plane (x-z plane) parallel to the surface in the surface layer region of the shape model is analyzed as the analysis process of the first stage in the second embodiment described above, however, when three-dimensional anisotropy of toughness is set in the shape model, there is a possibility of thickness-direction (y-axis-direction) toughness affecting the two-dimensional progress of the crack in the x-z plane. Herein, a method which enables more accurate crack progress analysis by analyzing the two-dimensional progress of the crack within a plane considering three-dimensional anisotropy of toughness will be described.

Figure 26:
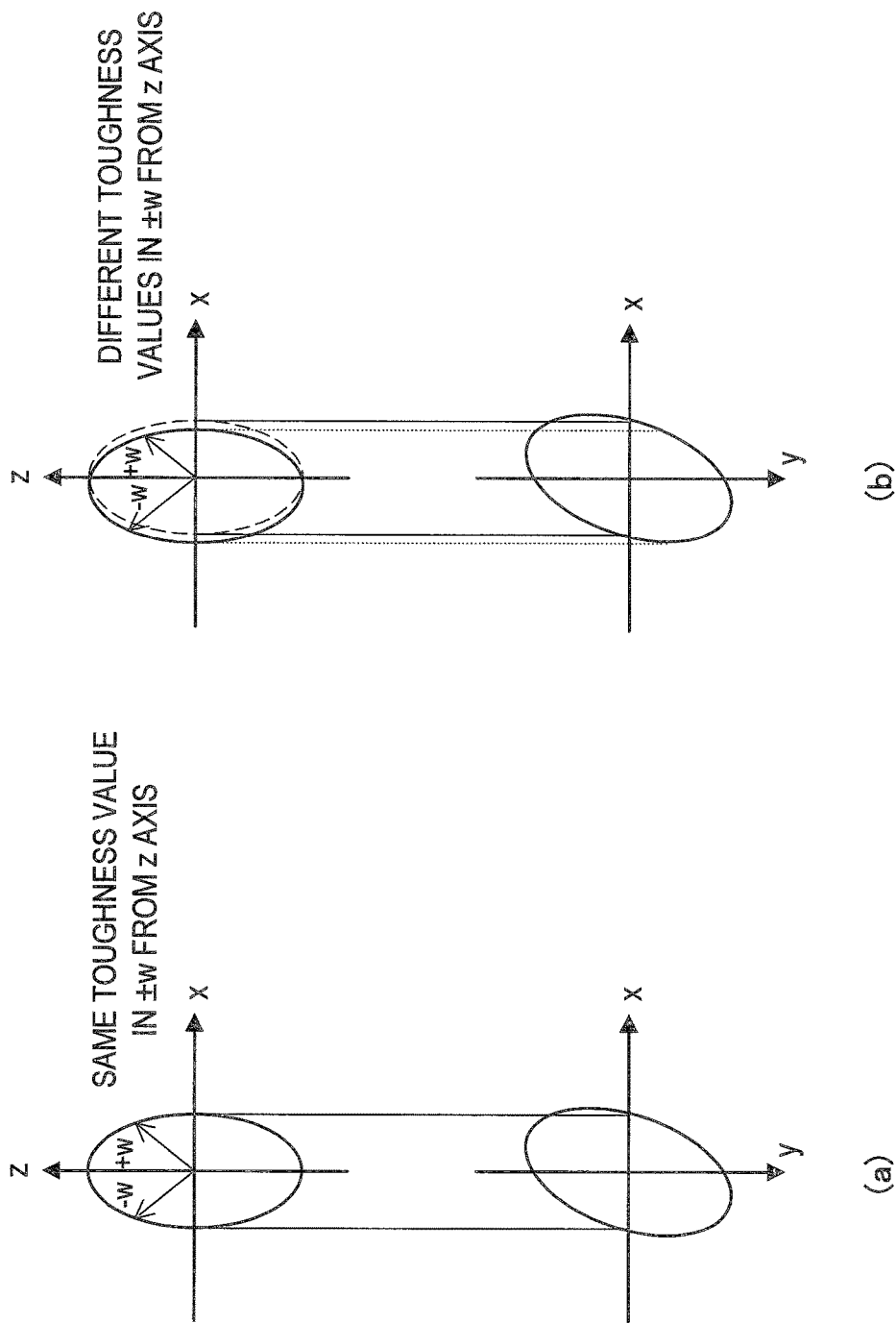
FIG. 26 is an illustrative diagram for describing two-dimensional crack progress analysis in which three-dimensional anisotropy of toughness is considered.
Figure 27:
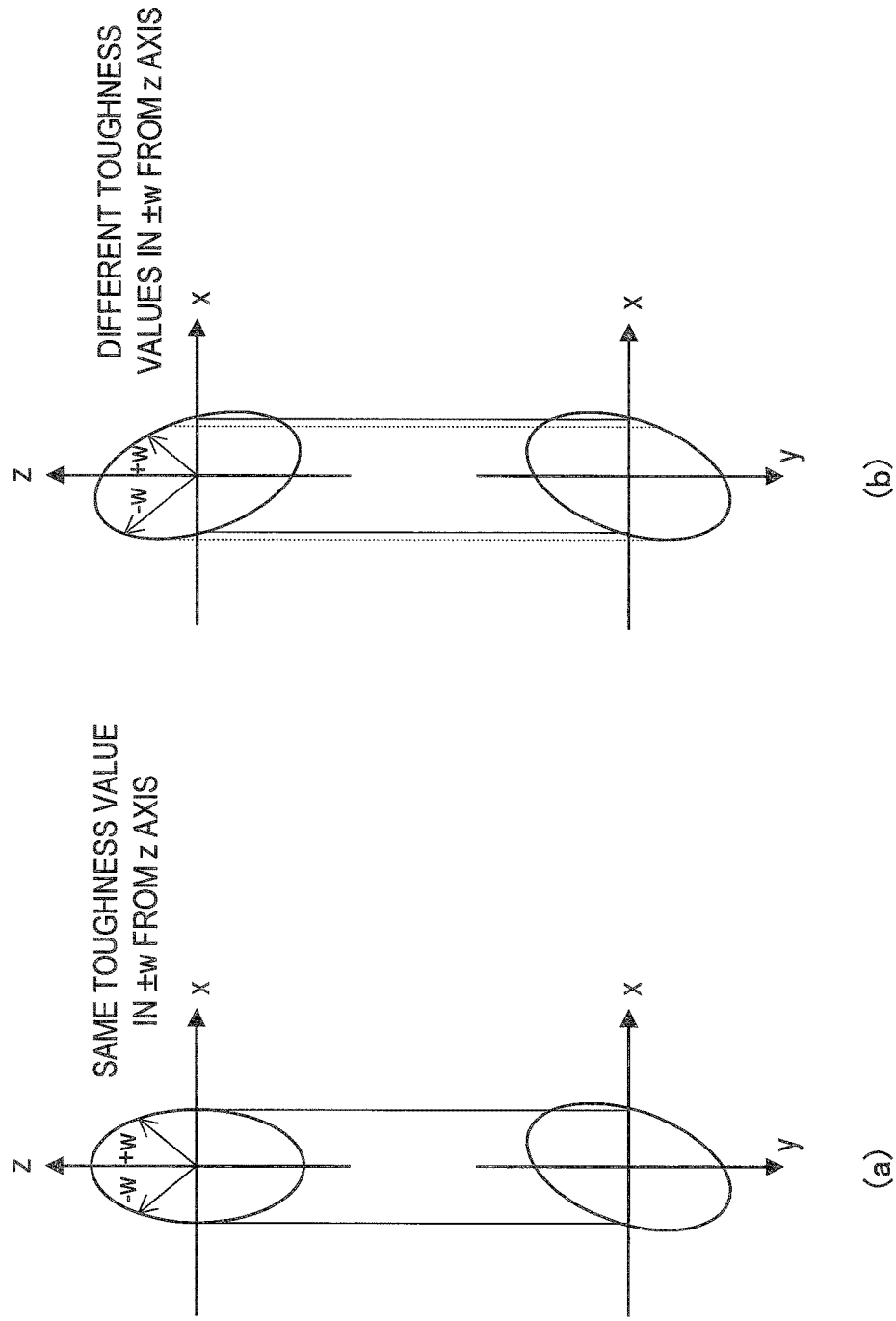
FIG. 27 is an illustrative diagram for describing two-dimensional crack progress analysis in which three-dimensional anisotropy of toughness is considered.

Two-dimensional crack progress analysis in consideration of three-dimensional anisotropy of toughness will be described with reference to FIGS. 26 and 27. FIGS. 26 and 27 are illustrative diagrams for describing two-dimensional crack progress analysis in which three-dimensional anisotropy of toughness is considered. Note that the x, y, and z axes shown in FIGS. 26 and 27 are based on the same definitions of the x, y, and z axes shown in, for example, FIGS. 16A to 16F, 18A to 18E, and the like. For example, the x-z plane indicates a face parallel to a surface of a shape model, and the y-axis direction indicates the thickness direction of the shape model.

In FIG. 26, a toughness value set in the shape model is schematically illustrated by combining x-y-z coordinates and ellipses. The distance from the origin to the circumference of an ellipse in a predetermined direction indicates the magnitude of a toughness value in that direction. In other words, the direction and length of an arrow (vector) extending from the origin to the circumference of the ellipse indicates the magnitude of the toughness value in that direction.

Here, a structure set as an analysis target is assumed to have three-dimensional anisotropy with respect to toughness values and the toughness values are assumed to be symmetric with respect to the x and z axes and asymmetric with respect to the y axis. In this case, the ellipse indicating the toughness values can be illustrated as being symmetric with respect to the x and z axes and asymmetric (tilting) with respect to the y axis as shown in FIG. 26(a).

Using the toughness values set as shown in FIG. 26(a), performing the crack progress analysis according to the second embodiment described above is considered. In this case, in the crack progress analysis with respect to the surface layer region that is the analysis process of the first stage, the crack is analyzed to be progressing in the direction parallel to the x-z plane, and thus the progress of the crack is analyzed using the toughness values symmetric with respect to the x and z axes as shown in the upper part of FIG. 26(a). For example, as shown in FIG. 26(a), the toughness values have the same value in ±w angle directions with respect to the z axis and a toughness energy necessary when the crack progresses in a predetermined distance in the +w direction and a toughness energy necessary when the crack progresses in a predetermined distance in the −w direction are the same as each other.

Although the crack progress analysis with respect to the surface layer region and the crack progress analysis with respect to the internal region are performed in stages herein in order to reduce a calculation load in the second embodiment, as a real phenomenon, progress of a crack in the surface layer region and progress of a crack in the internal region can occur in parallel. Thus, there is a possibility of the asymmetric property of the toughness values in the y-axis direction affecting the progress of the crack in the x-z plane. Hence, in order to analyze the progress of the crack more accurately, it is desirable to consider the asymmetric property of the toughness values in the y-axis direction that is the thickness direction of the shape model in the crack progress analysis with respect to the surface layer region.

Specifically, a projection component of the distribution of the toughness values in the y-axis direction on the x-z plane is given to distribution of the toughness values within the x-z plane as an offset component in the x-axis direction as shown in FIG. 26(b) in the present modified example. Accordingly, the toughness values within the x-z plane are asymmetric with respect to the z-axis direction and the toughness values in the ±w angle directions with respect to the z axis become different from each other for which the distribution of the toughness values in the thickness direction is considered. As such, by analyzing the progress of the crack with respect to the surface layer region using the toughness values set in consideration of the influence of the asymmetric property of the anisotropic toughness in the thickness direction, three-dimensional progress of the crack can be analyzed with higher accuracy.

Herein, although the distribution of the toughness values within the x-z plane is offset by the projection component of the distribution of the toughness values in the y-axis direction on the x-z plane in FIG. 26(b), the present modified example is not limited thereto. In the present modified example, the influence of the distribution of the toughness values in the y-axis direction may be reflected on the distribution of the toughness values within the x-z plane using a method different from the method shown in FIG. 26. With reference to FIG. 27, a method of reflecting the influence of the distribution of the toughness values in the y-axis direction on the distribution of the toughness values within the x-z plane using a method different from the method shown in FIG. 26 will be described.

FIG. 27 also schematically illustrates anisotropy of toughness values by combining x-y-z coordinates and ellipses as in FIG. 26. Note that, since the drawing shown in FIG. 27(a) is the same as that shown in FIG. 26(a), detailed description thereof will be omitted.

As shown in FIG. 27(b), in the present modified example, the distribution of the toughness values within the x-z plane may be set so that an ellipse indicating the distribution of the toughness values within the x-z plane tilts to the extent of the projection component of the distribution of the toughness values in the y-axis direction on the x-z plane. Even when the distribution of the toughness values is set as above, the asymmetric property of the toughness values in the y-axis direction is reflected on the distribution of the toughness values within the x-z plane, and thus the toughness values in the ±w angle directions with respect to the z-axis become different from each other for which the distribution of the toughness values in the thickness direction is considered. Thus, as in the case shown in FIG. 26, the progress of the crack with respect to the surface layer region can be analyzed using the toughness values set in consideration of the influence of the asymmetric property in the thickness direction, and thereby three-dimensional progress of the crack can be analyzed with higher accuracy.

(5-6. Crack Progress Analysis when an External Force Factor Condition Changes)

As described above, in the first and second embodiments, when the elastic energy release rate $\delta U_e$ is computed, FEM calculation is performed under a predetermined external force factor condition (refer to the process of Step S113 shown in FIG. 3A and the process of Step S211 shown in FIG. 13A). Here, in the above embodiments, while the series of crack progress analysis processes is performed, for example, the predetermined external force factor condition can be set. Under a situation in which a crack actually occurs in a structure, however, a case in which, for example, external force exerted on the structure gradually changes as time elapses is also considered.

Figure 28:
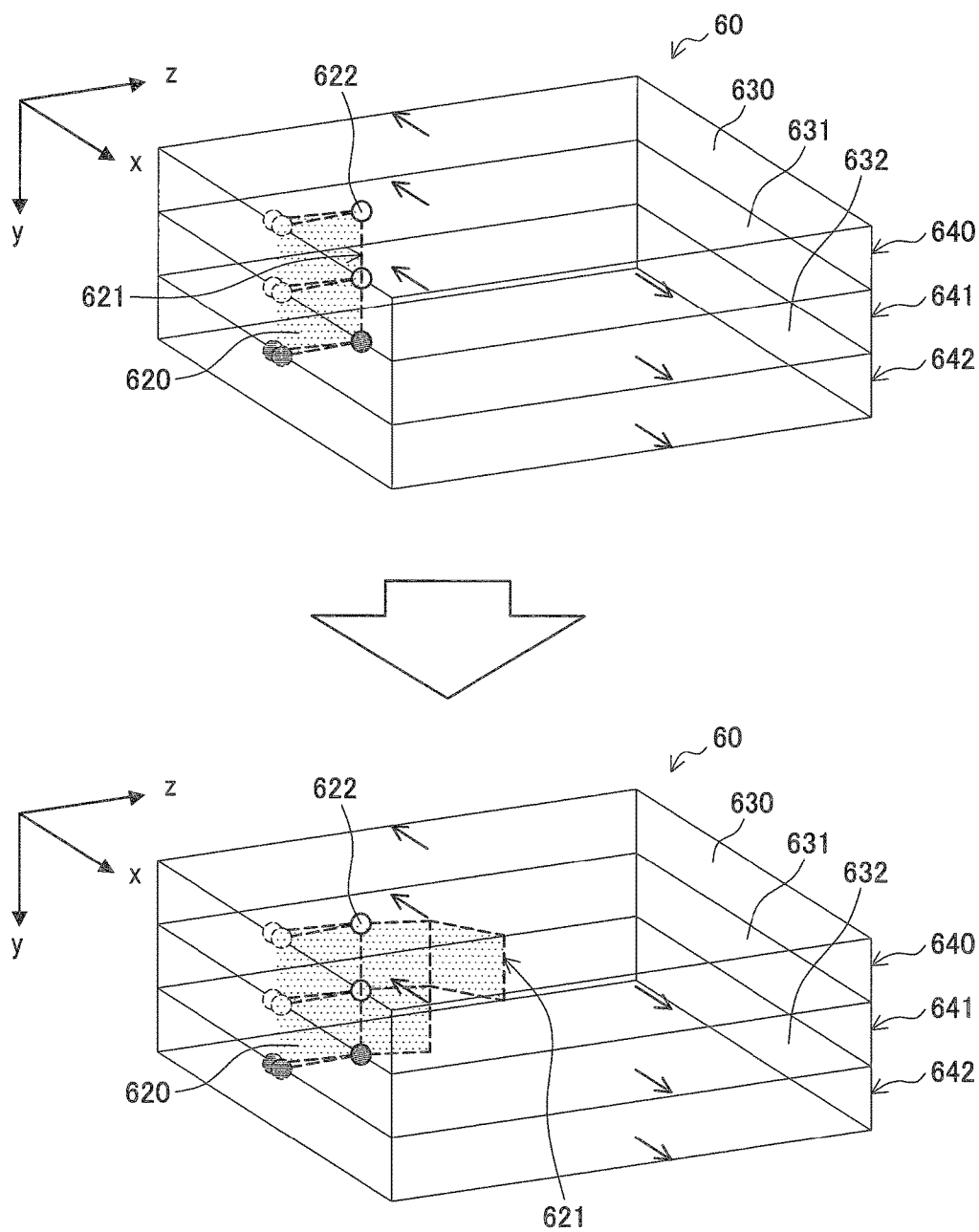
FIG. 28 is an illustrative diagram for describing crack progress analysis performed when an external force factor condition changes temporally.
Figure 29:
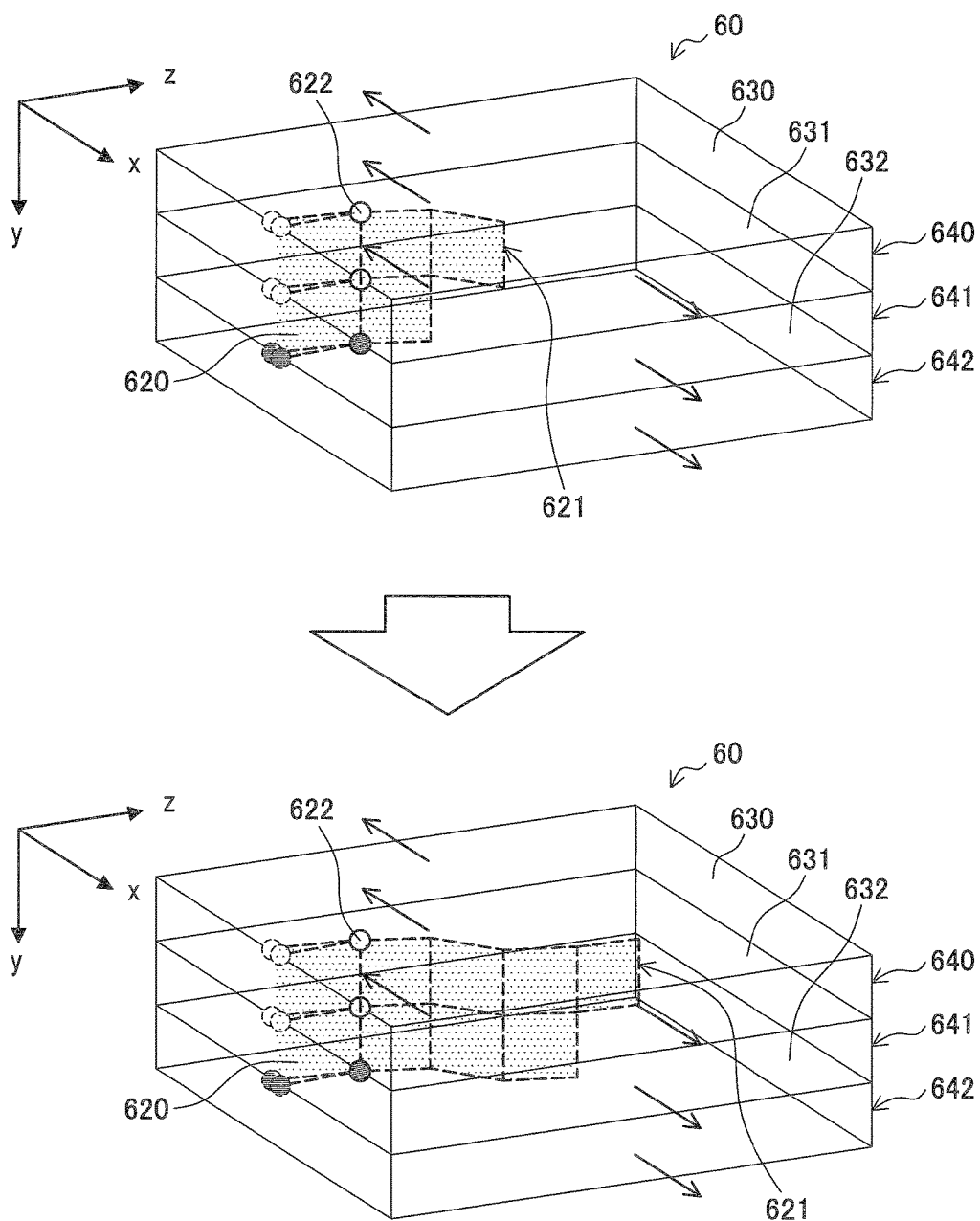
FIG. 29 is an illustrative diagram for describing crack progress analysis performed when an external force factor condition changes temporally.

With reference to FIGS. 28 and 29, crack progress analysis in such a case in which an external force factor condition temporally changes will be described. FIGS. 28 and 29 are illustrative diagrams for describing crack progress analysis performed when an external force factor condition temporally changes. Note that FIGS. 28 and 29 will be described exemplifying the case in which crack progress analysis is performed on the shape model 60 and the initial crack leading edge 621 shown in FIG. 17 as an example.

FIGS. 28 and 29 schematically illustrate the magnitude and orientation of external force exerted on the shape model 60 during the crack progress analysis process using the length and the direction of arrows. For example, a case in which tensile force is exerted on the shape model 60 in the x-axis direction as external force and the external force gradually increases is assumed. In this case, first, the crack progress analysis method according to the first embodiment (the series of processes shown in FIGS. 3A and 3B) or the crack progress analysis method according to the second embodiment (the series of processes shown in FIGS. 13A, 13B, and 14) is executed in the state in which the magnitude of the external force is relatively small as shown in FIG. 28. FIGS. 28 and 29 illustrate the case in which the crack progress analysis method according to the second embodiment is executed as an example. Specifically, in the state in which relatively small tensile force is set in the x-axis direction of the shape model 60 as an external force factor condition as shown in FIG. 28, FEM calculation is performed for the shape model 60, and the elastic energy release rate $\delta U_e$ is computed. Then, the crack progress evaluation function p is computed using the elastic energy release rate $\delta U_e$, and thereby the progress of the crack is analyzed.

As a result of executing the crack progress analysis method according to the second embodiment in the state in which the magnitude of the external force exerted on the shape model 60 is relatively small until the progress of the crack stops, the crack face 620 is assumed to progress from the state shown in the upper part of FIG. 28 to the state shown in the lower part. When the external force factor condition does not change, the analysis of the progress of the crack ends in that state, however, when the external force factor condition changes, the values of the elastic energy release rate $\delta U_e$ and the crack progress evaluation function p can change according to the change of the external force factor condition, and thus there is a possibility of the crack further progressing.

Thus, in the present modified example, the state shown in the lower part of FIG. 28 (in other words, the state in which the progress of the crack face 620 stops with relatively small external force exerted thereon) is regarded as the initial state of the crack face 620 and the crack progress analysis method according to the first embodiment (the series of processes shown in FIGS. 3A and 3B) or the crack progress analysis method according to the second embodiment (the series of processes shown in FIGS. 13A, 13B, and 14) is executed again in the state in which the relatively large external force is exerted as shown in the upper part of FIG. 29. The example shown in FIG. 29 illustrates the case in which the crack progress analysis method according to the second embodiment is continuously executed.

The external force shown in FIG. 29 is obtained by reproducing a change of the external force exerted on the shape model 60 after a predetermined period of time elapses. As a result of executing the crack progress analysis method according to the second embodiment until the progress of the crack stops, for example, the crack face 620 is assumed to progress from the state shown in the upper part of FIG. 29 to the state shown in the lower part. The crack face 620 shown in the lower part of FIG. 29 can be said to show a transient response of the progress of the crack when the external force exerted on the shape model 60 changes.

Hereinabove, the crack progress analysis when the external force factor condition temporally changes has been described with reference to FIGS. 28 and 29. As described above, by continuously executing the crack progress analysis process while changing the external force factor condition and using the three-dimensional shape of the crack formed based on the external force factor condition as an initial condition of the external force factor condition, it is possible to perform highly accurate crack progress analysis in which a temporal change of the external force factor condition is considered.

Note that, in the above-described example, although the case in which the magnitude of the external force changes has been described, the present modified example is not limited thereto. For example, even when other elements such as the direction in which external force is exerted temporally change, the crack progress analysis in which a temporal change of the external force factor condition is considered can be performed using the same method. In addition, it is possible to demonstrate the progress when the external force factor condition continuously changes by discretely setting a temporal change of the external force factor condition in a predetermined unit time.

6. Hardware Configuration

Figure 30:
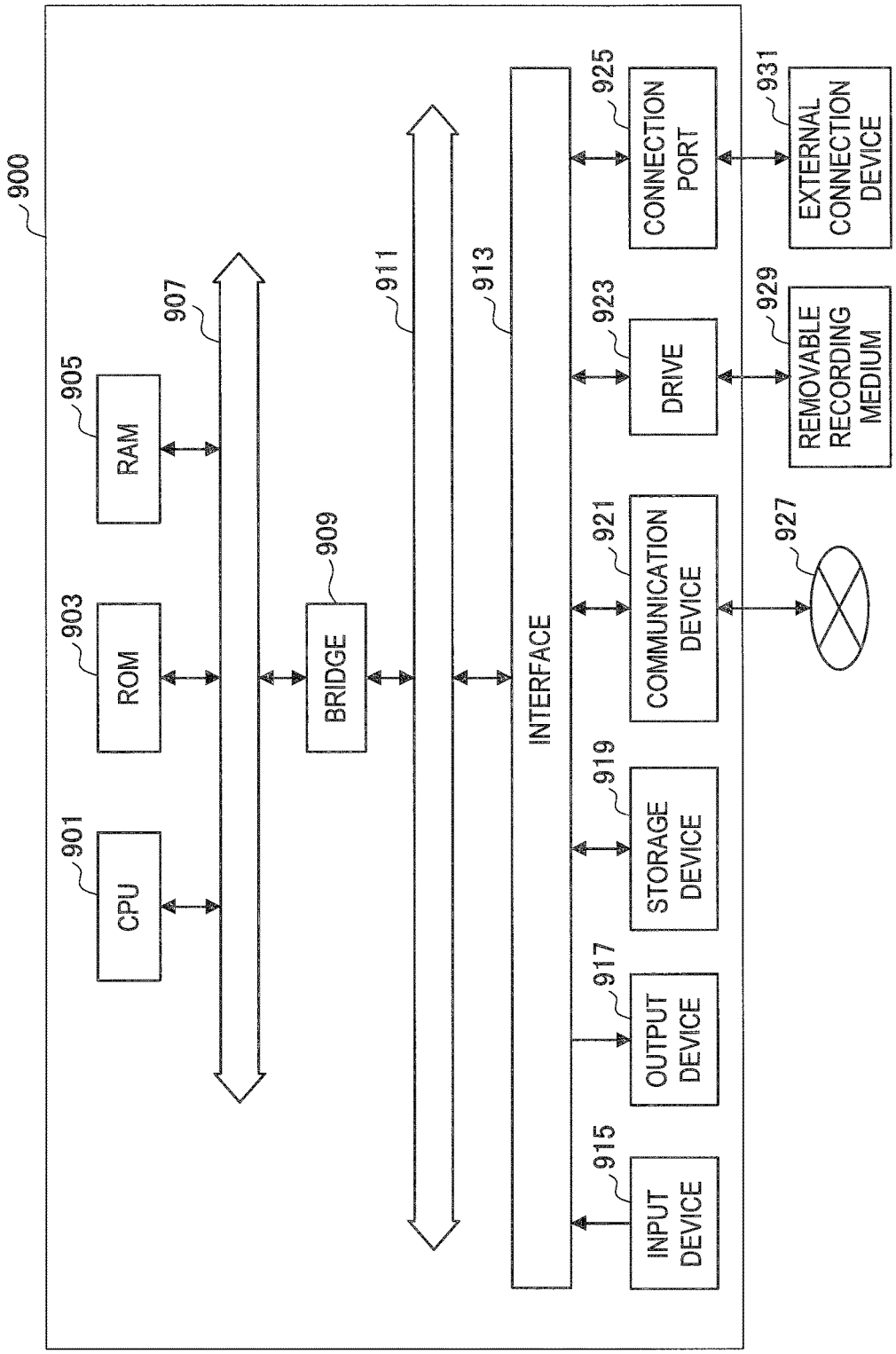
FIG. 30 is a block diagram for describing a hardware configuration of the information processing apparatuses according to the first and second embodiments.

Next, a hardware configuration of the information processing apparatus according to the first and second embodiments will be described with reference to FIG. 30. FIG. 30 is a block diagram for describing the hardware configuration of the information processing apparatus according to the first and second embodiments. Note that the information processing apparatus 900 shown in FIG. 30 can realize, for example, the information processing apparatus 10 shown in FIG. 21.

The information processing apparatus 900 includes a CPU 901, read only memory (ROM) 903, and random access memory (RAM) 905. The information processing apparatus 900 may further include a host bus 907, a bridge 909, an external bus 911, an interface 913, an input device 915, an output device 917, a storage device 919, a communication device 921, a drive 923, and a connection port 925. The information processing apparatus 900 may include, instead of or along with the CPU 901, a processing circuit such as a digital signal processor (DSP) or an application specific integrated circuit (ASIC).

The CPU 901 functions as an arithmetic processing unit and a control unit and controls an entire operation or a part of the operation of the information processing apparatus 900 according to various programs recorded in the ROM 903, the RAM 905, the storage device 919, or a removable recording medium 929. The ROM 903 stores programs and arithmetic parameters used by the CPU 901. The RAM 905 temporarily stores programs used in execution of the CPU 901 and parameters and the like used during the execution. The CPU 901, the ROM 903, and the RAM 905 are connected to each other via the host bus 907 configured from an internal bus such as a CPU bus or the like. In addition, the host bus 907 is connected to the external bus 911 such as a peripheral component interconnect/interface (PCI) bus via the bridge 909. The CPU 901 corresponds to the control unit 110 of the information processing apparatus 10 described above, for example.

The host bus 907 is connected to the external bus 911 such as a PCI (Peripheral Component Interconnect/Interface) bus via the bridge 904.

The input device 915 is configured by a device operated by a user, such as a mouse, a keyboard, a touch panel, buttons, a switch, and a lever. Also, the input device 915 may be a remote control device using, for example, infrared light or other radio waves, or may be an external connection device 931 such as a mobile phone or a PDA compatible with the operation of the information processing apparatus 900. The input device 915 includes an input control circuit that generates an input signal on the basis of information inputted by the user by use of the above described operation means and outputs the input signal to the CPU 901, for example. The user of the information processing apparatus 900 can input various kinds of data to the information processing apparatus 900 and can instruct the information processing apparatus 900 to perform a processing operation by operating the input device 915. According to the first and second embodiments, for example, the input device 915 corresponds to the input unit (not shown in FIG. 21) of the information processing apparatus 10 described above. In the first and second embodiments, a user may input, for example, various kinds of information and instruction relating to crack progress analysis (for example, information of an analysis condition, an instruction of a start of analysis, and the like) to the information processing apparatus 900 via the input device 915.

The output device 917 is configured by a device capable of visually or aurally notifying the user of acquired information. For example, the output device 917 may be a display device such as a CRT display, a liquid crystal display, a plasma display, an EL display, or a lamp; an audio output device such as a speaker and headphones; or a printer. The output device 917 outputs results obtained by the processing performed by the information processing apparatus 900, for example. Specifically, the display device displays visually the results obtained by the processing performed by the information processing apparatus 900 in any of various forms such as a text, an image, a table, and a graph. According to the first and second embodiments, for example, the display device corresponds to the output unit (not shown in FIG. 21) of the information processing apparatus 10 described above. In the first and second embodiments, a setting screen for setting an analysis condition for crack progress analysis or a result display screen on which an analysis result is displayed may be displayed on the display device. On the other hand, the audio output device outputs aurally an audio signal such as reproduced sound data or acoustic data being converted into an analog signal.

The storage device 919 is a device for storing data configured as an example of a storage unit of the information processing apparatus 900. The storage device 919 is configured by, for example, a magnetic storage device such as a hard disk drive (HDD), a semiconductor storage device, an optical storage device, or a magneto-optical storage device. This storage device 919 stores programs to be executed by the CPU 901, various data, and various data obtained from the outside. According to the first and second embodiments, for example, the storage device 919 corresponds to the storage unit (not shown in FIG. 21) of the information processing apparatus 10 described above. According to the first and second embodiments, the storage device 919 may store various pieces of information processed in the flow charts shown in FIGS. 3A and 3B, for example.

The communication device 921 is a communication interface configured by, for example, a communication device for establishing a connection to a communication network 927. The communication device 921 is, for example, a wired or wireless local area network (LAN), Bluetooth (registered trademark), a communication card for wireless USB (WUSB), or the like. Alternatively, the communication device 921 may be a router for optical communication, a router for asymmetric digital subscriber line (ADSL), a modem for various communications, or the like. The communication device 921 can transmit and receive signals and the like using a given protocol such as TCP/IP on the Internet and with other communication devices, for example. The network 927 connected to the communication device 921 is configured by a network and the like, which is connected via wire or wirelessly, and is, for example, the Internet, a home-use LAN, infrared communication, radio wave communication, and satellite communication. According to the first and second embodiments, for example, the communication device 921 corresponds to the communication unit (not shown in FIG. 21) of the information processing apparatus 10 described above. According to the first and second embodiments, for example, various pieces of information processed in the flow charts shown in FIGS. 3A and 3B can be transmitted and received between or among apparatuses through the network 927 by the communication device 921.

The drive 923 is a reader/writer for the removable recording medium and is built in or externally attached to the information processing apparatus 900. The drive 923 reads out information recorded on the attached removable recording medium 929, such as a magnetic disk, an optical disk, a magneto-optical disk, or a semiconductor memory, and outputs the information to the RAM 905. Further, the drive 923 can write information on the attached removable recording medium 929, such as a magnetic disk, an optical disc, a magneto-optical disk, or a semiconductor memory. Examples of the removable recording medium 929 include a DVD medium, an HD-DVD medium, a Blu-ray (registered trademark) medium. Alternatively, the removable recording medium 929 may be a Compact Flash (CF, registered trademark), a flash memory, a secure digital memory card (SD memory card), or the like. Further alternatively, the removable recording medium 929 may be, for example, an integrated circuit card (IC card) on which a contactless IC chip is mounted, an electronic device, or the like. According to the first and second embodiments, for example, various pieces of information processed in the flow charts regarding the first embodiment shown in FIGS. 3A and 3B, and various pieces of information processed in the flow charts regarding the second embodiment shown in FIGS. 13A, 13B, and 14 may be read out from the removable recording medium 929 or written into the removable recording medium 929 by the drive 923.

The connection port 925 is a port for allowing devices to directly connect to the information processing apparatus 900. Examples of the connection port 925 include a universal serial bus (USB) port, an IEEE1394 port, and a small computer system interface (SCSI) port. Other examples of the connection port 925 may include an RS-232C port, an optical audio terminal, and a high-definition multimedia interface (HDMI, registered trademark) port. The connection of the external connection device 931 to the connection port 925 may enable the various data to be obtained directly from the external connection device 931 or to be provided to the external connection device 931. According to the first and second embodiments, for example, various pieces of information processed in the flow charts shown in FIGS. 3A and 3B, and various pieces of information processed in the flow charts regarding the second embodiment shown in FIGS. 13A, 13B, and 14 may be obtained from the external connection device 931 or outputted to the external connection device 931 via the connection port 925.

The example of the hardware configuration that can realize the functions of the information processing apparatus 900 according to an embodiment of the present disclosure has been described above. Each structural element described above may be formed by a common member or configured by hardware having a special function of each structural element. Accordingly, it is possible to change the hardware configuration to be used as appropriate depending on technique levels when the present embodiment is executed.

Note that it is possible to create a computer program for realizing each function of the above described information processing apparatus 900 according to the present embodiment and to incorporate the program in a PC or the like. Further, it is possible to provide a computer-readable recording medium having such a computer program stored therein. The recording medium may be, for example, a magnetic disk, an optical disk, a magneto-optical disk, or a flash memory. Further, the computer program may be distributed through a network, for example, without using the recoding medium.

7. Supplement

As described above, when a crack leading edge candidate after the progress of the crack is extracted in the crack progress analysis process of an embodiment of the present disclosure, a crack leading edge candidate that satisfies the predetermined conditions is extracted from the crack leading edge candidates which can be obtained in terms of the construction of the structure. Thus, since the crack progress evaluation function p is calculated for the crack leading edge candidate that has been narrowed down based on the predetermined conditions, rather than for all of the crack leading edge candidates which can be obtained in terms of the structure, an overall calculation load can be reduced even when calculation with a relatively heavy calculation load caused by, for example, the FEM calculation imposed during computation of the crack progress evaluation function p is performed.

To be specific, in the first embodiment, a total toughness energy that is an energy necessary when a crack progresses for one session is set, and a crack leading edge candidate formed one session later which is appropriate for the total toughness energy is extracted. Then, an elastic energy release rate $\delta U_e$ and a crack progress evaluation function p are calculated with respect to the extracted crack leading edge candidate. As such, in the first embodiment, by calculating the elastic energy release rate $\delta U_e$ for the crack leading edge candidate extracted based on the total toughness energy, it is possible to calculate the elastic energy release rate $\delta U_e$ targeting opening of a plurality of nodes and meshes. Therefore, in comparison to a case in which opening of each node one by one is targeted which is generally performed, the number of calculations of the elastic energy release rate $\delta U_e$, which are accompanied by FEM calculation having a heavy calculation load, can be reduced, and accordingly, reduction of the calculation load is realized.

In addition, in the second embodiment, the crack leading edge candidates obtained when the crack progresses in the surface layer region of the structure are extracted as the analysis process of the first stage, and after the analysis process of the first stage ends, the crack leading edge candidates obtained when the crack progresses in the internal region of the structure are extracted based on the crack in the surface layer region obtained as a result of the analysis process of the first stage as the analysis process of the second stage. As such, since the crack leading edge candidate which has been narrowed down based on the result of the crack progress analysis process with respect to the surface layer region is extracted in the crack progress analysis process with respect to the internal region in the second embodiment, it is possible to reduce the number of calculations of the elastic energy release rate $\delta U_e$, which are accompanied by the FEM calculation having a heavy calculation load, in comparison with a general method in which analysis is performed on all nodes that can be obtained in terms of the structure. Therefore, the calculation load can be lessened.

Herein, the crack progress analysis method that uses the elastic energy release rate $\delta U_e$ is a method with high adaptability that can be applied to, for example, analysis of a crack in a structure composed of different kinds of materials and also to analysis of exfoliation of different kinds of materials on interfaces thereof. Therefore, in the first and second embodiments, crack progress analysis with a lighter calculation load is realized while maintaining high adaptability.

For example, in order to perform analysis of a three-dimensional crack of a structure composed of a plurality of different materials using the concept of the elastic energy release rate $\delta U_e$ in an existing general technology, an enormous period of calculation time is necessary. On the other hand, in the first and second embodiments, since a calculation load is further reduced while maintaining high adaptability, a three-dimensionally progressing crack penetrating different kinds of materials in a structure composed of, for example, a plurality of different materials can be analyzed faster.

In addition, in order to reduce a calculation load in the existing general technology, for example, there are cases in which a target face on which the progress of a crack is to be analyzed is uniformly decided in advance. For this reason, in the general technology, it is difficult to respond to cases in which whether a crack is progressing inside a material of a structure composed of a plurality of different materials, or a crack (i.e., exfoliation) is progressing between materials is unclear. On the other hand, in the first and second embodiments, since a calculation load is further reduced while maintaining high adaptability, it is not necessary to limit an analysis target face, and analysis can be performed even on a crack progressing direction. Thus, in a structure composed of a plurality of different materials, it is possible to three-dimensionally analyze the progress of a crack inside a material and progress of exfoliation occurring between materials at the same time.

Hereinabove, the exemplary embodiments of the present disclosure have been described in detail with reference to the accompanying drawings, however, the technical scope of the present disclosure is not limited thereto. It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to the present disclosure can exhibit other effects that are evident to those skilled in the art based on the present specification along with or instead of the effects.

Additionally, the present technology may also be configured as below.

(1) An information processing apparatus including:
a crack leading edge candidate extraction unit configured to extract a crack leading edge candidate after progress of a crack in a structure;
an elastic energy release rate calculation unit configured to calculate an elastic energy release rate that indicates an elastic energy released when the crack progresses to the extracted crack leading edge candidate; and
a crack leading edge decision unit configured to decide a crack leading edge after the progress of the crack at least based on the elastic energy release rate,
wherein the crack leading edge candidate extraction unit extracts the crack leading edge candidate that satisfies a predetermined condition from crack leading edge candidates obtained in terms of a construction of the structure.

(2) The information processing apparatus according to (1), wherein the crack leading edge candidate extraction unit extracts the crack leading edge candidate of which a total toughness energy necessary for separating a plurality of meshes constituting the structure when the crack progresses falls within a predetermined range.

(3) The information processing apparatus according to (2), wherein the crack leading edge candidate extraction unit extracts the crack leading edge candidate in a manner that the distance between adjacent meshes among the plurality of meshes constituting the crack leading edge after the progress of the crack has a value equal to or smaller than a predetermined value.

(4) The information processing apparatus according to (2) or (3), wherein the crack leading edge candidate extraction unit extracts the crack leading edge candidate in a manner that there is no region in which the meshes are combined within a plane in which the crack leading edge formed before the progress of the crack is connected to the crack leading edge formed after the progress of the crack in the shortest distance.

(5) The information processing apparatus according to (1),
wherein the crack leading edge candidate extraction unit extracts the crack leading edge candidate when the crack progresses in a surface layer region of the structure as an analysis process of the first stage, and
wherein, after the analysis process of the first stage ends, the crack leading edge candidate extraction unit extracts the crack leading edge candidate when the crack progresses in an internal region of the structure based on the crack occurring in the surface layer region obtained as a result of the analysis process of the first stage as an analysis process of a second stage.

(6) The information processing apparatus according to (5), wherein the crack leading edge candidate extraction unit extracts the crack leading edge candidate by searching for an angle formed within a face parallel to a surface of the structure from the crack leading edge before the progress of the crack in the analysis process of the first stage.

(7) The information processing apparatus according to (5) or (6), wherein the crack leading edge candidate extraction unit extracts the crack leading edge candidate by searching for an angle formed within an evaluation face that passes nodes and is substantially perpendicular to the surface of the structure from the nodes on the crack in the surface layer region obtained through the analysis process of the first stage in the analysis process of the second stage.

(8) The information processing apparatus according to any one of (5) to (7), wherein the progress of the crack on the surface of the structure is analyzed in the analysis process of the first stage.

(9) The information processing apparatus according to any one of (5) to (7), wherein the progress of the crack in a surface layer which includes a surface of the structure and is present at a predetermined depth from the surface is analyzed in the analysis process of the first stage.

(10) The information processing apparatus according to any one of (1) to (9), wherein the structure is composed of a plurality of different materials.

(11) The information processing apparatus according to (10),
wherein, for a region corresponding to each material of the structure, a toughness value according to binding force of the material is set, and
wherein, for a face corresponding to an interface between different materials of the structure, a toughness value according to binding force of the interface between the materials is set.

(12) The information processing apparatus according to any one of (1) to (11),
wherein internal stress according to a position inside the structure is set for the structure, and
wherein the elastic energy release rate calculation unit calculates the elastic energy release rate in consideration of the internal stress.

(13) The information processing apparatus according to any one of (1) to (12),
wherein a toughness value according to binding force inside the structure exerted in each direction is set for each direction in the structure, and
wherein the crack leading edge candidate extraction unit extracts the crack leading edge based on a crack progressing direction and a toughness value set for each direction inside the structure.

(14) The information processing apparatus according to any one of (1) to (13), wherein the elastic energy release rate calculation unit calculates the elastic energy release rate based on a result of analysis of stress on the structure using a finite element method.

(15) The information processing apparatus according to any one of (1) to (14), wherein the crack leading edge decision unit further includes
a crack progress evaluation function calculation unit configured to calculate a crack progress evaluation function that is an index indicating a possibility of realization of the crack leading edge candidate at least based on the elastic energy release rate, a crack progress evaluation function evaluation unit configured to decide the crack leading edge after the progress of the crack by selecting the crack leading edge candidate having the highest possibility of realization based on the crack progress evaluation function, and a crack progress determination unit configured to determine whether or not the crack will progress along the crack leading edge candidate based on the crack progress evaluation function.

(16) The information processing apparatus according to (15), wherein the crack progress evaluation function calculation unit calculates the crack progress evaluation function as a function with which a magnitude relation between a value of the elastic energy release rate and a value of a toughness energy necessary when the crack progresses to the crack leading edge candidate are compared.

(17) The information processing apparatus according to (15) or (16), wherein the crack progress determination unit determines whether or not the crack will progress along the crack leading edge candidate by comparing a value of the elastic energy release rate and a value of a toughness energy necessary when the crack progresses to the crack leading edge candidate.

(18) An information processing method performed by a processor, the information processing method including:

extracting a crack leading edge candidate after progress of a crack in a structure;

calculating an elastic energy release rate that indicates an elastic energy released when the crack progresses to the extracted crack leading edge candidate; and deciding a crack leading edge after the progress of the crack at least based on the elastic energy release rate, wherein the crack leading edge candidate that satisfies a predetermined condition is extracted from crack leading edge candidates obtained in terms of a construction of the structure.

(19) A program causing a processor of a computer to realize functions of:

extracting a crack leading edge candidate after progress of a crack in a structure;

calculating an elastic energy release rate that indicates an elastic energy released when the crack progresses to the extracted crack leading edge candidate; and deciding a crack leading edge after the progress of the crack at least based on the elastic energy release rate, wherein the crack leading edge candidate that satisfies a predetermined condition is extracted from crack leading edge candidates obtained in terms of a construction of the structure.

Additionally, the present technology may also be configured as below.

(1) An information processing apparatus including:

a crack leading edge candidate extraction unit configured to extract a crack leading edge candidate after progress of a crack in a structure constituted by a plurality of meshes, the candidate of which a total toughness energy necessary for separating the plurality of meshes at the time of the progress of the crack is likely to fall within a predetermined range;

an elastic energy release rate calculation unit configured to calculate an elastic energy release rate that is a rate of an elastic energy released as the meshes are separated when the crack progresses to a state shown in the extracted crack leading edge candidate; and a crack leading edge decision unit configured to decide a crack leading edge after the progress of the crack at least based on the elastic energy release rate.

(2) The information processing apparatus according to (1), wherein the crack leading edge candidate extraction unit extracts the crack leading edge candidate so that the distance between adjacent meshes among the plurality of meshes constituting the crack leading ledge after the progress of the crack is equal to or shorter than a predetermined value.

(3) The information processing apparatus according to (1) or (2), wherein the crack leading edge candidate extraction unit extracts the crack leading edge candidate so that there is no region in which the meshes are combined within a plane in which the crack leading edge formed before the progress of the crack is connected to the crack leading edge formed after the progress of the crack in the shortest distance.

(4) The information processing apparatus according to any one of (1) to (3), wherein the structure is composed of a plurality of different materials.

(5) The information processing apparatus according to (4), wherein, for a region corresponding to each material of the structure, a toughness value according to binding force of the material is set, and wherein, for a face corresponding to the interface between different materials of a structure, a toughness value according to binding force of the interface between the materials is set.

(6) The information processing apparatus according to any one of (1) to (5), wherein internal stress according to a position inside the structure is set for the structure, and wherein the elastic energy release rate calculation unit calculates the elastic energy release rate in consideration of the internal stress.

(7) The information processing apparatus according to any one of (1) to (6), wherein a toughness value according to binding force inside the structure exerted in each direction is set for each direction in the structure, and wherein the crack leading edge candidate extraction unit extracts the crack leading edge based on a crack progressing direction, and a toughness value set for each direction inside the structure.

(8) The information processing apparatus according to any one of (1) to (7), wherein the elastic energy release rate calculation unit calculates the elastic energy release rate based on a result of analysis of stress present in the structure using a finite element method.

(9) The information processing apparatus according to any one of (1) to (8), wherein the crack leading edge decision unit further includes:

a crack progress evaluation function calculation unit configured to calculate a crack progress evaluation function that is an index indicating a possibility of realization of the crack leading edge candidate at least based on the elastic energy release rate;

a crack progress evaluation function evaluation unit configured to decide the crack leading edge after the progress of the crack by extracting the crack leading edge candidate that has the highest possibility of realization based on the crack progress evaluation function; and a crack progress determination unit configured to determine whether or not the crack progresses along the crack leading edge candidate based on the crack progress evaluation function.

(10) The information processing apparatus according to (9), wherein the crack progress evaluation function calculation unit calculates the crack progress evaluation function as a function with which the magnitude relation between a value of the elastic energy release rate and a value of the total toughness energy are compared to each other.

(11) The information processing apparatus according to (9) or (10), wherein the crack progress determination unit determines whether or not the crack progresses along the crack leading edge candidate by comparing the magnitude relation between a value of the elastic energy release rate and a value of the total toughness energy.

(12) An information processing method including:
extracting a crack leading edge candidate after progress of a crack in a structure constituted by a plurality of meshes, the candidate of which a total toughness energy necessary for separating the plurality of meshes at the time of the progress of the crack is likely to fall within a predetermined range;
calculating an elastic energy release rate that is a rate of an elastic energy released as the meshes are separated when the crack progresses to a state shown in the extracted crack leading edge candidate; and
deciding a crack leading edge after the progress of the crack at least based on the elastic energy release rate.

(13) A program causing a computer to realize functions of:
extracting a crack leading edge candidate after progress of a crack in a structure constituted by a plurality of meshes, the candidate of which a total toughness energy necessary for separating the plurality of meshes at the time of the progress of the crack is likely to fall within a predetermined range;
calculating an elastic energy release rate that is a rate of an elastic energy released as the meshes are separated when the crack progresses to a state shown in the extracted crack leading edge candidate; and
deciding a crack leading edge after the progress of the crack at least based on the elastic energy release rate.

What is claimed is:

1. An information processing apparatus comprising:
analysis condition setting circuitry configured to create a shape model expressing a structure to be analyzed, the structure being composed of a plurality of different kinds of materials and the shape model being composed of a plurality of different mesh types, wherein respective ones of the plurality of different mesh types correspond to respective ones of the plurality of different kinds of materials;
crack leading edge candidate extraction circuitry configured to extract a crack leading edge candidate from the shape model after progress of a crack in the structure;
elastic energy release rate calculation circuitry configured to calculate an elastic energy release rate that indicates an elastic energy released when the crack progresses to the extracted crack leading edge candidate; and
crack leading edge decision circuitry configured to decide a crack leading edge after the progress of the crack at least based on the elastic energy release rate,
wherein the crack leading edge candidate extraction circuitry extracts the crack leading edge candidate that satisfies a predetermined condition from among crack leading edge candidates obtained in terms of the shape model.

2. The information processing apparatus according to claim 1, wherein the crack leading edge candidate extraction circuitry extracts the crack leading edge candidate of which a total toughness energy necessary for separating a plurality of meshes constituting the structure when the crack progresses falls within a predetermined range.

3. The information processing apparatus according to claim 2, wherein the crack leading edge candidate extraction circuitry extracts the crack leading edge candidate in a manner that the distance between adjacent meshes among the plurality of meshes constituting the crack leading edge after the progress of the crack has a value equal to or smaller than a predetermined value.

4. The information processing apparatus according to claim 2, wherein the crack leading edge candidate extraction circuitry extracts the crack leading edge candidate in a manner that there is no region in which the meshes are combined within a plane in which the crack leading edge formed before the progress of the crack is connected to the crack leading edge formed after the progress of the crack in the shortest distance.

5. The information processing apparatus according to claim 1,
wherein the crack leading edge candidate extraction circuitry extracts the crack leading edge candidate in two stages, including:
a first stage in which the crack progress in a surface layer region of the structure is analyzed, and
a second stage occurring after an analysis process of the first stage ends, in which the crack progress in an internal region of the structure is analyzed based on the crack occurring in the surface layer region obtained as a result of the analysis process of the first stage.

6. The information processing apparatus according to claim 5, wherein the crack leading edge candidate extraction circuitry extracts the crack leading edge candidate by searching for an angle formed within a face parallel to a surface of the structure from the crack leading edge before the progress of the crack in the analysis process of the first stage.

7. The information processing apparatus according to claim 6, wherein the crack leading edge candidate extraction circuitry extracts the crack leading edge candidate by searching for an angle formed within an evaluation face that passes nodes and is perpendicular to the surface of the structure from the nodes on the crack in the surface layer region obtained through the analysis process of the first stage in an analysis process of the second stage.

8. The information processing apparatus according to claim 5, wherein the progress of the crack on the surface of the structure is analyzed in the analysis process of the first stage.

9. The information processing apparatus according to claim 5, wherein the progress of the crack in a surface layer which includes a surface of the structure and is present at a predetermined depth from the surface is analyzed in the analysis process of the first stage.

10. The information processing apparatus according to claim 1,
wherein, for a region corresponding to each material of the structure, a toughness value according to binding force of the material is set, and
wherein, for a face corresponding to an interface between different kinds of materials of the structure, a toughness value according to binding force of the interface between the materials is set.

11. The information processing apparatus according to claim 1,
wherein internal stress according to a position inside the structure is set for the structure, and
wherein the elastic energy release rate calculation circuitry calculates the elastic energy release rate in consideration of the internal stress.

12. The information processing apparatus according to claim 1, wherein a toughness value according to binding force inside the structure exerted in each direction is set for each direction in the structure, and wherein the crack leading edge candidate extraction circuitry extracts the crack leading edge based on a crack progressing direction and a toughness value set for each direction inside the structure.

13. The information processing apparatus according to claim 1, wherein the elastic energy release rate calculation circuitry calculates the elastic energy release rate based on a result of analysis of stress on the structure using a finite element method.

14. The information processing apparatus according to claim 1, wherein the crack leading edge decision circuitry further includes crack progress evaluation function calculation circuitry configured to calculate a crack progress evaluation function that is an index indicating a possibility of realization of the crack leading edge candidate at least based on the elastic energy release rate, crack progress evaluation function evaluation circuitry configured to decide the crack leading edge after the progress of the crack by selecting the crack leading edge candidate having the highest possibility of realization based on the crack progress evaluation function, and crack progress determination circuitry configured to determine whether or not the crack will progress along the crack leading edge candidate based on the crack progress evaluation function.

15. The information processing apparatus according to claim 14, wherein the crack progress evaluation function calculation circuitry calculates the crack progress evaluation function as a function with which a magnitude relation between a value of the elastic energy release rate and a value of a toughness energy necessary when the crack progresses to the crack leading edge candidate are compared.

16. The information processing apparatus according to claim 14, wherein the crack progress determination circuitry determines whether or not the crack will progress along the crack leading edge candidate by comparing a value of the elastic energy release rate and a value of a toughness energy necessary when the crack progresses to the crack leading edge candidate.

17. An information processing method performed by a processor, the information processing method comprising:

creating a shape model expressing a structure to be analyzed, the structure being composed of a plurality of different kinds of materials and the shape model being composed of a plurality of different mesh types, wherein respective ones of the plurality of different mesh types correspond to respective ones of the plurality of different kinds of materials;

extracting a crack leading edge candidate from the shape model after progress of a crack in the structure;

calculating an elastic energy release rate that indicates an elastic energy released when the crack progresses to the extracted crack leading edge candidate; and deciding a crack leading edge after the progress of the crack at least based on the elastic energy release rate, wherein the crack leading edge candidate that satisfies a predetermined condition is extracted from among crack leading edge candidates obtained in terms of the shape model.

18. A non-transitory computer-readable medium storing instructions that, when executed by a processor of a computer, cause the computer to perform operations comprising:

creating a shape model expressing a structure to be analyzed, the structure being composed of a plurality of different kinds of materials and the shape model being composed of a plurality of different mesh types, wherein respective ones of the plurality of different mesh types correspond to respective ones of the plurality of different kinds of materials;

extracting a crack leading edge candidate from the shape model after progress of a crack in the structure;

calculating an elastic energy release rate that indicates an elastic energy released when the crack progresses to the extracted crack leading edge candidate; and deciding a crack leading edge after the progress of the crack at least based on the elastic energy release rate, wherein the crack leading edge candidate that satisfies a predetermined condition is extracted from crack leading edge candidates obtained in terms of the shape model.

\* \* \* \* \*